(12) United States Patent
Hanagan et al.

(10) Patent No.: US 8,722,678 B2
(45) Date of Patent: May 13, 2014

(54) FUNGICIDAL OXIMES AND HYDRAZONES

(75) Inventors: Mary Ann Hanagan, Newark, DE (US); Eric Allen Marshall, Rising Sun, MD (US)

(73) Assignee: E I du Pont de Nemours and Company, Wilmington, DE (US)

(*) Notice: Subject to any disclaimer, the term of this patent is extended or adjusted under 35 U.S.C. 154(b) by 0 days.

(21) Appl. No.: 13/640,092

(22) PCT Filed: Apr. 15, 2011

(86) PCT No.: PCT/US2011/032599
§ 371 (c)(1),
(2), (4) Date: Oct. 9, 2012

(87) PCT Pub. No.: WO2011/146182
PCT Pub. Date: Nov. 24, 2011

(65) Prior Publication Data
US 2013/0030002 A1 Jan. 31, 2013

Related U.S. Application Data

(60) Provisional application No. 61/346,606, filed on May 20, 2010.

(51) Int. Cl.
*A01N 43/78* (2006.01)
*A01N 43/40* (2006.01)
*A01N 43/54* (2006.01)
*A01N 43/56* (2006.01)
*A01N 43/58* (2006.01)
*A01P 3/00* (2006.01)
*C07D 277/30* (2006.01)
*C07D 401/06* (2006.01)
*C07D 417/06* (2006.01)
*C07D 417/14* (2006.01)

(52) U.S. Cl.
USPC ...... 514/252.05; 514/256; 514/326; 514/342; 514/365; 544/238; 544/333; 546/209; 546/211; 546/269.7; 548/204

(58) Field of Classification Search
None
See application file for complete search history.

(56) References Cited

U.S. PATENT DOCUMENTS

| | | |
|---|---|---|
| 2010/0190828 A1 | 7/2010 | Cristau et al. |
| 2011/0312999 A1 | 12/2011 | Cristau et al. |

FOREIGN PATENT DOCUMENTS

| | | | |
|---|---|---|---|
| WO | 2007/014290 A2 | 2/2007 | |
| WO | 2008/013622 A2 | 1/2008 | |
| WO | 2008/013925 A2 | 1/2008 | |
| WO | 2008/091594 A2 | 7/2008 | |
| WO | WO 2009055514 A2 * | 4/2009 | ............ A01N 43/80 |
| WO | 2009/094407 A2 | 7/2009 | |
| WO | 2009/094445 A2 | 7/2009 | |
| WO | 2010/066353 A1 | 6/2010 | |
| WO | 2011/134969 A1 | 11/2011 | |

OTHER PUBLICATIONS

Gregory et al., WO 2009/055514 A2 (CAS Abstract), Apr. 30, 2009.*

\* cited by examiner

*Primary Examiner* — Janet L Andres
*Assistant Examiner* — Timothy R Rozof
(74) *Attorney, Agent, or Firm* — Renee M. Lett

(57) ABSTRACT

Disclosed are compounds of Formula 1, including all stereoisomers, N-oxides, and salts thereof,

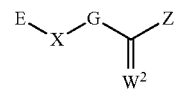

wherein
E, X, G, $W^2$ and Z are as defined in the disclosure.
Also disclosed are compositions containing the compounds of Formula 1 and methods for controlling plant disease caused by a fungal pathogen comprising applying an effective amount of a compound or a composition of the invention.
Also disclosed are compounds of Formula 1A including all stereoisomers, N-oxides, and salts thereof,

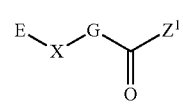

wherein
E, X, G and $Z^1$ are as defined in the disclosure.
Also disclosed is the use of the compounds of Formula 1A as intermediates for preparing compounds of Formula 1.

5 Claims, No Drawings

FUNGICIDAL OXIMES AND HYDRAZONES

FIELD OF THE INVENTION

This invention relates to certain oximes and hydrazones, their N-oxides, salts and compositions, and methods of their use as fungicides.

BACKGROUND OF THE INVENTION

The control of plant diseases caused by fungal plant pathogens is extremely important in achieving high crop efficiency. Plant disease damage to ornamental, vegetable, field, cereal, and fruit crops can cause significant reduction in productivity and thereby result in increased costs to the consumer. Many products are commercially available for these purposes, but the need continues for new compounds which are more effective, less costly, less toxic, environmentally safer or have different sites of action.

Certain pyrazole derivatives of Formula i and their use as fungicides are disclosed in PCT Patent Publication WO 2008/013925

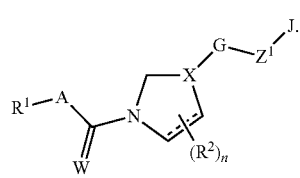

i

SUMMARY OF THE INVENTION

This invention is directed to compounds of Formula 1, or an N-oxide, or a salt thereof, agricultural compositions containing them and their use as fungicides:

$$E\diagdown_X\diagup^G\diagdown_{W^2}\diagup^Z$$

1 wherein

E is a radical selected from the group consisting of

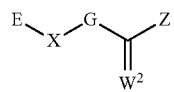

E-1

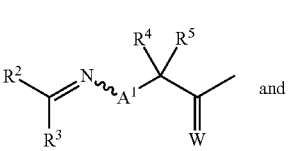

and

E-2

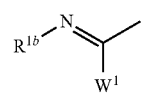

;

E-3

X is a radical selected from the group consisting of

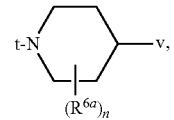

X-1

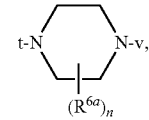

X-2

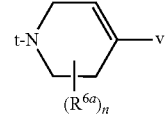

X-3

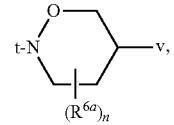

X-4

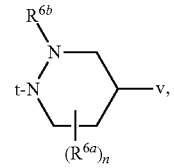

X-5

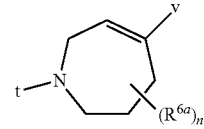

X-6

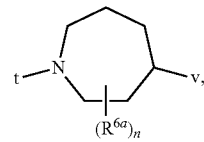

X-7

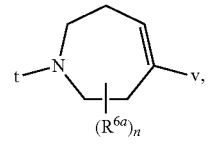

X-8

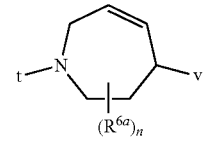

X-9

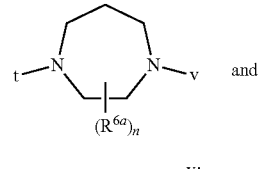 and

X-10

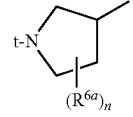

X-11 wherein the bond of X-1, X-2, X-3, X-4, X-5, X-6, X-7, X-8, X-9, X-10 or X-11 which is identified with "t" is connected to the radical identified as E of Formula 1, and the bond which is identified with "v" is connected to G;

G is a 5-membered heterocyclic ring optionally substituted with up to 3 substituents independently selected from $R^{29a}$ on carbon atom ring members and $R^{30a}$ on nitrogen atom ring members;

$W^2$ is $NOR^{12}$, $NNR^{13}R^{14}$ or NC≡N;

A is $CHR^{15}$, $NR^{16}$ or C(=O);

$A^1$ is —O—, —S—, —N($R^7$)—, —C($R^8$)$_2$—, —OC($R^8$)$_2$—, —SC($R^8$)$_2$— or —N($R^7$)C($R^8$)$_2$—, wherein the bond projecting to the left is connected to —N=C($R^2$)($R^3$), and the bond projecting to the right is connected to —C($R^4$)($R^5$)—;

W is O or S;

$W^1$ is $OR^{18}$, $SR^{19}$, $NR^{20}R^{21}$ or $R^{22}$;

$R^{1a}$ and $R^{1b}$ independently are an optionally substituted phenyl, an optionally substituted naphthalenyl or an optionally substituted 5- to 6-membered heteroaromatic ring; or cyano, $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl, $C_2$-$C_8$ haloalkynyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_4$-$C_{10}$ halocycloalkylalkyl, $C_5$-$C_{10}$ alkylcycloalkylalkyl, $C_2$-$C_8$ alkoxyalkyl, $C_2$-$C_8$ haloalkoxyalkyl, $C_4$-$C_{10}$ cycloalkoxyalkyl, $C_3$-$C_{10}$ alkoxyalkoxyalkyl, $C_2$-$C_8$ alkylthioalkyl, $C_2$-$C_8$ haloalkylthioalkyl, $C_2$-$C_8$ alkylsulfinylalkyl, $C_2$-$C_8$ alkylsulfonylalkyl, $C_3$-$C_8$ alkoxycarbonylalkyl, $C_3$-$C_8$ haloalkoxycarbonylalkyl, $C_2$-$C_8$ alkylaminoalkyl, $C_3$-$C_{10}$ dialkylaminoalkyl, $C_2$-$C_8$ haloalkylaminoalkyl, $C_4$-$C_{10}$ cycloalkylaminoalkyl, $C_1$-$C_8$ alkoxy, $C_1$-$C_8$ haloalkoxy, $C_3$-$C_8$ cycloalkoxy, $C_3$-$C_8$ halocycloalkoxy, $C_4$-$C_{10}$ cycloalkylalkoxy, $C_2$-$C_8$ alkenyloxy, $C_2$-$C_8$ haloalkenyloxy, $C_2$-$C_8$ alkynyloxy, $C_3$-$C_8$ haloalkynyloxy, $C_2$-$C_8$ alkoxyalkoxy, $C_2$-$C_8$ alkylcarbonyloxy, $C_2$-$C_8$ haloalkylcarbonyloxy, $C_1$-$C_8$ alkylthio, $C_1$-$C_8$ haloalkylthio, $C_3$-$C_8$ cycloalkylthio, $C_3$-$C_{10}$ trialkylsilyl, $C_1$-$C_8$ alkylamino, $C_2$-$C_8$ dialkylamino, $C_1$-$C_8$ haloalkylamino, $C_2$-$C_8$ halodialkylamino, $C_3$-$C_8$ cycloalkylamino, $C_2$-$C_8$ alkylcarbonylamino, $C_2$-$C_8$ haloalkylcarbonylamino, $C_1$-$C_8$ alkylsulfonylamino, $C_1$-$C_8$ haloalkylsulfonylamino, pyrrolidinyl, piperidinyl or morpholinyl;

$R^2$ is hydrogen, halogen, cyano, amino, —CHO, —C(=O)OH, —C(=O)NH$_2$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_6$ cycloalkyl, $C_3$-$C_6$ halocycloalkyl, $C_4$-$C_6$ alkylcycloalkyl, $C_4$-$C_6$ cycloalkylalkyl, $C_4$-$C_6$ halocycloalkylalkyl, $C_3$-$C_6$ cycloalkenyl, $C_3$-$C_6$ halocycloalkenyl, $C_2$-$C_6$ alkoxyalkyl, $C_2$-$C_6$ alkylthioalkyl, $C_2$-$C_6$ alkylsulfinylalkyl, $C_2$-$C_6$ alkylsulfonylalkyl, $C_2$-$C_6$ alkylaminoalkyl, $C_3$-$C_6$ dialkylaminoalkyl, $C_2$-$C_6$ haloalkylaminoalkyl, $C_2$-$C_6$ alkylcarbonyl, $C_2$-$C_6$ haloalkylcarbonyl, $C_4$-$C_6$ cycloalkylcarbonyl, $C_2$-$C_6$ alkoxycarbonyl, $C_4$-$C_6$ cycloalkoxycarbonyl, $C_5$-$C_6$ cycloalkylalkoxycarbonyl, $C_2$-$C_6$ alkylaminocarbonyl, $C_3$-$C_6$ dialkylaminocarbonyl, $C_1$-$C_6$ alkoxy, $C_1$-$C_6$ haloalkoxy, $C_3$-$C_6$ cycloalkoxy, $C_3$-$C_6$ halocycloalkoxy, $C_2$-$C_6$ alkenyloxy, $C_2$-$C_6$ haloalkenyloxy, $C_2$-$C_6$ alkynyloxy, $C_3$-$C_6$ haloalkynyloxy, $C_2$-$C_6$ alkoxyalkoxy, $C_2$-$C_6$ alkylcarbonyloxy, $C_2$-$C_6$ haloalkylcarbonyloxy, $C_1$-$C_6$ alkylthio, $C_1$-$C_6$ haloalkylthio, $C_3$-$C_6$ cycloalkylthio, $C_1$-$C_6$ alkylamino, $C_2$-$C_6$ dialkylamino, $C_1$-$C_6$ haloalkylamino, $C_2$-$C_6$ halodialkylamino, $C_3$-$C_6$ cycloalkylamino, $C_2$-$C_6$ alkylcarbonylamino, $C_2$-$C_6$ haloalkylcarbonylamino, $C_1$-$C_6$ alkylsulfonylamino or $C_1$-$C_6$ haloalkylsulfonylamino;

$R^3$ is hydrogen, halogen, cyano, hydroxy, $C_1$-$C_3$ alkyl, $C_1$-$C_3$ haloalkyl, $C_1$-$C_3$ alkoxy or $C_1$-$C_3$ haloalkoxy; or $R^2$ and $R^3$ are taken together with the carbon atom to which they are attached to form a 3- to 7-membered ring containing ring members selected from carbon atoms and up to 4 heteroatoms independently selected from up to 2 O, up to 2 S, up to 2 N and up to 2 Si atoms, wherein up to 3 carbon atom ring members are independently selected from C(=O) and C(=S), the sulfur atom ring members are independently selected from S(=O)$_s$(=NR$^{17}$)$_f$ and the silicon atom ring members are independently selected from SiR$^{10}$R$^{11}$, the ring optionally substituted with up to 4 substituents independently selected from halogen, cyano, $C_1$-$C_2$ alkyl, $C_1$-$C_2$ haloalkyl, $C_1$-$C_2$ alkoxy and $C_1$-$C_2$ haloalkoxy on carbon atom ring members and cyano, $C_1$-$C_2$ alkyl and $C_1$-$C_2$ alkoxy on nitrogen atom ring members;

$R^4$ is optionally substituted phenyl, optionally substituted naphthalenyl or an optionally substituted 5- to 6-membered heteroaromatic ring; or hydrogen, halogen, cyano, hydroxy, —CHO, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_2$-$C_4$ alkoxyalkyl, $C_2$-$C_4$ alkylthioalkyl, $C_2$-$C_4$ alkylsulfinylalkyl, $C_2$-$C_4$ alkylsulfonylalkyl, $C_2$-$C_4$ alkylcarbonyl, $C_2$-$C_4$ haloalkylcarbonyl, $C_2$-$C_5$ alkoxycarbonyl, $C_2$-$C_5$ alkylaminocarbonyl, $C_3$-$C_5$ dialkylaminocarbonyl, $C_1$-$C_4$ alkoxy, $C_1$-$C_4$ haloalkoxy, $C_1$-$C_4$ alkylthio, $C_1$-$C_4$ haloalkylthio, $C_1$-$C_4$ alkylsulfinyl, $C_1$-$C_4$ haloalkylsulfinyl, $C_1$-$C_4$ alkylsulfonyl, $C_1$-$C_4$ haloalkylsulfonyl, $C_2$-$C_4$ alkylcarbonyloxy, $C_2$-$C_4$ haloalkylcarbonyloxy, $C_2$-$C_5$ alkoxycarbonyloxy, $C_2$-$C_5$ alkylaminocarbonyloxy or $C_3$-$C_5$ dialkylaminocarbonyloxy;

$R^5$ is hydrogen, $C_1$-$C_3$ alkyl or $C_1$-$C_3$ haloalkyl;

each $R^{6a}$ is independently $C_1$-$C_4$ alkyl, $C_1$-$C_4$ alkenyl, $C_1$-$C_4$ haloalkyl, $C_1$-$C_4$ alkoxy, halogen, cyano or hydroxy; or two $R^{6a}$ are taken together as $C_1$-$C_4$ alkylene or $C_2$-$C_4$ alkenylene to form a bridged bicyclic or fused bicyclic ring system; or two $R^{6a}$ attached to adjacent ring carbon atoms joined by a double bond are taken together as —CH=CH—CH=CH— optionally substituted with up to 3 substituents selected from $C_1$-$C_4$ alkyl, $C_1$-$C_4$ haloalkyl, $C_1$-$C_4$ alkoxy, $C_1$-$C_4$ haloalkoxy, halogen, hydroxy, amino, cyano and nitro;

$R^{6b}$ is hydrogen, cyano, $C_1$-$C_3$ alkyl, $C_1$-$C_3$ haloalkyl, $C_1$-$C_3$ alkoxy, $C_2$-$C_3$ alkylcarbonyl, $C_2$-$C_3$ alkoxycarbonyl or $C_3$-$C_6$ cycloalkyl;

Z is hydrogen, cyano, halogen; or Q; or $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_6$ cycloalkyl, $C_3$-$C_6$ halocycloalkyl, $C_4$-$C_8$ alkylcycloalkyl, $C_4$-$C_8$ cycloalkylalkyl, $C_4$-$C_8$ halocycloalkylalkyl, $C_5$-$C_8$ alkylcycloalkylalkyl, $C_1$-$C_6$ alkoxy, $C_2$-$C_6$ alkoxyalkyl, $C_1$-$C_6$ hydroxyalkyl, $C_4$-$C_8$ cycloalkoxyalkyl, $C_3$-$C_6$ alkoxyalkoxyalkyl, $C_1$-$C_6$ alkylthio, $C_1$-$C_6$ thioalkyl, $C_2$-$C_6$ alkylthioalkyl, $C_2$-$C_6$ alkylsulfinylalkyl, $C_2$-$C_6$ alkylsulfonylalkyl, $C_1$-$C_6$ alkylamino, $C_2$-$C_6$ alkylaminoalkyl, $C_3$-$C_6$ dialkylamino, $C_1$-$C_6$ aminoalkyl, $C_3$-$C_6$ dialkylaminoalkyl, $C_2$-$C_6$ haloalkylaminoalkyl, $C_4$-$C_8$ cycloalkylaminoalkyl, $C_2$-$C_6$ alkylcarbonyl, $C_2$-$C_6$ haloalkylcarbonyl, $C_4$-$C_8$ cycloalkylcarbonyl, $C_2$-$C_6$ alkoxycarbonyl, $C_2$-$C_6$ alkylaminocarbonyl, $C_3$-$C_8$ dialkylaminocarbonyl or $C_4$-$C_8$ cycloalkylaminocarbonyl, each optionally substituted by up to one Q and up to 2 substituents selected from $C_1$-$C_3$ alkyl, $C_1$-$C_3$ haloalkyl, $C_1$-$C_3$ alkoxy, hydroxyl and cyano;

Q is phenyl, phenyloxy, phenylthio, phenylamino, phenylcarbonyl or naphthalenyl, each optionally substituted on carbon atom ring members with up to 5 substituents independently selected from $R^{9a}$; or a 5- to 6-membered heteroaromatic ring or an 8- to 11-membered heteroaromatic bicyclic ring system containing ring members selected from carbon atoms and up to 4 heteroatoms independently selected from up to 2 O, up to 2 S and up to 4 N atoms, and optionally substituted with up to 5 substituents independently selected from $R^{9a}$ on carbon atom ring members and $R^{9b}$ on nitrogen atom ring members; or a 3- to 7-membered nonaromatic carbocyclic ring, a 5- to 7-membered nonaromatic heterocyclic ring or an 8- to 11-membered nonaromatic bicyclic ring system, each ring or ring system containing ring members selected from carbon atoms and up to 4 heteroatoms independently selected from up to 2 O, up to 2 S, up to 4 N and up to 2 Si atoms, wherein up to 3 carbon atom ring members are independently selected from C(=O) and C(=S), the sulfur atom ring members are independently selected from $S(=O)_s(=NR^{17})_f$, and the silicon atom ring members are independently selected from $SiR^{10}R^{11}$, each ring or ring system optionally substituted with up to 5 substituents independently selected from $R^{9a}$ on carbon atom ring members and $R^{9b}$ on nitrogen atom ring members;

$R^7$ is hydrogen, cyano, $C_1$-$C_4$ alkyl, $C_1$-$C_4$ haloalkyl, $C_2$-$C_4$ alkoxyalkyl, $C_2$-$C_4$ alkylthioalkyl, $C_2$-$C_4$ alkylcarbonyl, $C_2$-$C_4$ haloalkylcarbonyl, $C_2$-$C_4$ alkoxycarbonyl, $C_2$-$C_4$ alkylaminocarbonyl, $C_3$-$C_5$ dialkylaminocarbonyl, $C_1$-$C_4$ alkylsulfonyl or $C_1$-$C_4$ haloalkylsulfonyl; or $R^3$ and $R^7$ are taken together with the linking atoms to which they are attached to form a 5- to 7-membered partially saturated ring containing ring members, in addition to the linking atoms, selected from carbon atoms and up to 3 heteroatoms independently selected from up to 1 O, up to 1 S and up to 1 N atom, the ring optionally substituted with up to 3 substituents independently selected from halogen, cyano, nitro, $C_1$-$C_2$ alkyl, $C_1$-$C_2$ haloalkyl, $C_1$-$C_2$ alkoxy and $C_1$-$C_2$ haloalkoxy on carbon atom ring members and cyano, $C_1$-$C_2$ alkyl and $C_1$-$C_2$ alkoxy on nitrogen atom ring members;

each $R^8$ is independently hydrogen, $C_1$-$C_3$ alkyl or $C_1$-$C_3$ haloalkyl;

each $R^{9a}$ is independently halogen, hydroxy, amino, cyano, nitro, $C_1$-$C_6$ alkyl, $C_2$-$C_6$ alkenyl, $C_2$-$C_6$ alkynyl, $C_3$-$C_6$ cycloalkyl, $C_4$-$C_{10}$ cycloalkylalkyl, $C_4$-$C_{10}$ alkylcycloalkyl, $C_5$-$C_{10}$ alkylcycloalkylalkyl, $C_6$-$C_{14}$ cycloalkylcycloalkyl, $C_1$-$C_6$ haloalkyl, $C_2$-$C_6$ haloalkenyl, $C_2$-$C_6$ haloalkynyl, $C_3$-$C_6$ halocycloalkyl, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_1$-$C_4$ hydroxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl or $C_3$-$C_6$ trialkylsilyl; or phenyl or naphthalenyl optionally substituted with up to 3 substituents independently selected from halogen, cyano, $C_1$-$C_2$ alkyl, $C_1$-$C_2$ haloalkyl, $C_1$-$C_2$ alkoxy and $C_1$-$C_2$ haloalkoxy; or a 5- to 6-membered heteroaromatic ring containing ring members selected from carbon atoms and up to 4 heteroatoms independently selected from up to 2 O, up to 2 S and up to 4 N atoms, and optionally substituted with up to 3 substituents independently selected from halogen, cyano, $C_1$-$C_2$ alkyl, $C_1$-$C_2$ haloalkyl, $C_1$-$C_2$ alkoxy and $C_1$-$C_2$ haloalkoxy on carbon atom ring members and cyano, $C_1$-$C_2$ alkyl and $C_1$-$C_2$ alkoxy on nitrogen atom ring members; or a 3- to 7-membered nonaromatic ring containing ring members selected from carbon atoms and up to 4 heteroatoms independently selected from up to 2 O, up to 2 S and up to 4 N atoms, wherein up to 3 carbon atom ring members are independently selected from C(=O) and C(=S), the ring optionally substituted with up to 3 substituents independently selected from halogen, cyano, $C_1$-$C_2$ alkyl, $C_1$-$C_2$ haloalkyl, $C_1$-$C_2$ alkoxy and $C_1$-$C_2$ haloalkoxy on carbon atom ring members and cyano, $C_1$-$C_2$ alkyl and $C_1$-$C_2$ alkoxy on nitrogen atom ring members;

each $R^{9b}$ is independently hydrogen, cyano, $C_1$-$C_3$ alkyl, $C_1$-$C_3$ haloalkyl, $C_1$-$C_3$ alkoxy, $C_2$-$C_3$ alkylcarbonyl, $C_2$-$C_3$ alkoxycarbonyl or $C_3$-$C_6$ cycloalkyl;

each $R^{10}$ and $R^{11}$ is independently $C_1$-$C_5$ alkyl, $C_2$-$C_5$ alkenyl, $C_2$-$C_5$ alkynyl, $C_3$-$C_5$ cycloalkyl, $C_3$-$C_6$ halocycloalkyl, $C_4$-$C_{10}$ cycloalkylalkyl, $C_4$-$C_7$ alkylcycloalkyl, $C_5$-$C_7$ alkylcycloalkylalkyl, $C_1$-$C_5$ haloalkyl, $C_1$-$C_5$ alkoxy or $C_1$-$C_5$ haloalkoxy;

$R^{12}$ is hydrogen; or $Q^1$; or $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_2$-$C_4$ alkoxyalkyl, $C_2$-$C_4$ alkylthioalkyl, $C_2$-$C_4$ alkylsulfinylalkyl, $C_2$-$C_4$ alkylsulfonylalkyl, $C_2$-$C_4$ alkylcarbonyl, $C_2$-$C_4$ haloalkylcarbonyl, $C_2$-$C_5$ alkoxycarbonyl, $C_2$-$C_5$ hydroxyalkylcarbonyl, $C_2$-$C_5$ carboxyalkyl, $C_2$-$C_5$ alkylaminocarbonyl, $C_3$-$C_5$ dialkylaminocarbonyl, $C_2$-$C_4$ aminocarbonylalkyl or $C_3$-$C_6$ cycloalkyl, each optionally substituted by up to one $Q^1$ and up to 2 substituents selected from $C_1$-$C_3$ alkyl, $C_1$-$C_3$ haloalkyl, $C_1$-$C_3$ alkoxy, hydroxyl and cyano;

$R^{13}$ is hydrogen, $C_1$-$C_4$ alkyl, $C_2$-$C_4$ alkenyl, $C_3$-$C_4$ alkynyl or $C_1$-$C_4$ haloalkyl;

$R^{14}$ is hydrogen, cyano or $Q^1$; or $C_1$-$C_4$ alkyl, $C_2$-$C_4$ alkenyl, $C_3$-$C_4$ alkynyl, $C_1$-$C_4$ haloalkyl, $C_2$-$C_4$ haloalkenyl, $C_2$-$C_4$ haloalkynyl, $C_2$-$C_4$ alkoxyalkyl, $C_2$-$C_4$ alkylthioalkyl, $C_2$-$C_4$ alkylsulfinylalkyl, $C_2$-$C_4$ alkylsulfonylalkyl, $C_2$-$C_4$ alkylcarbonyl, $C_2$-$C_4$ haloalkylcarbonyl, $C_2$-$C_5$ alkoxycarbonyl, $C_2$-$C_5$ hydroxyalkylcarbonyl, $C_2$-$C_5$ carboxyalkyl, $C_2$-$C_5$ alkylaminocarbonyl, $C_3$-$C_5$ dialkylaminocarbonyl, $C_2$-$C_4$ aminocarbonylalkyl or $C_3$-$C_6$ cycloalkyl, each optionally substituted by up to one $Q^1$ and up to 2 substituents selected from $C_1$-$C_3$ alkyl, $C_1$-$C_3$ haloalkyl, $C_1$-$C_3$ alkoxy, hydroxyl and cyano;

$Q^1$ is phenyl, naphthalenyl or phenylcarbonyl each optionally substituted on carbon atom ring members with up to 5 substituents independently selected from $R^{9a}$; or a 5- to 6-membered heteroaromatic ring or an 8- to 11-membered heteroaromatic bicyclic ring system containing ring members selected from carbon atoms and up to 4 heteroatoms independently selected from up to 2 O, up to 2 S and up to 4 N atoms, and optionally substituted with up to 5 substituents independently selected from $R^{9a}$ on carbon atom ring members and $R^{9b}$ on nitrogen atom ring members; or a 3- to 7-membered nonaromatic carbocyclic ring, a 5- to 7-membered nonaromatic heterocyclic ring or an 8- to 11-membered nonaromatic bicyclic ring system, each ring or ring system containing ring members selected from carbon atoms and up to 4 heteroatoms independently selected from up to 2 O, up to 2 S, up to 4 N and up to 2 Si atoms, wherein up to 3 carbon atom ring members are independently selected from C(=O) and C(=S), the sulfur atom ring members are independently selected from $S(=O)_s(=NR^{17})_f$, and the silicon atom ring members are independently selected from $SiR^{10}R^{11}$, each ring or ring system optionally substituted with up to 5 substituents independently selected from $R^{9a}$ on carbon atom ring members and $R^{9b}$ on nitrogen atom ring members;

$R^{15}$ is hydrogen, halogen, cyano, hydroxy, —CHO, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_2$-$C_4$ alkoxyalkyl, $C_2$-$C_4$ alkylthioalkyl, $C_2$-$C_4$ alkylsulfinylalkyl, $C_2$-$C_4$ alkylsulfonylalkyl, $C_3$-$C_5$ alkoxycarbonylalkyl, $C_2$-$C_4$ alkylcarbonyl, $C_2$-$C_4$ haloalkylcarbonyl, $C_2$-$C_5$ alkoxycarbonyl, $C_2$-$C_5$ alkylaminocarbonyl, $C_3$-$C_5$ dialkylaminocarbonyl, $C_1$-$C_4$ alkoxy, $C_1$-$C_4$ haloalkoxy, $C_1$-$C_4$ alkylthio, $C_1$-$C_4$ haloalkylthio, $C_1$-$C_4$ alkylsulfinyl, $C_1$-$C_4$ haloalkylsulfinyl, $C_1$-$C_4$ alkylsulfonyl or $C_1$-$C_4$ haloalkylsulfonyl; provided that when $R^{15}$ is hydroxy, then $R^{1a}$ is bonded through a carbon atom to A in Formula 1;

$R^{16}$ is hydrogen, $C_1$-$C_4$ alkyl, $C_2$-$C_4$ alkenyl, $C_3$-$C_4$ alkynyl, $C_1$-$C_4$ haloalkyl, $C_2$-$C_4$ haloalkenyl, $C_2$-$C_4$ haloalkynyl, $C_2$-$C_4$ alkoxyalkyl, $C_2$-$C_4$ alkylthioalkyl, $C_2$-$C_4$ alkylsulfinylalkyl, $C_2$-$C_4$ alkylsulfonylalkyl, $C_2$-$C_4$ alkylcarbonyl, $C_2$-$C_4$ haloalkylcarbonyl, $C_2$-$C_5$ alkoxycarbonyl, $C_3$-$C_5$ alkoxycarbonylalkyl, $C_2$-$C_5$ alkylaminocarbonyl, $C_3$-$C_5$ dialkylaminocarbonyl, $C_1$-$C_4$ alkylsulfonyl or $C_1$-$C_4$ haloalkylsulfonyl;

each $R^{17}$ is independently hydrogen, cyano, $C_1$-$C_6$ alkyl, $C_1$-$C_6$ haloalkyl, $C_3$-$C_8$ cycloalkyl, $C_3$-$C_8$ halocycloalkyl, $C_1$-$C_6$ alkoxy, $C_1$-$C_6$ haloalkoxy, $C_1$-$C_6$ alkylamino, $C_2$-$C_8$ dialkylamino, $C_1$-$C_6$ haloalkylamino or phenyl;

$R^{18}$ and $R^{19}$ independently are $C_1$-$C_6$ alkyl, $C_3$-$C_6$ alkenyl, $C_3$-$C_6$ alkynyl, $C_1$-$C_6$ haloalkyl, $C_3$-$C_6$ haloalkenyl, $C_3$-$C_6$ haloalkynyl, $C_3$-$C_6$ cycloalkyl, $C_3$-$C_6$ halocycloalkyl, $C_4$-$C_8$ alkylcycloalkyl, $C_4$-$C_8$ cycloalkylalkyl, $C_4$-$C_8$ halocycloalkylalkyl, $C_5$-$C_8$ alkylcycloalkylalkyl, $C_2$-$C_6$ alkoxyalkyl, $C_4$-$C_8$ cycloalkoxyalkyl, $C_3$-$C_6$ alkoxyalkoxyalkyl, $C_2$-$C_6$ alkylthioalkyl, $C_2$-$C_6$ alkylsulfinylalkyl, $C_2$-$C_6$ alkylsulfonylalkyl, $C_2$-$C_6$ alkylaminoalkyl, $C_3$-$C_6$ dialkylaminoalkyl, $C_2$-$C_6$ haloalkylaminoalkyl, $C_4$-$C_8$ cycloalkylaminoalkyl, $C_2$-$C_6$ alkylcarbonyl, $C_2$-$C_6$ haloalkylcarbonyl, $C_4$-$C_8$ cycloalkylcarbonyl, $C_2$-$C_6$ alkoxycarbonyl, $C_2$-$C_6$ alkylaminocarbonyl, $C_3$-$C_8$ dialkylaminocarbonyl or $C_4$-$C_8$ cycloalkylaminocarbonyl;

$R^{20}$ is hydrogen, cyano, hydroxy, amino, $C_1$-$C_6$ alkyl, $C_3$-$C_6$ alkenyl, $C_3$-$C_6$ alkynyl, $C_1$-$C_6$ haloalkyl, $C_3$-$C_6$ haloalkenyl, $C_3$-$C_6$ haloalkynyl, $C_3$-$C_6$ cycloalkyl, $C_4$-$C_8$ cycloalkylalkyl, $C_2$-$C_6$ alkoxyalkyl, $C_1$-$C_6$ alkoxy, $C_1$-$C_6$ haloalkoxy, $C_1$-$C_6$ alkylsulfonyl, $C_1$-$C_6$ haloalkylsulfonyl, $C_2$-$C_6$ alkylcarbonyl, $C_2$-$C_6$ haloalkylcarbonyl, $C_1$-$C_6$ alkylamino, $C_2$-$C_8$ dialkylamino, $C_1$-$C_6$ haloalkylamino or $C_2$-$C_8$ halodialkylamino;

$R^{21}$ is hydrogen, $C_1$-$C_6$ alkyl, $C_3$-$C_6$ alkenyl, $C_3$-$C_6$ alkynyl, $C_1$-$C_6$ haloalkyl or $C_3$-$C_6$ cycloalkyl; or $R^{20}$ and $R^{21}$ are taken together as —$(CH_2)_4$—, —$(CH_2)_5$— or —$(CH_2)_2O(CH_2)_2$—;

$R^{22}$ is hydrogen, halogen, cyano, $C_1$-$C_4$ alkyl, $C_1$-$C_4$ haloalkyl, $C_2$-$C_4$ alkoxyalkyl, $C_2$-$C_4$ alkylcarbonyl, $C_2$-$C_4$ alkoxycarbonyl, $C_2$-$C_3$ alkylaminocarbonyl or $C_3$-$C_6$ dialkylaminocarbonyl;

each $R^{29a}$ is independently hydrogen, halogen, $C_1$-$C_3$ alkyl or $C_1$-$C_3$ haloalkyl;

each $R^{30a}$ is independently hydrogen or $C_1$-$C_3$ alkyl;

n is 0, 1 or 2; and s and f are independently 0, 1 or 2 in each instance of $S(=O)_s(=NR^{17})_f$, provided that the sum of s and f is 0, 1 or 2;

provided that the compound of Formula 1 is other than 4-[4-[(hydroxyimino)methyl]-2-thiazolyl]-1-[[5-methyl-3-(trifluoromethyl)-1H-pyrazol-1-yl]acetyl]piperidine or 5-methyl-2-[1-[2-[5-methyl-3-(trifluoromethyl)-1H-pyrazol-1-yl]acetyl]-4-piperidinyl]-4-thiazole-carboxaldehyde 4-oxime.

This invention also relates to a fungicidal composition comprising (a) a compound of the invention (i.e. in a fungicidally effective amount); and (b) at least one additional component selected from the group consisting of surfactants, solid diluents and liquid diluents.

This invention also relates to a fungicidal composition comprising (a) a compound of the invention; and (b) at least one other fungicide (e.g., at least one other fungicide having a different site of action).

This invention further relates to a method for controlling plant diseases caused by fungal plant pathogens comprising applying to the plant or portion thereof, or to the plant seed, a fungicidally effective amount of a compound of the invention (e.g., as a composition described herein).

The invention also relates to compounds of Formula 1A or an N-oxide, or a salt thereof

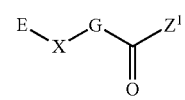

1A wherein $Z^1$ is $CH_2CH_2Q$, CH=CHQ, C≡CQ and $CH_2CH(OH)Q$; and

E, X, G and Q are as defined above for Formula 1.

This invention further relates to the use of the compounds of Formula 1A as intermediates for preparing compounds of Formula 1.

DETAILS OF THE INVENTION

As used herein, the terms "comprises," "comprising," "includes," "including," "has," "having," "contains", "containing," "characterized by" or any other variation thereof, are intended to cover a non-exclusive inclusion, subject to any limitation explicitly indicated. For example, a composition, mixture, process, method, article, or apparatus that comprises a list of elements is not necessarily limited to only those elements but may include other elements not expressly listed or inherent to such composition, mixture, process, method, article, or apparatus.

The transitional phrase "consisting of" excludes any element, step, or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition, method or apparatus that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Where applicants have defined an invention or a portion thereof with an open-ended term such as "comprising," it should be readily understood that (unless otherwise stated) the description should be interpreted to also describe such an invention using the terms "consisting essentially of" or "consisting of."

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As referred to in the present disclosure and claims, "plant" includes members of Kingdom Plantae, particularly seed plants (Spermatopsida), at all life stages, including young plants (e.g., germinating seeds developing into seedlings) and mature, reproductive stages (e.g., plants producing flowers and seeds). Portions of plants include geotropic members typically growing beneath the surface of the growing medium (e.g., soil), such as roots, tubers, bulbs and corms, and also members growing above the growing medium, such as foliage (including stems and leaves), flowers, fruits and seeds.

As referred to herein, the term "seedling", used either alone or in a combination of words means a young plant developing from the embryo of a seed.

In the above recitations, the term "alkyl", used either alone or in compound words such as "alkylthio" or "haloalkyl" includes straight-chain or branched alkyl such as methyl, ethyl, n-propyl, i-propyl, or the different butyl, pentyl or hexyl isomers. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" also includes moieties comprised of multiple triple bonds such as 2,5-hexadiynyl. "Alkylene" denotes a straight-chain or branched alkanediyl. Examples of "alkylene" include $CH_2$, $CH_2CH_2$, $CH(CH_3)$, $CH_2CH_2CH_2$, $CH_2CH(CH_3)$, and the different butylene isomers. "Alkenylene" denotes a straight-chain or branched alkenediyl containing one olefinic bond. Examples of "alkenylene" include $CH=CH$, $CH_2CH=CH$, $CH=C(CH_3)$ and the different butenylene isomers. "Alkynylene" denotes a straight-chain or branched alkynediyl containing one triple bond. Examples of "alkynylene" include $C≡C$, $CH_2C≡C$, $C≡CCH_2$, and the different butynylene isomers.

"Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2CH_2OCH_2$ and $CH_3CH_2OCH_2CH_2$. "Alkoxyalkoxy" denotes alkoxy substitution on alkoxy. "Alkenyloxy" includes straight-chain or branched alkenyloxy moieties. Examples of "alkenyloxy" include $H_2C=CHCH_2O$, $(CH_3)_2C=CHCH_2O$, $(CH_3)CH=CHCH_2O$, $(CH_3)CH=C(CH_3)CH_2O$ and $CH_2=CHCH_2CH_2O$. "Alkynyloxy" includes straight-chain or branched alkynyloxy moieties. Examples of "alkynyloxy" include $HC≡CCH_2O$, $CH_3C≡CCH_2O$ and $CH_3C≡CCH_2CH_2O$. "Alkylthio" includes branched or straight-chain alkylthio moieties such as methylthio, ethylthio, and the different propylthio, butylthio, pentylthio and hexylthio isomers. "Alkylsulfinyl" includes both enantiomers of an alkylsulfinyl group. Examples of "alkylsulfinyl" include $CH_3S(O)—$, $CH_3CH_2S(O)—$, $CH_3CH_2CH_2S(O)—$, $(CH_3)_2CHS(O)—$ and the different butylsulfinyl, pentylsulfinyl and hexylsulfinyl isomers. Examples of "alkylsulfonyl" include $CH_3S(O)_2—$, $CH_3CH_2S(O)_2—$, $CH_3CH_2CH_2S(O)_2—$, $(CH_3)_2CHS(O)_2—$, and the different butylsulfonyl, pentylsulfonyl and hexylsulfonyl isomers. "Alkylthioalkyl" denotes alkylthio substitution on alkyl. Examples of "alkylthioalkyl" include $CH_3SCH_2$, $CH_3SCH_2CH_2$, $CH_3CH_2SCH_2$, $CH_3CH_2CH_2CH_2SCH_2$ and $CH_3CH_2SCH_2CH_2$.

"Trialkylsilyl" includes 3 branched and/or straight-chain alkyl radicals attached to and linked through a silicon atom, such as trimethylsilyl, triethylsilyl and tert-butyldimethylsilyl.

"Hydroxyalkyl" denotes an alkyl group substituted with one hydroxy group. Examples of "hydroxyalkyl" include $HOCH_2CH_2$, $CH_3CH_2(OH)CH$ and $HOCH_2CH_2CH_2$.

"Alkylamino", "dialkylamino" and the like, are defined analogously to the above examples. The term "halodialkylamino" denotes a dialkylamino group substituted on at least one alkyl moiety with one or more halogen atoms which may be the same or different. Examples of "halodialkylamino" include $CF_3(CH_3)N—$, $(CF_3)_2N—$ and $CH_2Cl(CH_3)N—$. "Cycloalkylamino" means the amino nitrogen atom is attached to a cycloalkyl radical and a hydrogen atom and includes groups such as cyclopropylamino, cyclobutylamino, cyclopentylamino and cyclohexylamino. "Haloalkylaminoalkyl" denotes an alkylaminoalkyl group substituted on the amino nitrogen or either alkyl moiety or a combination thereof with one or more halogen atoms which may be the same or different. "Haloalkylaminoalkyl" includes a halogen group attached to any of the alkyl moieties as well as nitrogen. Examples of "haloalkylaminoalkyl" include $ClCH_2CH_2NHCH_2—$ and $CH_3NCH(CH_2CH_2Cl)—$.

"Cycloalkyl" includes, for example, cyclopropyl, cyclobutyl, cyclopentyl and cyclohexyl. The term "alkylcycloalkyl" denotes alkyl substitution on a cycloalkyl moiety and includes, for example, ethylcyclopropyl, i-propylcyclobutyl, 3-methylcyclopentyl and 4-methylcyclohexyl. The term "cycloalkylalkyl" denotes cycloalkyl substitution on an alkyl moiety. Examples of "cycloalkylalkyl" include cyclopropylmethyl, cyclopentylethyl, and other cycloalkyl moieties bonded to straight-chain or branched alkyl groups. The term "cycloalkoxy" denotes cycloalkyl linked through an oxygen atom such as cyclopentyloxy and cyclohexyloxy. "Cycloalkylalkoxy" denotes cycloalkylalkyl linked through an oxygen atom attached to the alkyl chain. Examples of "cycloalkylalkoxy" include cyclopropylmethoxy, cyclopentylethoxy, and other cycloalkyl moieties bonded to straight-chain or branched alkoxy groups. "Cycloalkenyl" includes groups such as cyclopentenyl and cyclohexenyl as well as groups with more than one double bond such as 1,3- and 1,4-cyclohexadienyl.

The term "halogen", either alone or in compound words such as "haloalkyl", or when used in descriptions such as "alkyl substituted with halogen" includes fluorine, chlorine, bromine or iodine. Further, when used in compound words such as "haloalkyl", or when used in descriptions such as "alkyl substituted with halogen" said alkyl may be partially or fully substituted with halogen atoms which may be the same or different. Examples of "haloalkyl" or "alkyl substituted with halogen" include $F_3C-$, $ClCH_2-$, $CF_3CH_2-$ and $CF_3CCl_2-$. The terms "halocycloalkyl", "haloalkoxy", "haloalkylthio", "haloalkenyl", "haloalkynyl", and the like, are defined analogously to the term "haloalkyl". Examples of "haloalkoxy" include $CF_3O-$, $CCl_3CH_2O-$, $HCF_2CH_2CH_2O-$ and $CF_3CH_2O-$. Examples of "haloalkylthio" include $CCl_3S-$, $CF_3S-$, $CCl_3CH_2S-$ and $ClCH_2CH_2CH_2S-$. Examples of "haloalkylsulfinyl" include $CF_3S(O)-$, $CCl_3S(O)-$, $CF_3CH_2S(O)-$ and $CF_3CF_2S(O)-$. Examples of "haloalkylsulfonyl" include $CF_3S(O)_2-$, $CCl_3S(O)_2-$, $CF_3CH_2S(O)_2-$ and $CF_3CF_2S(O)_2-$. Examples of "haloalkenyl" include $(Cl)_2C=CHCH_2-$ and $CF_3CH_2CH=CHCH_2-$. Examples of "haloalkynyl" include $HC\equiv CCHCl-$, $CF_3C\equiv C-$, $CCl_3C\equiv C-$ and $FCH_2C\equiv CCH_2-$.

Examples of "alkylcarbonyl" include $CH_3C(O)$, $CH_3CH_2CH_2C(O)$ and $(CH_3)_2CHC(O)$. Examples of "alkoxycarbonyl" include $CH_3OC(=O)$, $CH_3CH_2OC(=O)$, $CH_3CH_2CH_2OC(=O)$, $(CH_3)_2CHOC(=O)$ and the different butoxy- or pentoxycarbonyl isomers. Examples of "alkylaminocarbonyl" include $CH_3NHC(=O)-$, $CH_3CH_2NHC(=O)-$, $CH_3CH_2CH_2NHC(=O)-$, $(CH_3)_2CHNHC(=O)-$ and the different butylamino- or pentylaminocarbonyl isomers. Examples of "dialkylaminocarbonyl" include $(CH_3)_2NC(=O)-$, $(CH_3CH_2)_2NC(=O)-$, $CH_3CH_2(CH_3)NC(=O)-$, $(CH_3)_2CHN(CH_3)C(=O)-$ and $CH_3CH_2CH_2(CH_3)NC(=O)-$. The term "alkylcarbonyloxy" denotes straight-chain or branched alkyl bonded to a $C(=O)O$ moiety. Examples of "alkylcarbonyloxy" include $CH_3CH_2C(=O)O$ and $(CH_3)_2CHC(=O)O$.

The total number of carbon atoms in a substituent group is indicated by the "$C_i$-$C_j$" prefix where i and j are numbers from 1 to 10. For example, $C_1$-$C_4$ alkylsulfonyl designates methylsulfonyl through butylsulfonyl; $C_2$ alkoxyalkyl designates $CH_3OCH_2-$; $C_3$ alkoxyalkyl designates, for example, $CH_3CH(OCH_3)-$, $CH_3OCH_2CH_2-$ or $CH_3CH_2OCH_2-$; and $C_4$ alkoxyalkyl designates the various isomers of an alkyl group substituted with an alkoxy group containing a total of four carbon atoms, examples including $CH_3CH_2CH_2OCH_2-$ and $CH_3CH_2OCH_2CH_2-$.

The term "unsubstituted" in connection with a group such as a ring or ring system means the group does not have any substituents other than its one or more attachments to the remainder of Formula 1. The term "optionally substituted" means that the number of substituents can be zero. Unless otherwise indicated, optionally substituted groups may be substituted with as many optional substituents as can be accommodated by replacing a hydrogen atom with a non-hydrogen substituent on any available carbon or nitrogen atom. Commonly, the number of optional substituents (when present) ranges from 1 to 4. As used herein, the term "optionally substituted" is used interchangeably with the phrase "substituted or unsubstituted" or with the term "(un)substituted." When a group (e.g., X) contains a substituent (e.g., $R^{6b}$) which can be hydrogen, then when this substituent is taken as hydrogen, it is recognized that this is equivalent to said group being unsubstituted.

The number of optional substituents may be restricted by an expressed limitation. For example, the phrase "optionally substituted with up to 5 substituents independently selected from $R^{9a}$" means that 0, 1, 2, 3, 4 or 5 substituents can be present if the number of available connection points allows. When a range specified for the number of substituents (e.g., p being an integer from 1 to 5 in Exhibit 4) exceeds the number of positions available for substituents on a ring (e.g., 2 positions available for $(R^{9a})_p$ on Q-5 in Exhibit 4), the actual higher end of the range is recognized to be the number of available positions.

When a compound is substituted with a substituent bearing a subscript that indicates the number of said substituents can exceed 1, said substituents (when they exceed 1) are independently selected from the group of defined substituents, e.g., $(R^{9a})_p$, p is 0, 1, 2, 3, 4 or 5. When a group contains a substituent which can be hydrogen, for example $R^{6b}$, then when this substituent is taken as hydrogen, it is recognized that this is equivalent to said group being unsubstituted. When a variable group is shown to be optionally attached to a position, for example $(R^{6a})_n$ wherein n may be 0, then hydrogen may be at the position even if not recited in the variable group definition. When one or more positions on a group are said to be "not substituted" or "unsubstituted", then hydrogen atoms are attached to take up any free valency.

The term "optionally substituted" without recitation of number or identity of possible substituents (e.g., in definition of rings in $R^{1a}$) refers to groups which are unsubstituted or have at least one non-hydrogen substituent that does not extinguish the biological activity possessed by the unsubstituted analog.

Unless otherwise indicated, a "ring" or "ring system" as a component of Formula 1 (e.g., substituent Q) is carbocyclic or heterocyclic. The term "ring system" denotes two or more fused rings. The terms "bicyclic ring system" and "fused bicyclic ring system" denote a ring system consisting of two fused rings, in which either ring can be saturated, partially unsaturated, or fully unsaturated unless otherwise indicated. The term "fused heterobicyclic ring system" denotes a fused bicyclic ring system in which at least one ring atom is not carbon. A "bridged bicyclic ring system" is formed by bonding a segment of one or more atoms to nonadjacent ring members of a ring. The term "ring member" refers to an atom or other moiety (e.g., $C(=O)$, $C(=S)$, $S(O)$ or $S(O)_2$) forming the backbone of a ring or ring system.

The term "ring member" refers to an atom (e.g., C, O, N or S) or other moiety (e.g., $C(=O)$, $C(=S)$, $SiR^{10}R^{11}$ or $S(=O)_s(=NR^{17})_p$) forming the backbone of a ring or ring system. The term "aromatic" indicates that each of ring atom is essentially in the same plane and has a p-orbital perpendicular to the ring plane, and that (4n+2) π electrons, where n is a positive integer, are associated with the ring to comply with Hückel's rule The terms "carbocyclic ring", "carbocycle" or "carbocyclic ring system" denote a ring or ring system wherein the atoms forming the ring backbone are selected only from carbon. Unless otherwise indicated, a carbocyclic ring can be a saturated, partially unsaturated, or fully unsaturated ring. When a fully unsaturated carbocyclic ring satisfies Hückel's rule, then said ring is also called an "aromatic ring". "Saturated carbocyclic" refers to a ring having a backbone consisting of carbon atoms linked to one another by single bonds; unless otherwise specified, the remaining carbon valences are occupied by hydrogen atoms.

The terms "heterocyclic ring", "heterocycle" or "heterocyclic ring system" denote a ring or ring system in which at least one atom forming the ring backbone is not carbon, e.g., nitrogen, oxygen or sulfur. Typically a heterocyclic ring contains no more than 4 nitrogens, no more than 2 oxygens and no more than 2 sulfurs. Unless otherwise indicated, a heterocyclic ring can be a saturated, partially unsaturated, or fully unsaturated ring. When a fully unsaturated heterocyclic ring satisfies Hückel's rule, then said ring is also called a "heteroaromatic ring" or "aromatic heterocyclic ring". Unless otherwise indicated, heterocyclic rings and ring systems can be attached through any available carbon or nitrogen by replacement of a hydrogen on said carbon or nitrogen.

"Aromatic" indicates that each of the ring atoms is essentially in the same plane and has a p-orbital perpendicular to the ring plane, and that (4n+2) π electrons, where n is a positive integer, are associated with the ring to comply with Hückel's rule. The term "aromatic ring system" denotes a carbocyclic or heterocyclic ring system in which at least one ring of the ring system is aromatic. The term "aromatic carbocyclic ring system" denotes a carbocyclic ring system in which at least one ring of the ring system is aromatic. The term "aromatic heterocyclic ring system" denotes a heterocyclic ring system in which at least one ring of the ring system is aromatic. The term "nonaromatic ring system" denotes a carbocyclic or heterocyclic ring system that may be fully saturated, as well as partially or fully unsaturated, provided that none of the rings in the ring system are aromatic. The term "nonaromatic carbocyclic ring system" in which no ring in the ring system is aromatic. The term "nonaromatic heterocyclic ring system" denotes a heterocyclic ring system in which no ring in the ring system is aromatic.

As used herein, the term "partially unsaturated ring" or "partially unsaturated heterocycle" refers to a ring which contains unsaturated ring atoms and one or more double bonds but which is not aromatic, for example a 4,5-dihydro-1H-pyrazol-1-yl ring.

Unless otherwise indicated, heterocyclic rings and ring systems are attached to the remainder of Formula 1 through any available carbon or nitrogen atom by replacement of a hydrogen on said carbon or nitrogen atom.

The wavy bond between the nitrogen atom and the atom represented by $A^1$ in Formula 1, and in other rings depicted in the present description, indicates a single bond and the geometry about the adjacent double (i.e. the bond linking the nitrogen atom to the substituents $R^2$ and $R^3$) is either cis-(E), trans-(Z), or a mixture thereof.

As noted above, $R^2$ and $R^3$ may be taken together with the carbon atom to which they are attached to form a 3- to 7-membered ring. This 3- to 7-membered ring includes as a ring member the carbon atom to which the substituents $R^2$ and $R^3$ are attached. The other 2 to 6 ring members are selected from carbon atoms and up to 4 heteroatoms independently selected from up to 2 O, up to 2 S, up to 2 N and up to 2 Si atoms. In this definition the heteroatoms are optional, because the number of heteroatom ring members may be zero. When no heteroatom ring members are present, the ring is carbocyclic. If at least one heteroatom ring member is present, the ring is heterocyclic. The ring is optionally substituted with up to 4 substituents independently selected from halogen, cyano, $C_1$-$C_2$ alkyl, $C_1$-$C_2$ haloalkyl, $C_1$-$C_2$ alkoxy and $C_1$-$C_2$ haloalkoxy on carbon atom ring members and cyano, $C_1$-$C_2$ alkyl and $C_1$-$C_2$ alkoxy on nitrogen atom ring members. The nitrogen atom ring members may be oxidized as N-oxides, because compounds relating to Formula 1 also include N-oxide derivatives.

As noted above, $R^3$ and $R^7$ may be taken together with the linking atoms to which they are attached to form a 5- to 7-membered partially unsaturated ring. The linking atoms are the carbon atom to which $R^3$ is directly attached, the nitrogen atom to which $R^7$ is directly attached (only present when $A^1$ is —N($R^7$)—) and the intervening nitrogen atom depicted as "=N~" in Formula 1 (see E-2). Thus, the three linking atoms are "—C=N~N($R^7$)—". The linking atoms provide 3 ring members of the 5- to 7-membered ring. The other 2 to 4 ring members of the ring are provided by the $R^3$ and $R^7$ substituents. These other ring members are selected from carbon atoms and up to 3 heteroatoms independently selected from up to 1 O, up to 1 S and up to 1 N atom. In this definition the ring members selected from up to 1 O, up to 1 S and up to 1 N atom are optional, because the number of heteroatom ring members may be zero. The ring is optionally substituted with up to 3 substituents independently selected from halogen, cyano, nitro, $C_1$-$C_2$ alkyl, $C_1$-$C_2$ haloalkyl, $C_1$-$C_2$ alkoxy and $C_1$-$C_2$ haloalkoxy on carbon atom ring members and cyano, $C_1$-$C_2$ alkyl and $C_1$-$C_2$ alkoxy on nitrogen atom ring members. These optional substituents (when present) are attached to available carbon and nitrogen atom ring members in the portion of the ring provided by $R^3$ and $R^7$, and are in addition to $R^2$ and the remainder of Formula 1 attached to the ring. The nitrogen atom ring members may be oxidized as N-oxides, because compounds relating to Formula 1 also include N-oxide derivatives.

As noted above, Q is, among others, a 3- to 7-membered nonaromatic carbocyclic ring, a 5- to 7-membered nonaromatic heterocyclic ring or an 8- to 11-membered heteroaromatic bicyclic ring system, each ring or ring system containing ring members selected from carbon atoms and up to 4 heteroatoms independently selected from up to 2 O, up to 2 S, up to 4 N and up to 2 Si atoms, wherein up to 3 carbon atom ring members are independently selected from C(=O) and C(=S), the sulfur atom ring members are independently selected from $S(=O)_s(=NR^{17})_f$, and the silicon atom ring members are independently selected from $SiR^{10}R^{11}$, each ring or ring system optionally substituted with up to 5 substituents independently selected from $R^{9a}$ on carbon atom ring members and $R^{9b}$ on nitrogen atom ring members. In this definition the ring members selected from up to 2 O, up to 2 S, up to 4 N and up to 2 Si atoms are optional, because the number of heteroatom ring members may be zero. When no heteroatom ring members are present, the ring or ring system is carbocyclic. If at least one heteroatom ring member is present, the ring or ring system is heterocyclic. The definition of $S(=O)_s(=NR^{17})_f$ allows up to 2 sulfur ring members, which can be oxidized sulfur moieties (e.g., S(=O) or $S(=O)_2$) or unoxidized sulfur atoms (i.e. when s and f are both zero). The nitrogen atom ring members may be oxidized as N-oxides, because compounds relating to Formula 1 also include N-oxide derivatives. The up to 3 carbon atom ring members selected from C(=O) and C(=S) are in addition to the up to 4 heteroatoms selected from up to 2 O, up to 2 S, up to 4 N and up to 2 Si atoms.

As noted above, $R^{9a}$ is, among others, a 3- to 7-membered nonaromatic ring, containing ring members selected from carbon atoms and up to 4 heteroatoms independently selected from up to 2 O, up to 2 S and up to 4 N, wherein up to 3 carbon atom ring members are independently selected from C(=O) and C(=S), the ring optionally substituted with up to 3 substituents independently selected from halogen, cyano, $C_1$-$C_2$ alkyl, $C_1$-$C_2$ haloalkyl, $C_1$-$C_2$ alkoxy and $C_1$-$C_2$ haloalkoxy on carbon atom ring members and cyano, $C_1$-$C_2$ alkyl and $C_1$-$C_2$ alkoxy on nitrogen atom ring members. In this definition the ring members selected from up to 2 O, up to 2 S and up to 4 N atoms are optional, because the number of heteroatom ring members may be zero. The nitrogen atom ring members may be oxidized as N-oxides, because compounds relating to Formula 1 also include N-oxide derivatives. The up to 2 carbon atom ring members selected from C(=O) and C(=S) are in addition to the up to 4 heteroatoms selected from up to 2 O, up to 2 S and up to 4 N. The optional substituents (when present) are attached to available carbon and nitrogen atom ring members.

Compounds of this invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds of the invention may be present as a mixture of stereoisomers, individual stereoisomers or as an optically active form. Compounds of Formula 1 can comprise one or more chiral centers by virtue of their substituents and other molecular constituents (for example X, Q or Z) containing chiral centers. This invention comprises racemic mixtures as well as enriched and essentially pure stereoconfigurations at all possible chiral centers.

Compounds of this invention can exist as one or more conformational isomers due to restricted rotation about the amide bond (e.g., C(=W)—N) in Formula 1. This invention comprises mixtures of conformational isomers. In addition, this invention includes compounds that are enriched in one conformer relative to others.

One skilled in the art recognizes that compounds of Formula 1 can exist in equilibrium with one or more of its respective tautomeric counterparts. Unless otherwise indicated, reference to a compound by one tautomer description is to be considered to include all tautomers. For example, in Formula 1 when E is E-2 and $R^3$ is hydroxy, then reference to the tautomeric form depicted by Formula $1^1$ also includes the tautomic form depicted by Formula $1^2$.

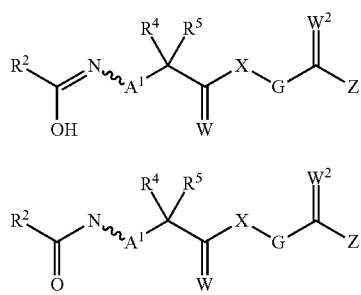

One skilled in the art would also recognize that compounds of Formula 1 can exist as two geometric stereoisomers, a syn isomer and an anti isomer at $W^2$ which is defined to be an oxime, hydrazone or cyanoimine. Unless explicitly stated, reference to a compound by one geometric steroisomer is to be considered to include either syn or anti or a mixture of both. For example, in Formula 1 when $W^2$ is $NOR^{12}$, then the geometric steroisomers can be depicted by Formula $1^3$ through Formula $1^5$.

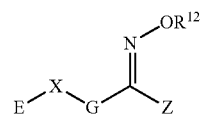

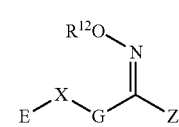

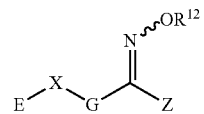

One skilled in the art would also recognize that some compounds of Formula 1 can exist as two configurational isomers, a cis isomer and a trans isomer at Z, when Z is defined to contain an alkene functional group. Unless explicitly stated, reference to a compound by one configurational isomer is to be considered to include either cis or trans or a mixture of both. For example, in Formula 1 when Z is CH=CH, then the configurational isomers can be depicted by Formula $1^6$ through Formula $1^8$.

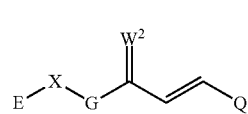

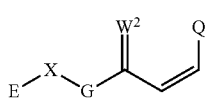

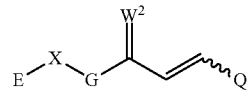

This invention is considered to include all geometric isomers, stereoisomers, configurational isomers and tautomers of Formulae 1 and 1A.

Additionally, some of the unsaturated rings and ring systems depicted in Exhibits 1, 2, 3, 4, 5, 6 and 7 can have an arrangement of single and double bonds between ring members different from that depicted. Such differing arrangements of bonds for a particular arrangement of ring atoms correspond to different tautomers. For these unsaturated rings and ring systems, the particular tautomer depicted is to be considered representative of all the tautomers possible for the arrangement of ring atoms shown.

One skilled in the art will appreciate that not all nitrogen containing heterocycles can form N-oxides since the nitrogen requires an available lone pair for oxidation to the oxide; one skilled in the art will recognize those nitrogen-containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethyldioxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, vol. 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry*, vol. 9, pp 285-291, A. R. Katritzky and A. J. Boulton, Eds., Academic Press; and G. W. H. Cheeseman and E. S. G. Werstiuk in *Advances in Heterocyclic Chemistry*, vol. 22, pp 390-392, A. R. Katritzky and A. J. Boulton, Eds., Academic Press.

One skilled in the art recognizes that because in the environment and under physiological conditions salts of chemical compounds are in equilibrium with their corresponding nonsalt forms, salts share the biological utility of the nonsalt forms. Thus a wide variety of salts of the compounds of Formula 1 are useful for control of plant diseases caused by fungal plant pathogens (i.e. are agriculturally suitable). The salts of the compounds of Formula 1 include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. When a compound of Formula 1 contains an acidic moiety such as a carboxylic acid or phenol, salts also include those formed with organic or inorganic bases such as pyridine, triethylamine or ammonia, or amides, hydrides, hydroxides or carbonates of sodium, potassium, lithium, calcium, magnesium or barium. Accordingly, the present invention comprises compounds selected from Formula 1, N-oxides and agriculturally suitable salts thereof.

Compounds selected from Formula 1, stereoisomers, tautomers, N-oxides, and salts thereof, typically exist in more than one form, and Formula 1 thus includes all crystalline and non-crystalline forms of the compounds that Formula 1 represents. Non-crystalline forms include embodiments which are solids such as waxes and gums as well as embodiments which are liquids such as solutions and melts. Crystalline forms include embodiments which represent essentially a single crystal type and embodiments which represent a mixture of polymorphs (i.e. different crystalline types). The term "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due the presence or absence of co-crystallized water or other molecules, which can be weakly or strongly bound in the lattice. Polymorphs can differ in such chemical, physical and biological properties as crystal shape, density, hardness, color, chemical stability, melting point, hygroscopicity, suspensibility, dissolution rate and biological availability. One skilled in the art will appreciate that a polymorph of a compound represented by Formula 1 can exhibit beneficial effects (e.g., suitability for preparation of useful formulations, improved biological performance) relative to another polymorph or a mixture of polymorphs of the same compound represented by Formula 1. Preparation and isolation of a particular polymorph of a compound represented by Formula 1 can be achieved by methods known to those skilled in the art including, for example, crystallization using selected solvents and temperatures.

Embodiments of the present invention as described in the Summary of the Invention include those described below. In the following Embodiments, Formula 1 includes geometric and stereoisomers, tautomers, N-oxides, and salts thereof, and reference to "a compound of Formula 1" includes the definitions of substituents specified in the Summary of the Invention unless further defined in the Embodiments.

Embodiment 1. A compound of Formula 1 wherein E is E-3.

Embodiment 2. A compound of Formula 1 wherein E is E-1 or E-2.

Embodiment 3. A compound of Formula 1 or Embodiment 2 wherein E is E-1.

Embodiment 4. A compound of Formula 1 or Embodiment 2 wherein E is E-2.

Embodiment 5. A compound of Formula 1 or Embodiments 2 or 3 wherein A is $CHR^{15}$ or $NR^{16}$.

Embodiment 6. A compound of Embodiment 5 wherein A is $NR^{16}$.

Embodiment 7. A compound of Embodiment 5 wherein A is $CHR^{15}$.

Embodiment 8. A compound of Formula 1 or Embodiments 2 or 4 wherein $A^1$ is —O—, —S—, —N($R^7$)—, —C($R^8$)$_2$— or —OC($R^8$)$_2$.

Embodiment 9. A compound of Embodiment 8 wherein $A^1$ is —O—, —S— or —N($R^7$)—.

Embodiment 10. A compound of Embodiment 9 wherein $A^1$ is —O— or —N($R^7$)—.

Embodiment 11. A compound of Formula 1 or any of Embodiments 2 through 10 wherein W is O.

Embodiment 12. A compound of Formula 1 or Embodiment 1 wherein $W^1$ is $OR^{18}$, $SR^{19}$ or $NR^{20}R^{21}$.

Embodiment 13. A compound of Embodiment 12 wherein $W^1$ is $OR^{18}$.

Embodiment 14. A compound of Embodiment 12 wherein $W^1$ is $SR^{19}$.

Embodiment 15. A compound of Embodiment 12 wherein $W^1$ is $NR^{20}R^{21}$.

Embodiment 16. A compound of Formula 1 or any one of Embodiments 1 through 15 wherein $R^{1a}$ and $R^{1b}$ independently are an optionally substituted phenyl, an optionally substituted naphthalenyl or an optionally substituted 5- to 6-membered heteroaromatic ring; or cyano, $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl, $C_2$-$C_8$ haloalkynyl, $C_3$-$C_8$ cycloalkyl, $C_2$-$C_8$ alkoxyalkyl, $C_2$-$C_8$ haloalkoxyalkyl, $C_2$-$C_8$ alkylthioalkyl, $C_2$-$C_8$ haloalkylthioalkyl, $C_2$-$C_8$ alkylsulfinylalkyl, $C_2$-$C_8$ alkylsulfonylalkyl, $C_3$-$C_8$ alkoxycarbonylalkyl, $C_3$-$C_8$ haloalkoxycarbonylalkyl, $C_2$-$C_8$ alkylaminoalkyl, $C_3$-$C_{10}$ dialkylaminoalkyl, $C_2$-$C_8$ haloalkylaminoalkyl, $C_4$-$C_{10}$ cycloalkylaminoalkyl, $C_1$-$C_8$ alkoxy, $C_1$-$C_8$ haloalkoxy, $C_3$-$C_8$ cycloalkoxy, $C_3$-$C_8$ halocycloalkoxy, $C_4$-$C_{10}$ cycloalkylalkoxy, $C_2$-$C_8$ alkenyloxy, $C_2$-$C_8$ haloalkenyloxy, $C_2$-$C_8$ alkynyloxy, $C_3$-$C_8$ haloalkynyloxy, $C_2$-$C_8$ alkoxyalkoxy, $C_2$-$C_8$ alkylcarbonyloxy, $C_2$-$C_8$ haloalkylcarbonyloxy, $C_1$-$C_8$ alkylthio, $C_1$-$C_8$ haloalkylthio, $C_3$-$C_8$ cycloalkylthio, $C_3$-$C_{10}$ trialkylsilyl, $C_1$-$C_8$ alkylamino, $C_2$-$C_8$ dialkylamino, $C_2$-$C_8$ alkylcarbonylamino, pyrrolidinyl, piperidinyl or morpholinyl.

Embodiment 17. A compound of Embodiment 16 wherein independently when $R^{1a}$, and $R^{1b}$ are other than optionally substituted phenyl, optionally substituted naphthalenyl or an optionally substituted 5- or 6-membered heteroaromatic ring then $R^{1a}$ and $R^{1b}$ are independently cyano, $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl, $C_2$-$C_8$ haloalkynyl, $C_3$-$C_8$ cycloalkyl, $C_2$-$C_8$ alkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylaminoalkyl, $C_3$-$C_{10}$ dialkylaminoalkyl, $C_1$-$C_8$ alkoxy, $C_1$-$C_8$ haloalkoxy, $C_1$-$C_8$ alkylthio, $C_3$-$C_{10}$ trialkylsilyl, $C_1$-$C_8$ alkylamino, $C_2$-$C_8$ dialkylamino, $C_2$-$C_8$ alkylcarbonylamino, pyrrolidinyl, piperidinyl or morpholinyl.

Embodiment 18. A compound of Embodiment 17 wherein independently when $R^{1a}$ and $R^{1b}$ are other than optionally substituted phenyl, optionally substituted naphthalenyl or an optionally substituted 5- or 6-membered heteroaromatic ring then $R^{1a}$ and $R^{1b}$ are independently $C_2$-$C_5$ alkyl, $C_2$-$C_5$ alkenyl, $C_2$-$C_5$ haloalkyl, $C_2$-$C_5$ haloalkenyl, $C_2$-$C_5$ haloalkylthioalkyl, $C_2$-$C_5$ alkoxyalkyl, $C_2$-$C_5$ haloalkoxyalkyl, $C_2$-$C_5$ alkylthioalkyl, $C_2$-$C_5$ alkylaminoalkyl, $C_2$-$C_5$ alkylcarbonyloxy, $C_2$-$C_5$ haloalkylcarbonyloxy, $C_2$-$C_5$ alkoxy, $C_2$-$C_5$ haloalkoxy, $C_2$-$C_5$ alkylthio, $C_2$-$C_5$ alkylamino or $C_2$-$C_5$ alkylcarbonylamino.

Embodiment 19. A compound of Embodiment 18 wherein independently when $R^{1a}$ and $R^{1b}$ are other than optionally substituted phenyl, optionally substituted naphthalenyl or an optionally substituted 5- or 6-membered heteroaromatic ring then $R^{1a}$ and $R^{1b}$ are independently $C_3$-$C_5$ alkyl, $C_3$-$C_5$ alkenyl, $C_3$-$C_5$ haloalkyl, $C_3$-$C_5$ haloalkenyl, $C_2$-$C_4$ haloalkylthioalkyl, $C_2$-$C_4$ alkoxyalkyl, $C_2$-$C_4$ haloalkoxyalkyl, $C_2$-$C_4$ alkylthioalkyl, $C_2$-$C_4$ alkylaminoalkyl, $C_2$-$C_3$ alkylcarbonyloxy, $C_2$-$C_3$ haloalkylcarbonyloxy, $C_2$-$C_4$ alkoxy, $C_2$-$C_4$ haloalkoxy, $C_2$-$C_4$ alkylthio, $C_2$-$C_4$ alkylamino or $C_2$-$C_3$ alkylcarbonylamino.

Embodiment 20. A compound of Embodiment 19 wherein independently when $R^{1a}$ and $R^{1b}$ are other than optionally substituted phenyl, optionally substituted naphthalenyl or an optionally substituted 5- or 6-membered heteroaromatic ring then $R^{1a}$ and $R^{1b}$ are independently $C_3$-$C_5$ haloalkyl, $C_3$-$C_5$ haloalkenyl, $C_3$-$C_5$ haloalkylthioalkyl, $C_3$-$C_5$ haloalkoxyalkyl, $C_2$-$C_3$ haloalkylcarbonyloxy or $C_2$-$C_4$ haloalkoxy.

Embodiment 21. A compound of Embodiment 20 wherein independently when $R^{1a}$ and $R^{1b}$ are other than optionally substituted phenyl, optionally substituted naphthalenyl or an optionally substituted 5- or 6-membered heteroaromatic ring then $R^{1a}$ and $R^{1b}$ are independently $C_4$ haloalkyl, $C_4$ haloalkenyl, $C_3$ haloalkoxyalkyl or $C_3$ haloalkoxy.

Embodiment 22. A compound of Formula 1 or any one of Embodiments 1 through 21 wherein independently when $R^{1a}$ and $R^{1b}$ are optionally substituted phenyl, optionally substituted naphthalenyl or an optionally substituted 5- or 6-membered heteroaromatic ring, the optionally substituted phenyl, optionally substituted naphthalenyl or optionally substituted 5- or 6-membered heteroaromatic ring is optionally substituted with up to 3 independently selected substituents.

Embodiment 23. A compound of Embodiment 22 wherein independently when $R^{1a}$ and $R^{1b}$ are optionally substituted phenyl, optionally substituted naphthalenyl or an optionally substituted 5- or 6-membered heteroaromatic ring, the optionally substituted phenyl, optionally substituted naphthalenyl or optionally substituted 5- or 6-membered heteroaromatic ring is optionally substituted with up to 2 independently selected substituents.

Embodiment 24. A compound of Formula 1 or any one of Embodiments 1 through 23 wherein independently when $R^{1a}$ and $R^{1b}$ are optionally substituted phenyl, optionally substituted naphthalenyl or an optionally substituted 5- or 6-membered heteroaromatic ring, then the optional substituents on the phenyl, naphthalenyl or 5- or 6-membered heteroaromatic ring are independently selected from $R^{33a}$ on carbon ring members and $R^{33b}$ on nitrogen ring members;

each $R^{33a}$ is independently halogen, cyano, hydroxy, amino, nitro, $C_1$-$C_6$ alkyl, $C_2$-$C_6$ alkenyl, $C_2$-$C_6$ alkynyl, $C_3$-$C_6$ cycloalkyl, $C_4$-$C_{10}$ cycloalkylalkyl, $C_4$-$C_{10}$ alkylcycloalkyl, $C_5$-$C_{10}$ alkylcycloalkylalkyl, $C_1$-$C_6$ haloalkyl, $C_2$-$C_6$ haloalkenyl, $C_2$-$C_6$ haloalkynyl, $C_3$-$C_6$ halocycloalkyl, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_1$-$C_4$ hydroxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl or $C_3$-$C_6$ trialkylsilyl; and each $R^{33b}$ is independently $C_1$-$C_6$ alkyl, $C_3$-$C_6$ alkenyl, $C_3$-$C_6$ alkynyl, $C_3$-$C_6$ cycloalkyl, $C_1$-$C_6$ haloalkyl, $C_3$-$C_6$ haloalkenyl, $C_3$-$C_6$ haloalkynyl, $C_3$-$C_6$ halocycloalkyl or $C_2$-$C_4$ alkoxyalkyl.

Embodiment 25. A compound of Embodiment 24 wherein independently $R^{1a}$ and $R^{1b}$ are selected from U-1 through U-50 depicted in Exhibit 1;

Exhibit 1

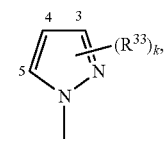

U-1

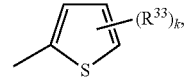

U-2

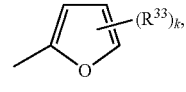

U-3

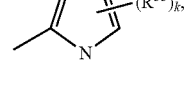

U-4

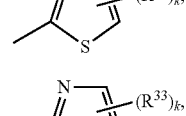

U-5

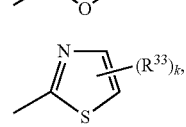

U-6

U-7

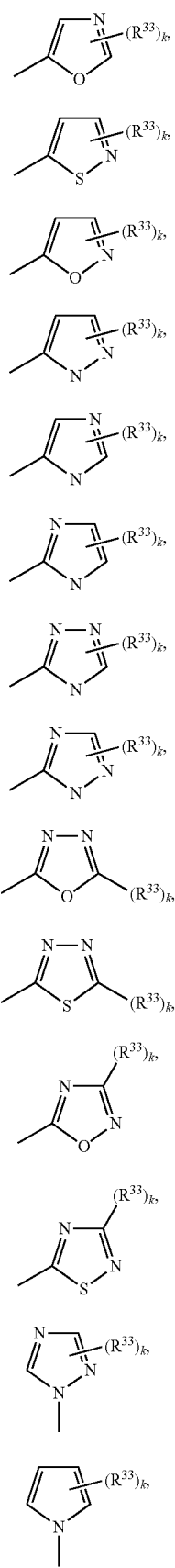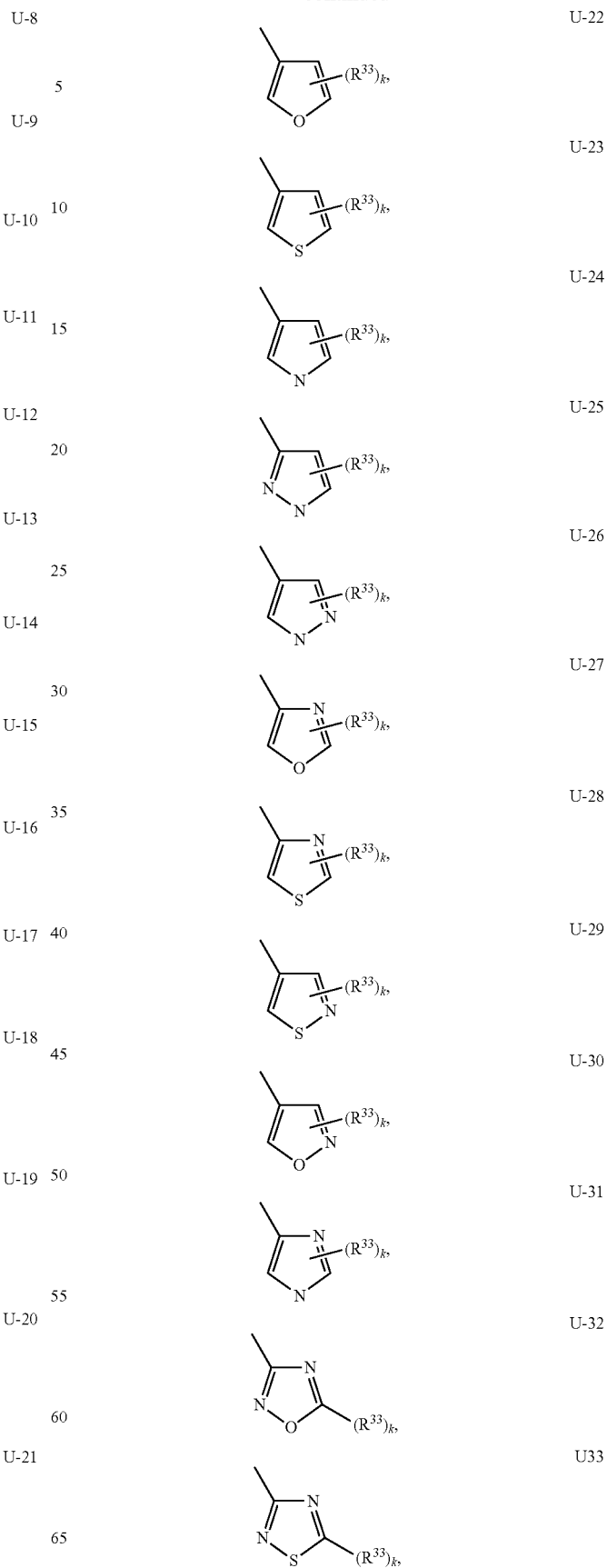

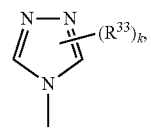 U-34

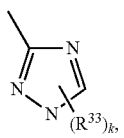 U-35

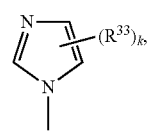 U-36

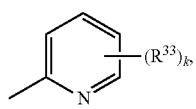 U-37

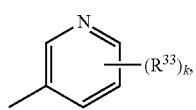 U-38

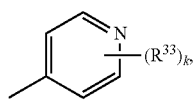 U-39

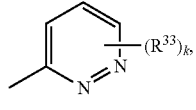 U-40

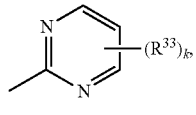 U-41

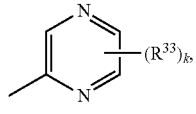 U-42

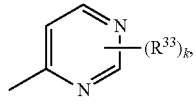 U-43

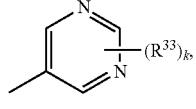 U-44

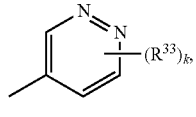 U-45

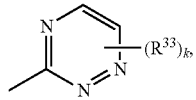 U-46

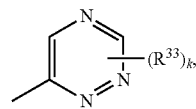 U-47

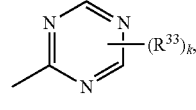 U-48

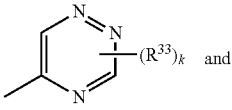 U-49 and

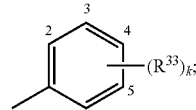 U-50 wherein when $R^{33}$ is attached to a carbon ring member, said $R^{33}$ is selected from $R^{33a}$, and when $R^{33}$ is attached to a nitrogen ring member (e.g., in U-4, U-11 through U-15, U-24 through U-26, U-31 or U-35), said $R^{33}$ is selected from $R^{33b}$; and k is 0, 1, 2 or 3.

Embodiment 26. A compound of Embodiment 25 wherein independently $R^{1a}$ and $R^{1b}$ are selected from U-1 through U-5, U-8, U-11, U-13, U-15, U-20 through U-28, U-31, U-36 through U-39 and U-50.

Embodiment 27. A compound of Embodiment 25 or 26 wherein independently $R^{1a}$ and $R^{1b}$ are selected from U-1 through U-3, U-5, U-8, U-11, U-13, U-20, U-22, U-23, U-25 through U-28, U-36 through U-39 and U-50.

Embodiment 28. A compound of any one of Embodiments 25 through 27 wherein independently $R^{1a}$ and $R^{1b}$ are selected from U-1 through U-3, U-11, U-13, U-20, U-22, U-23, U-36 through U-39 and U-50.

Embodiment 29. A compound of any one of Embodiments 25 through 28 wherein independently $R^{1a}$ and $R^{1b}$ are U-1, U-20 and U-50.

Embodiment 30. A compound of any one of Embodiments 25 through 29 wherein independently $R^{1a}$ and $R^{1b}$ are selected from U-1 and U-50.

Embodiment 31. A compound of any one of Embodiments 25 through 30 wherein independently wherein $R^{1a}$ and $R^{1b}$ are U-1.

Embodiment 32. A compound of any one of Embodiments 25 through 29 wherein independently $R^{1a}$ and $R^{1b}$ are U-20.

Embodiment 33. A compound of any one of Embodiments 25 through 30 wherein independently $R^{1a}$ and $R^{1b}$ are U-50.

Embodiment 34. A compound of any one of Embodiments 24 through 33 wherein each $R^{33a}$ is independently halogen, $C_1$-$C_6$ alkyl, $C_1$-$C_6$ haloalkyl or $C_2$-$C_4$ alkoxyalkyl.

Embodiment 35. A compound of Embodiment 34 wherein each $R^{33a}$ is independently halogen, $C_1$-$C_3$ alkyl, $C_1$-$C_3$ haloalkyl or $C_2$-$C_3$ alkoxyalkyl.

Embodiment 36. A compound of any one of Embodiments 24 through 35 wherein each $R^{33b}$ is independently $C_1$-$C_6$ alkyl.

Embodiment 37. A compound of Formula 1 or any one of Embodiments 2, 4 or 8 through 36 wherein $R^2$ when taken alone (i.e. not taken together with $R^3$) is H, cyano, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_2$-$C_4$ alkoxyalkyl, $C_2$-$C_4$ alkylthioalkyl, $C_2$-$C_4$ alkylcarbonyl, $C_2$-$C_4$ haloalkylcarbonyl, $C_2$-$C_4$ alkoxycarbonyl, $C_1$-$C_4$ alkoxy, $C_1$-$C_4$ haloalkoxy, $C_2$-$C_4$ alkenyloxy, $C_2$-$C_4$ haloalkenyloxy, $C_2$-$C_4$ alkynyloxy, $C_3$-$C_4$ haloalkynyloxy, $C_2$-$C_4$ alkoxyalkoxy, $C_1$-$C_4$ alkylthio, $C_1$-$C_4$ haloalkylthio, $C_1$-$C_4$ alkylamino, $C_2$-$C_4$ dialkylamino, $C_1$-$C_4$ haloalkylamino or $C_2$-$C_4$ halodialkylamino.

Embodiment 38. A compound of Embodiment 37 wherein $R^2$ when taken alone is H, cyano, $C_1$-$C_3$ alkyl, $C_2$-$C_3$ alkenyl, $C_2$-$C_3$ alkynyl, $C_1$-$C_3$ haloalkyl, $C_2$-$C_3$ haloalkenyl, $C_2$-$C_3$ haloalkynyl, $C_1$-$C_3$ alkoxy or $C_1$-$C_3$ haloalkoxy.

Embodiment 39. A compound of Embodiment 38 wherein $R^2$ when taken alone is H, $C_1$-$C_3$ alkyl or $C_1$-$C_3$ haloalkyl.

Embodiment 40. A compound of Embodiment 39 wherein $R^2$ when taken alone is H, $C_1$-$C_3$ alkyl or $C_1$-$C_3$ fluoroalkyl.

Embodiment 41. A compound of Embodiment 40 wherein $R^2$ is methyl, trifluoromethyl or $CF_3CH_2$.

Embodiment 42. A compound of Formula 1 or any one of Embodiments 2, 4 or 8 through 41 wherein $R^2$ is taken alone.

Embodiment 43. A compound of Formula 1 or any one of Embodiments 2, 4 or 8 through 42 wherein $R^3$ when taken alone (i.e. not taken together with $R^2$ or $R^7$) is H, $C_1$-$C_3$ alkyl, $C_1$-$C_3$ alkoxy or $C_1$-$C_3$ haloalkyl.

Embodiment 44. A compound of Embodiment 43 wherein $R^3$ when taken alone is H, $C_1$-$C_3$ alkyl or $C_1$-$C_3$ haloalkyl.

Embodiment 45. A compound of Embodiment 44 wherein $R^3$ when taken alone is H, $C_1$-$C_2$ alkyl or $C_1$-$C_3$ fluoroalkyl.

Embodiment 46. A compound of Embodiment 45 wherein $R^3$ is H, methyl or trifluoromethyl.

Embodiment 47. A compound of Formula 1 or any one of Embodiments 2, 4 or 8 through 46 wherein $R^3$ is taken alone.

Embodiment 48. A compound of Formula 1 or any one of Embodiments 2, 4 or 8 through 36 wherein when $R^2$ and $R^3$ are taken together with the carbon atom to which they are attached to form a ring, the ring is 3- to 6-membered and contains ring members selected from carbon atoms and up to 2 heteroatoms independently selected from up to 2 O, up to 2 S and up to 2 N, wherein up to 1 carbon atom ring member is C(=O) or C(=S) and the ring is optionally substituted with up to 3 substituents independently selected from halogen, cyano, $C_1$-$C_2$ alkyl, $C_1$-$C_2$ haloalkyl, $C_1$-$C_2$ alkoxy and $C_1$-$C_2$ haloalkoxy on carbon atom ring members and cyano, $C_1$-$C_2$ alkyl and $C_1$-$C_2$ alkoxy on nitrogen atom ring members.

Embodiment 49. A compound of Formula 1 or any one of Embodiments 2, 4 or 8 through 48 wherein $R^4$ is optionally substituted phenyl, optionally substituted naphthalenyl or an optionally substituted 5- or 6-membered heteroaromatic ring; or hydrogen, cyano, hydroxy, $C_1$-$C_3$ alkyl, $C_2$-$C_3$ alkenyl, $C_2$-$C_3$ alkynyl, $C_1$-$C_3$ haloalkyl, $C_2$-$C_3$ haloalkenyl, $C_2$-$C_3$ haloalkynyl, $C_2$-$C_3$ alkylcarbonyl, $C_2$-$C_3$ haloalkylcarbonyl, $C_1$-$C_3$ alkoxy, $C_1$-$C_3$ haloalkoxy, $C_1$-$C_3$ alkylthio, $C_1$-$C_3$ haloalkylthio, $C_2$-$C_3$ alkylcarbonyloxy or $C_2$-$C_3$ haloalkylcarbonyloxy.

Embodiment 50. A compound of Embodiment 49 wherein when $R^4$ is other than optionally substituted phenyl, optionally substituted naphthalenyl or an optionally substituted 5- or 6-membered heteroaromatic ring then $R^4$ is hydrogen, cyano, hydroxy, $C_1$-$C_3$ alkyl, $C_2$-$C_3$ alkenyl, $C_2$-$C_3$ alkynyl, $C_1$-$C_3$ haloalkyl, $C_2$-$C_3$ haloalkenyl, $C_2$-$C_3$ haloalkynyl, $C_2$-$C_3$ alkylcarbonyl, $C_2$-$C_3$ haloalkylcarbonyl, $C_1$-$C_3$ alkoxy, $C_1$-$C_3$ haloalkoxy, $C_1$-$C_3$ alkylthio, $C_1$-$C_3$ haloalkylthio, $C_2$-$C_3$ alkylcarbonyloxy or $C_2$-$C_3$ haloalkylcarbonyloxy.

Embodiment 51. A compound of Embodiment 50 wherein when $R^4$ is other than optionally substituted phenyl, optionally substituted naphthalenyl or an optionally substituted 5- or 6-membered heteroaromatic ring then $R^4$ is hydrogen, cyano, hydroxy, $C_1$-$C_3$ alkyl, $C_1$-$C_3$ haloalkyl, $C_1$-$C_3$ alkoxy, $C_1$-$C_3$ haloalkoxy, $C_1$-$C_3$ alkylthio, $C_1$-$C_3$ haloalkylthio, $C_2$-$C_3$ alkylcarbonyloxy or $C_2$-$C_3$ haloalkylcarbonyloxy.

Embodiment 52. A compound of Embodiment 51 wherein $R^4$ is hydrogen, cyano, methyl, methoxy or $CH_3C(=O)O-$.

Embodiment 53. A compound of Embodiment 52 wherein $R^4$ is hydrogen or methyl.

Embodiment 54. A compound of Embodiment 53 wherein $R^4$ is hydrogen.

Embodiment 55. A compound of Formula 1 or any one of Embodiments 2, 4 or 8 through 51 wherein when $R^4$ is optionally substituted phenyl, optionally substituted naphthalenyl or an optionally substituted 5- or 6-membered heteroaromatic ring, the optionally substituted phenyl, optionally substituted naphthalenyl or optionally substituted 5- or 6-membered heteroaromatic ring is substituted with up to 3 optional substituents.

Embodiment 56. A compound of Embodiment 55 wherein when $R^4$ is optionally substituted phenyl, optionally substituted naphthalenyl or an optionally substituted 5- or 6-membered heteroaromatic ring, the optionally substituted phenyl, optionally substituted naphthalenyl or optionally substituted 5- or 6-membered heteroaromatic ring is substituted with up to 2 optional substituents.

Embodiment 57. A compound of Formula 1 or any one of Embodiments 2, 4 or 8 through 51 when $R^4$ is optionally substituted phenyl, optionally substituted naphthalenyl or an optionally substituted 5- or 6-membered heteroaromatic ring, then the optional substituents on the phenyl, naphthalenyl or 5- or 6-membered heteroaromatic ring are independently selected from $R^{32a}$ on carbon ring members and $R^{32b}$ on nitrogen ring members;
each $R^{32a}$ is independently halogen, cyano, hydroxy, amino, nitro, $C_1$-$C_6$ alkyl, $C_2$-$C_6$ alkenyl, $C_2$-$C_6$ alkynyl, $C_3$-$C_6$ cycloalkyl, $C_4$-$C_{10}$ cycloalkylalkyl, $C_4$-$C_{10}$ alkylcycloalkyl, $C_5$-$C_{10}$ alkylcycloalkylalkyl, $C_1$-$C_6$ haloalkyl, $C_2$-$C_6$ haloalkenyl, $C_2$-$C_6$ haloalkynyl, $C_3$-$C_6$ halocycloalkyl, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_1$-$C_4$ hydroxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl or $C_3$-$C_6$ trialkylsilyl; and
each $R^{32b}$ is independently $C_1$-$C_6$ alkyl, $C_3$-$C_6$ alkenyl, $C_3$-$C_6$ alkynyl, $C_3$-$C_6$ cycloalkyl, $C_1$-$C_6$ haloalkyl, $C_3$-$C_6$ haloalkenyl, $C_3$-$C_6$ haloalkynyl, $C_3$-$C_6$ halocycloalkyl or $C_2$-$C_4$ alkoxyalkyl.

Embodiment 58. A compound of Embodiment 57 wherein each $R^{32a}$ is independently halogen, $C_1$-$C_2$ alkyl, $C_1$-$C_2$ haloalkyl or $C_1$-$C_2$ alkoxy.

Embodiment 59. A compound of Embodiment 58 wherein each $R^{32a}$ is independently Cl, Br, I, $C_1$-$C_2$ alkyl, trifluoromethyl or methoxy.

Embodiment 60. A compound of Embodiment 59 wherein each $R^{32a}$ is independently Cl, Br, $C_1$-$C_2$ alkyl or trifluoromethyl.

Embodiment 61. A compound of Formula 1 or any one of Embodiments 2, 4 or 8 through 49 wherein $R^4$ is other than optionally substituted naphthalenyl.

Embodiment 62. A compound of any one of Embodiments 57 through 61 wherein when $R^4$ is an optionally substituted 5- to 6-membered heteroaromatic ring then $R^4$ is selected from the group consisting of V-1 through V-10, and when $R^4$ is optionally substituted phenyl then $R^4$ is selected from V-11, shown below in Exhibit 2

Exhibit 2

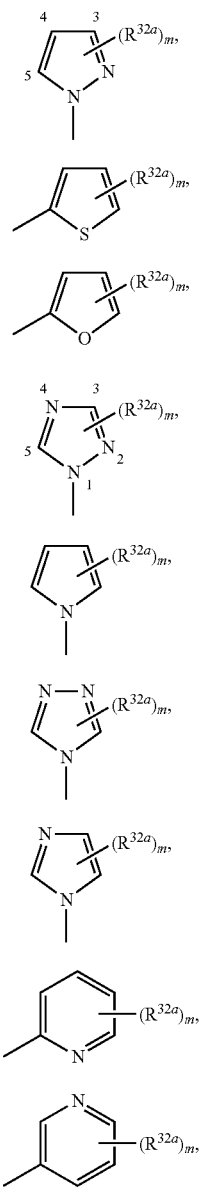

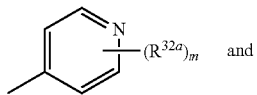

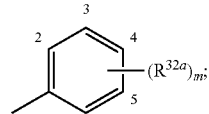

wherein m is 0, 1, 2 or 3.

Embodiment 63. A compound of Embodiment 62 wherein $R^4$ is selected from the group consisting of V-1 through V-11.

Embodiment 64. A compound of Embodiment 63 wherein $R^4$ is selected from V-1, V-4 and V-11.

Embodiment 65. A compound of Embodiment 64 wherein $R^4$ is V-1.

Embodiment 66. A compound of Formula 1 or any one of Embodiments 2, 4 or 8 through 65 wherein $R^5$ is hydrogen or $C_1$-$C_2$ alkyl.

Embodiment 67. A compound of Embodiment 66 wherein $R^5$ is hydrogen.

Embodiment 68. A compound of Formula 1 or any one of Embodiments 1 through 67 wherein X is X-1, X-2, X-3, X-4 or X-5.

Embodiment 69. A compound of Embodiment 68 wherein X is X-1, X-2 or X-3.

Embodiment 70. A compound of Embodiment 68 wherein X is X-4 or X-5.

Embodiment 71. A compound of Embodiment 69 wherein X is X-1 or X-2.

Embodiment 72. A compound of Embodiment 71 wherein X is X-2.

Embodiment 73. A compound of Embodiment 71 wherein X is X-1.

Embodiment 74. A compound of Formula 1 or any one of Embodiments 68 through 73 wherein each $R^{6a}$ is independently $C_1$-$C_2$ alkyl, $C_1$-$C_2$ haloalkyl, $C_1$-$C_2$ alkoxy, halogen, cyano or hydroxy.

Embodiment 75. A compound of Embodiment 74 wherein each $R^{6a}$ is independently methyl, methoxy, cyano or hydroxy.

Embodiment 76. A compound of Embodiment 75 wherein each $R^{6a}$ is methyl.

Embodiment 77. A compound of Formula 1 or any one of Embodiments 1 through 73 wherein n is 0 or 1.

Embodiment 78. A compound of Embodiment 77 wherein n is 0.

Embodiment 79. A compound of Formula 1 or any one of Embodiments 1 through 78 wherein each $R^{6b}$ is hydrogen, methyl or ethyl.

Embodiment 80. A compound of Embodiment 79 wherein each $R^{6b}$ is hydrogen.

Embodiment 81. A compound of Formula 1 or any one of Embodiments 1 through 80 wherein G is a 5-membered heterocyclic ring optionally substituted with up to 2 substituents independently selected from $R^{29a}$ on carbon atom ring members and $R^{30a}$ a on nitrogen atom ring members.

Embodiment 82. A compound of Formula 1 or any one of Embodiments 1 through 81 wherein G is selected from G-1 through G-48 shown in Exhibit 3
Exhibit 3
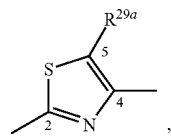
G-1
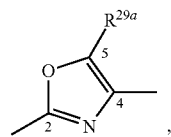
G-2
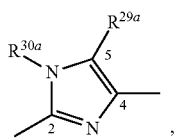
G-3
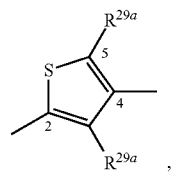
G-4
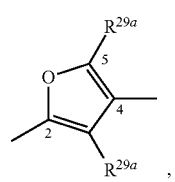
G-5
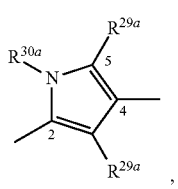
G-6
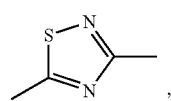
G-7
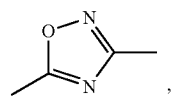
G-8
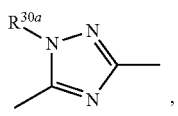
G-9
-continued
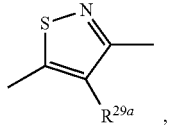
G-10
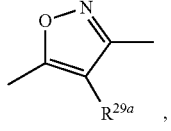
G-11
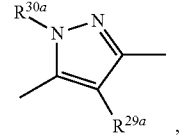
G-12
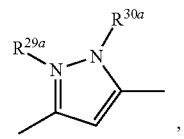
G-13
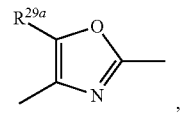
G-14
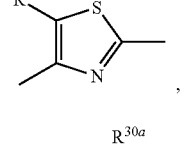
G-15
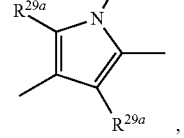
G-16
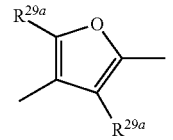
G-17
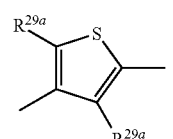
G-18
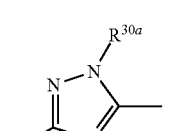
G-19
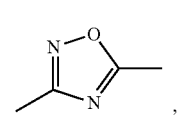
G-20

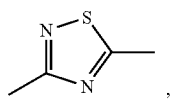, G-21
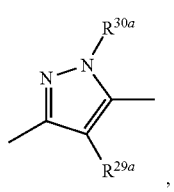, G-22
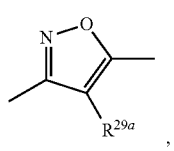, G-23
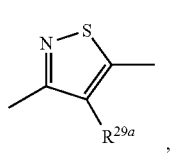, G-24
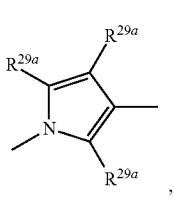, G-25
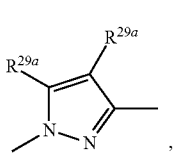, G-26
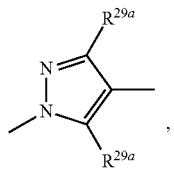, G-27
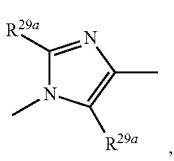, G-28
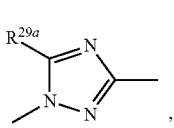, G-29
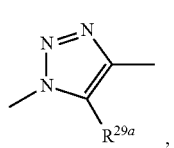, G-30
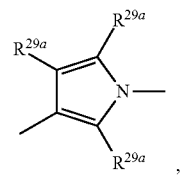, G-31
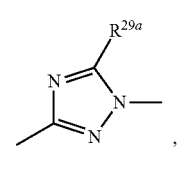, G-32
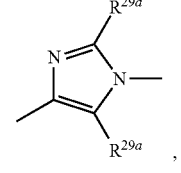, G-33
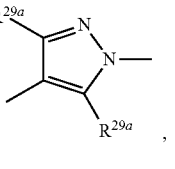, G-34
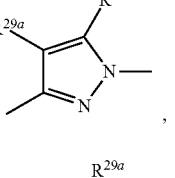, G-35
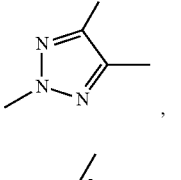, G-36
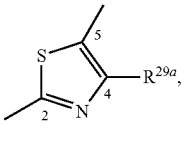, G-37
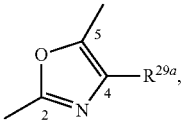, G-38
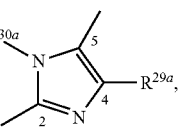, G-39
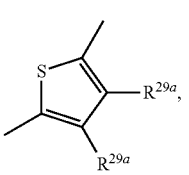, G-40

-continued

G-41

[structure: 2,5-dimethylfuran with R$^{29a}$ substituents at 3,4]

G-42

[structure: pyrrole with R$^{30a}$ on N, methyls at 2,5, R$^{29a}$ at 3,4]

G-43

[structure: imidazole with R$^{30a}$ on N, methyls, R$^{29a}$]

G-44

[structure: oxazole with methyls and R$^{29a}$]

G-45

[structure: thiazole with methyls and R$^{29a}$]

G-46

[structure: thiadiazole dimethyl]

G-47

[structure: oxadiazole dimethyl]

and

G-48

[structure: triazole with R$^{30a}$ on N, dimethyl]

wherein the bond projecting to the left is bonded to X in Formula 1, and the bond projecting to the right is bonded to C=W$^2$ in Formula 1.

Embodiment 83. A compound of Embodiment 82 wherein G is selected from G-1 through G-3, G-7, G-8, G-10, G-11, G-14, G-15, G-23, G-24, G-26 through G-28, G-30 and G-36 through G-38.

Embodiment 84. A compound of Embodiment 83 wherein G is selected from G-1, G-2, G-7, G-8, G-14, G-15, G-23, G-24, G-26, G-27, G-36, G-37 and G-38.

Embodiment 85. A compound of Embodiment 84 wherein G is selected from G-1, G-2, G-15, G-26, G-27, G-36, G-37 and G-38.

Embodiment 86. A compound of Embodiment 85 wherein G is selected from G-1, G-2, G-15, G-26, G-36 and G-37.

Embodiment 87. A compound of Embodiment 86 wherein G is G-15.

Embodiment 88. A compound of Embodiment 86 wherein G is G-2.

Embodiment 89. A compound of Embodiment 86 wherein G is G-36.

Embodiment 90. A compound of Embodiment 86 wherein G is G-26.

Embodiment 91. A compound of Embodiment 86 wherein G is G-1.

Embodiment 92. A compound of Formula 1 or any one of Embodiments 1 through 91 wherein each R$^{29a}$ is independently hydrogen, halogen or C$_1$-C$_3$ alkyl.

Embodiment 93. A compound of Embodiment 92 wherein each R$^{29a}$ is independently hydrogen or methyl.

Embodiment 94. A compound of Embodiment 93 wherein each R$^{29a}$ is hydrogen.

Embodiment 95. A compound of Formula 1 or any one of Embodiments 1 through 94 wherein each R$^{30a}$ is independently hydrogen or methyl.

Embodiment 96. A compound of Embodiment 95 wherein each R$^{30a}$ is hydrogen.

Embodiment 97. A compound of Formula 1 or any one of Embodiments 1 through 91 wherein G is a heterocyclic ring unsubstituted except for its attachments to X and C=W$^2$.

Embodiment 98. A compound of Formula 1 or any one of Embodiments 1 through 97 wherein R$^{12}$ or R$^{14}$ independently are hydrogen.

Embodiment 99. A compound of Formula 1 or any one of Embodiments 1 through 97 wherein R$^{12}$ or R$^{14}$ independently are C$_1$-C$_4$ alkyl, C$_2$-C$_4$ alkenyl, C$_2$-C$_4$ alkynyl, C$_1$-C$_4$ haloalkyl, C$_2$-C$_4$ haloalkenyl, C$_2$-C$_4$ haloalkynyl, C$_2$-C$_4$ alkoxyalkyl, C$_2$-C$_4$ alkylthioalkyl, C$_2$-C$_4$ alkylsulfinylalkyl, C$_2$-C$_4$ alkylsulfonylalkyl, C$_2$-C$_4$ alkylcarbonyl, C$_2$-C$_4$ haloalkylcarbonyl, C$_2$-C$_5$ alkoxycarbonyl, C$_2$-C$_5$ alkylaminocarbonyl, C$_3$-C$_5$ dialkylaminocarbonyl, C$_2$-C$_4$ aminocarbonylalkyl or C$_3$-C$_6$ cycloalkyl, each optionally substituted by up to one Q$^1$ and up to 2 substituents selected from C$_1$-C$_3$ alkyl, C$_1$-C$_3$ haloalkyl, C$_1$-C$_3$ alkoxy, hydroxyl and cyano.

Embodiment 100. A compound of Embodiment 99 wherein R$^{12}$ or R$^{14}$ independently are C$_1$-C$_4$ alkyl, C$_2$-C$_4$ alkenyl, C$_2$-C$_4$ alkynyl, C$_1$-C$_4$ haloalkyl, C$_2$-C$_4$ alkoxyalkyl, C$_2$-C$_4$ alkylcarbonyl, C$_2$-C$_5$ alkoxycarbonyl, C$_2$-C$_5$ alkylaminocarbonyl, C$_3$-C$_5$ dialkylaminocarbonyl, C$_2$-C$_4$ aminocarbonylalkyl or C$_3$-C$_6$ cycloalkyl, each optionally substituted by up to one Q$^1$.

Embodiment 101. A compound of Embodiment 100 wherein R$^{12}$ or R$^{14}$ independently are C$_1$-C$_2$ alkyl, C$_2$-C$_4$ alkenyl, C$_2$-C$_4$ alkynyl, C$_1$-C$_2$ haloalkyl, C$_2$-C$_4$ alkoxyalkyl, C$_2$-C$_4$ alkylcarbonyl or C$_2$-C$_5$ alkoxycarbonyl, each optionally substituted by up to one Q$^1$.

Embodiment 102. A compound of Embodiment 101 wherein R$^{12}$ or R$^{14}$ independently are CH$_3$, CF$_3$, C(=O)CH$_3$, CO$_2$Me or CO$_2$Et.

Embodiment 102a. A compound of Embodiment 101 wherein R$^{12}$ or R$^{14}$ independently are CH$_3$, C(=O)CH$_3$, CO$_2$Me or CO$_2$Et.

Embodiment 102b. A compound of Embodiment 100 wherein R$^{12}$ or R$^{14}$ independently are C$_1$-C$_2$ alkyl optionally substituted by up to one Q$^1$.

Embodiment 103. A compound of Formula 1 or any one of Embodiments 1 through 101 wherein $Q^1$ is selected from Q-1 through Q-103 depicted in Exhibit 4;
Exhibit 4
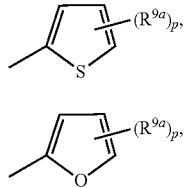 Q-1
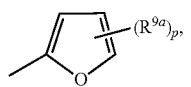 Q-2
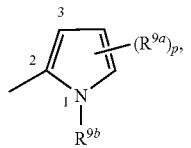 Q-3
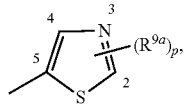 Q-4
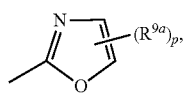 Q-5
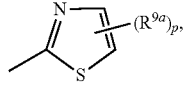 Q-6
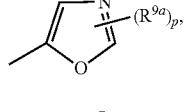 Q-7
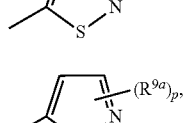 Q-8
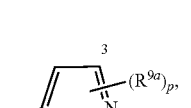 Q-9
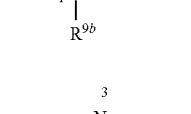 Q-10
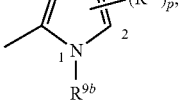 Q-11
-continued
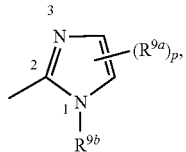 Q-12
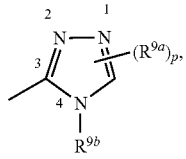 Q-13
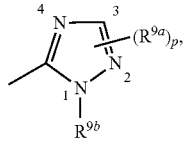 Q-14
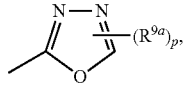 Q-15
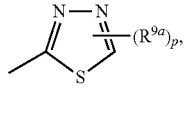 Q-16
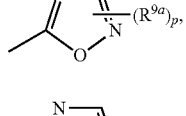 Q-17
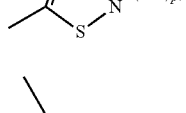 Q-18
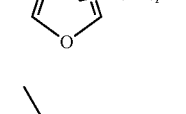 Q-19
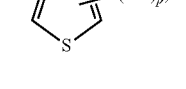 Q-20
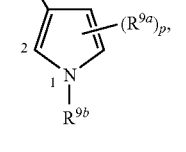 Q-21
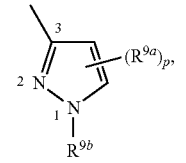 Q-22

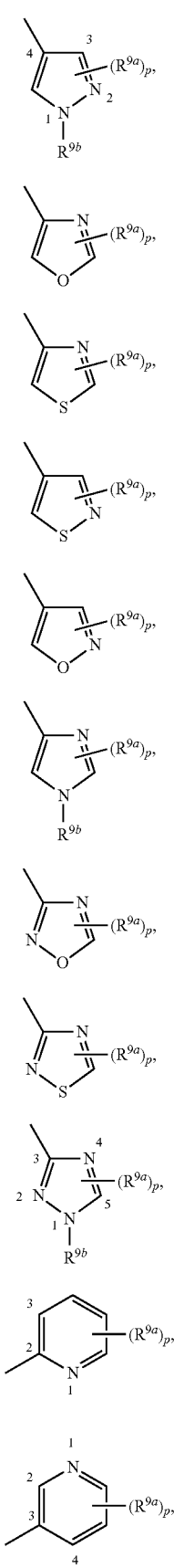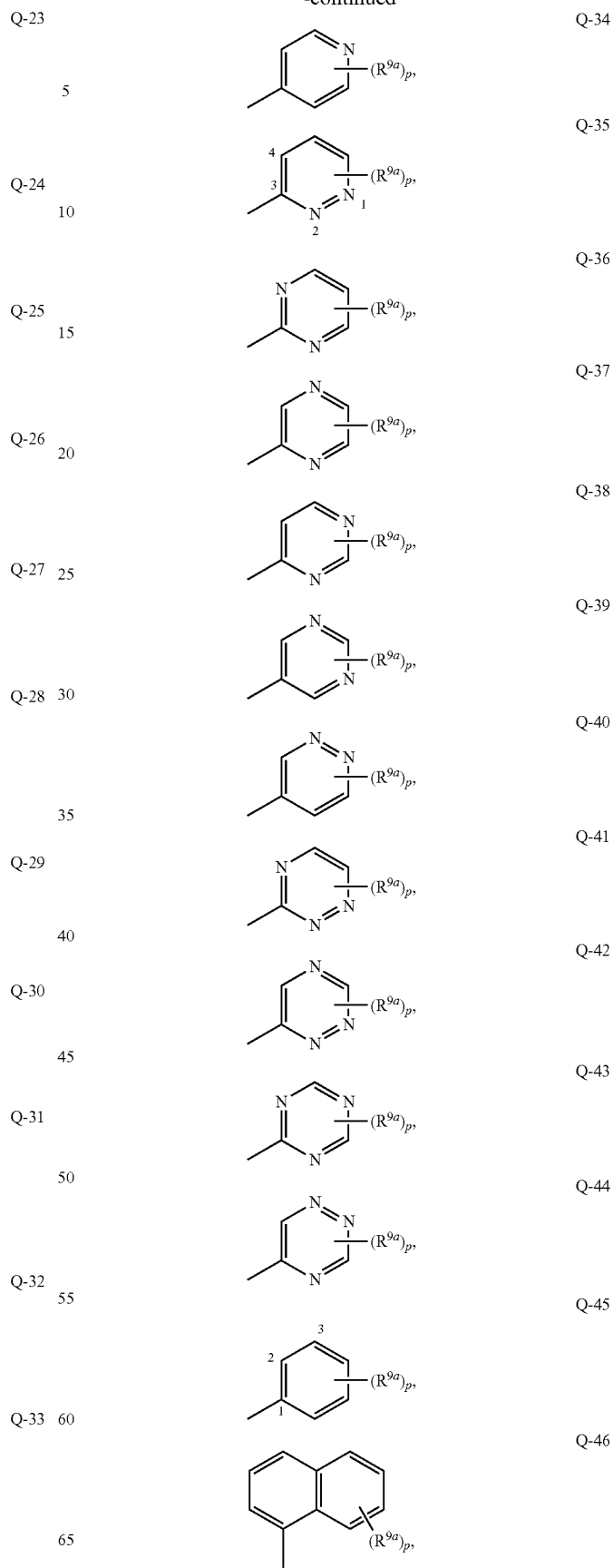

| | |
|---|---|
| 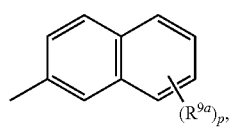 | Q-47 |
| 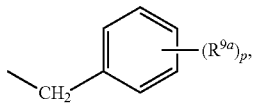 | Q-48 |
|  | Q-49 |
| 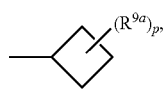 | Q-50 |
| 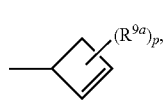 | Q-51 |
| 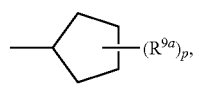 | Q-52 |
| 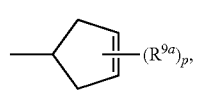 | Q-53 |
| 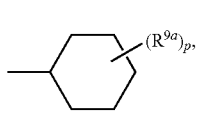 | Q-54 |
| 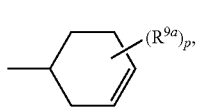 | Q-55 |
| 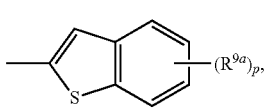 | Q-56 |
| 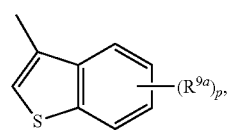 | Q-57 |
| 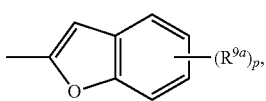 | Q-58 |
| 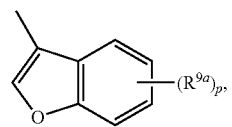 | Q-59 |
| 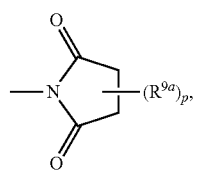 | Q-60 |
| 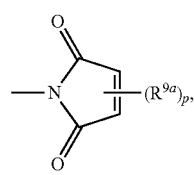 | Q-61 |
| 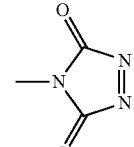 | Q-62 |
| 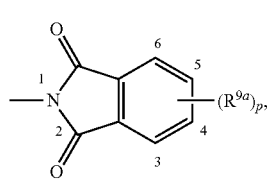 | Q-63 |
| 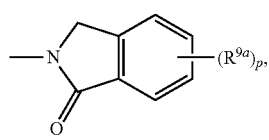 | Q-64 |
| 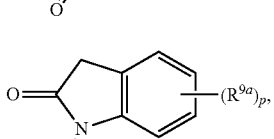 | Q-65 |
| 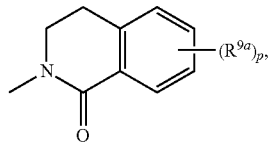 | Q-66 |
| 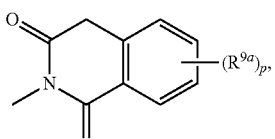 | Q-67 |
| 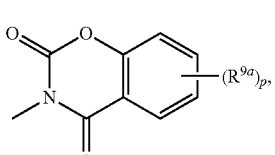 | Q-68 |
| 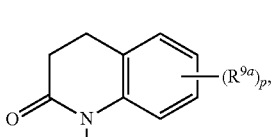 | Q-69 |
| 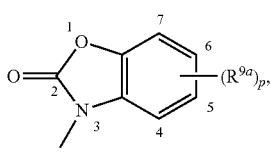 | Q-70 |

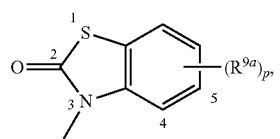 Q-71
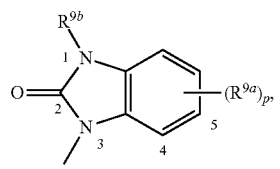 Q-72
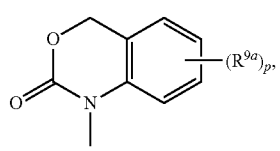 Q-73
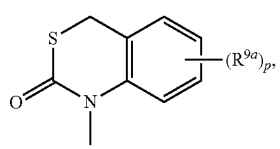 Q-74
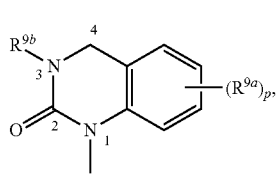 Q-75
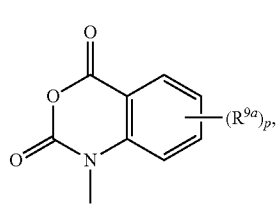 Q-76
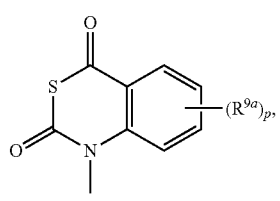 Q-77
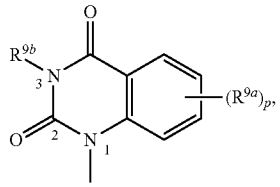 Q-78
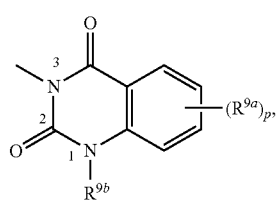 Q-79
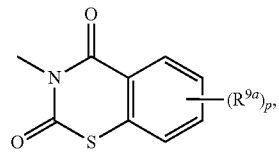 Q-80
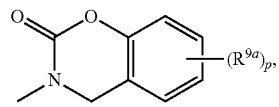 Q-81
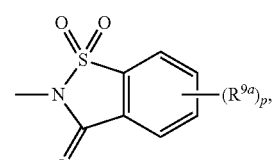 Q-82
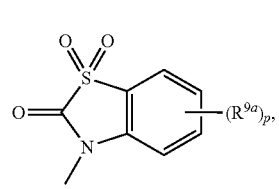 Q-83
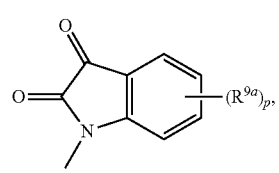 Q-84
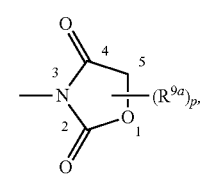 Q-85
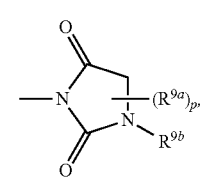 Q-86
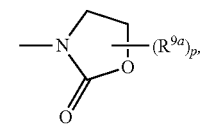 Q-87
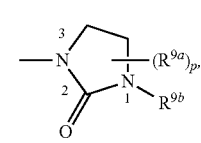 Q-88
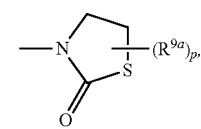 Q-89

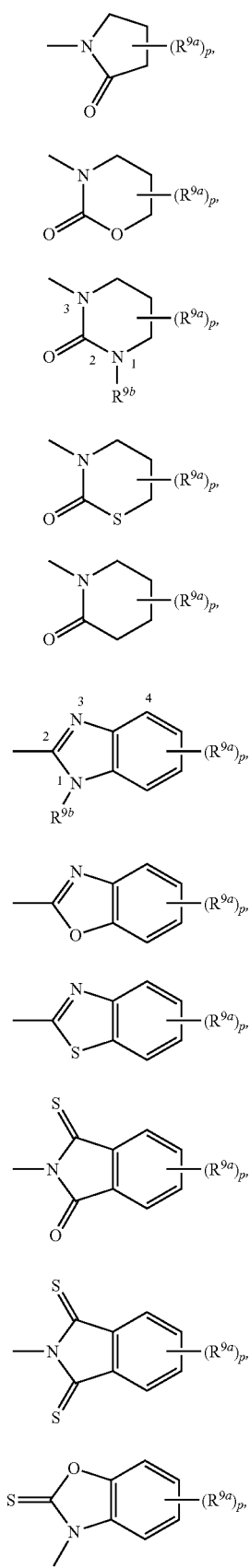
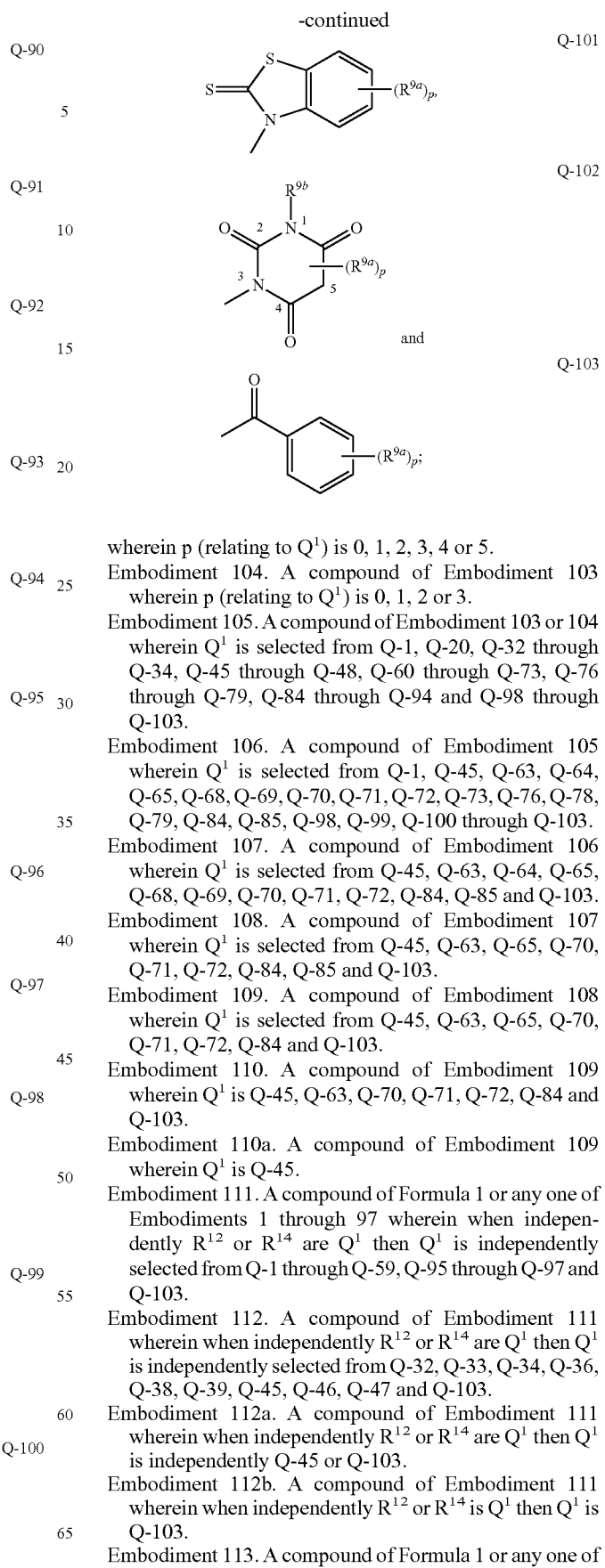

wherein p (relating to $Q^1$) is 0, 1, 2, 3, 4 or 5.

Embodiment 104. A compound of Embodiment 103 wherein p (relating to $Q^1$) is 0, 1, 2 or 3.

Embodiment 105. A compound of Embodiment 103 or 104 wherein $Q^1$ is selected from Q-1, Q-20, Q-32 through Q-34, Q-45 through Q-48, Q-60 through Q-73, Q-76 through Q-79, Q-84 through Q-94 and Q-98 through Q-103.

Embodiment 106. A compound of Embodiment 105 wherein $Q^1$ is selected from Q-1, Q-45, Q-63, Q-64, Q-65, Q-68, Q-69, Q-70, Q-71, Q-72, Q-73, Q-76, Q-78, Q-79, Q-84, Q-85, Q-98, Q-99, Q-100 through Q-103.

Embodiment 107. A compound of Embodiment 106 wherein $Q^1$ is selected from Q-45, Q-63, Q-64, Q-65, Q-68, Q-69, Q-70, Q-71, Q-72, Q-84, Q-85 and Q-103.

Embodiment 108. A compound of Embodiment 107 wherein $Q^1$ is selected from Q-45, Q-63, Q-65, Q-70, Q-71, Q-72, Q-84, Q-85 and Q-103.

Embodiment 109. A compound of Embodiment 108 wherein $Q^1$ is selected from Q-45, Q-63, Q-65, Q-70, Q-71, Q-72, Q-84 and Q-103.

Embodiment 110. A compound of Embodiment 109 wherein $Q^1$ is Q-45, Q-63, Q-70, Q-71, Q-72, Q-84 and Q-103.

Embodiment 110a. A compound of Embodiment 109 wherein $Q^1$ is Q-45.

Embodiment 111. A compound of Formula 1 or any one of Embodiments 1 through 97 wherein when independently $R^{12}$ or $R^{14}$ are $Q^1$ then $Q^1$ is independently selected from Q-1 through Q-59, Q-95 through Q-97 and Q-103.

Embodiment 112. A compound of Embodiment 111 wherein when independently $R^{12}$ or $R^{14}$ are $Q^1$ then $Q^1$ is independently selected from Q-32, Q-33, Q-34, Q-36, Q-38, Q-39, Q-45, Q-46, Q-47 and Q-103.

Embodiment 112a. A compound of Embodiment 111 wherein when independently $R^{12}$ or $R^{14}$ are $Q^1$ then $Q^1$ is independently Q-45 or Q-103.

Embodiment 112b. A compound of Embodiment 111 wherein when independently $R^{12}$ or $R^{14}$ is $Q^1$ then $Q^1$ is Q-103.

Embodiment 113. A compound of Formula 1 or any one of Embodiments 1 through 112b wherein $R^{14}$ is cyano.

Embodiment 114. A compound of Formula 1 or any one of Embodiments 1 through 113 wherein $R^{13}$ is hydrogen, $C_1$-$C_4$ alkyl or $C_1$-$C_4$ haloalkyl.

Embodiment 115. A compound of Embodiment 114 wherein $R^{13}$ is hydrogen, $CH_3$ or $CF_3$.

Embodiment 115a. A compound of Embodiment 114 wherein $R^{13}$ is hydrogen or $CH_3$.

Embodiment 116. A compound of Formula 1 and any one of Embodiments 1 through 97 wherein $W^2$ is selected from J-1 through J-50 depicted in Exhibit 5;

Exhibit 5

J-1
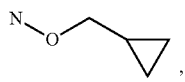

J-2
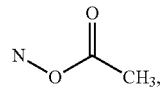

J-3
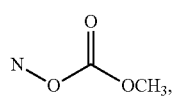

J-4
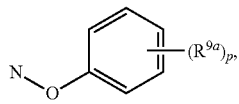

J-5
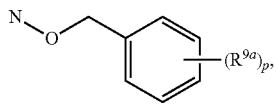

J-6
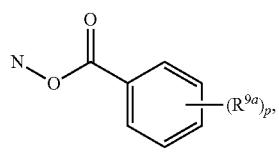

J-7
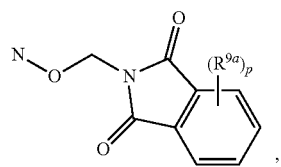

J-8

J-9
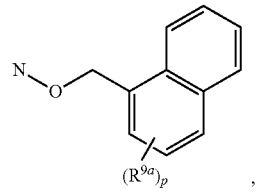

J-10
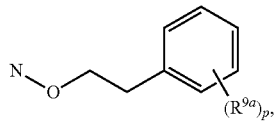

-continued

J-11
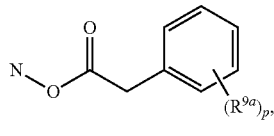

J-12
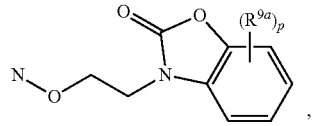

J-13
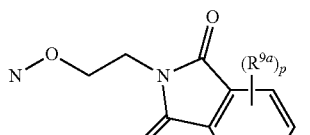

J-14
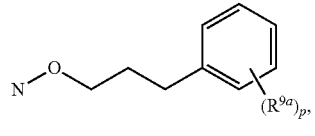

J-15
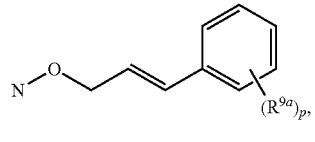

J-16
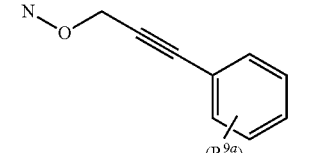

J-17
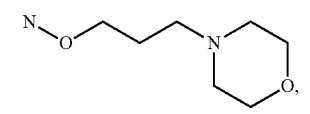

J-18
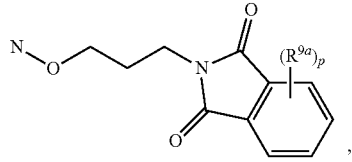

J-19
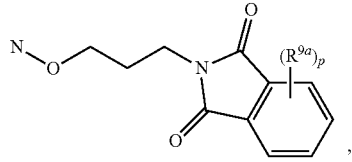

J-20

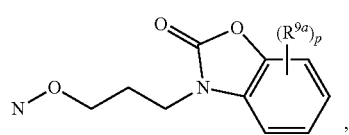 J-21
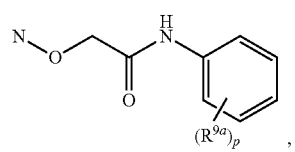 J-22
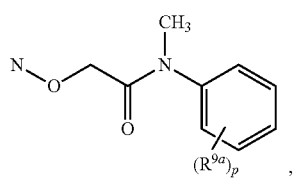 J-23
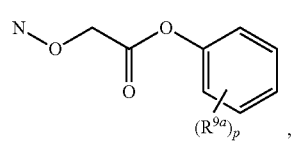 J-24
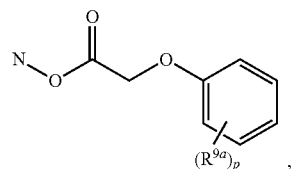 J-25
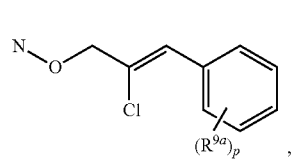 J-26
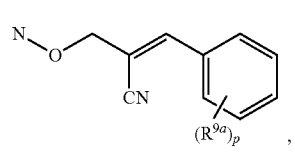 J-27
 J-28
 J-29
 J-30
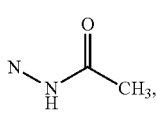 J-31
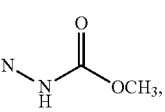 J-32
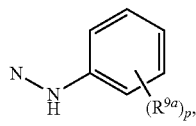 J-33
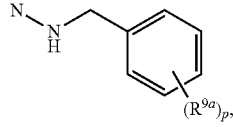 J-34
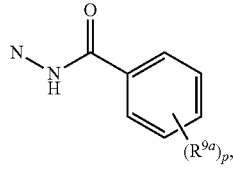 J-35
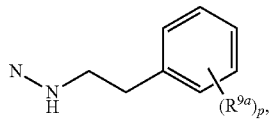 J-36
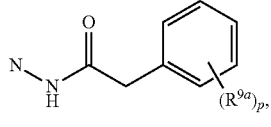 J-37
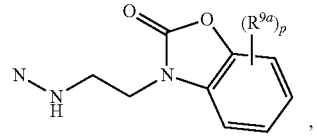 J-38
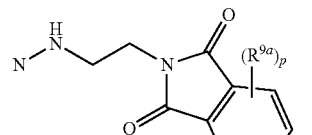 J-39
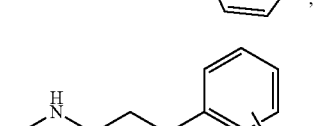 J-40
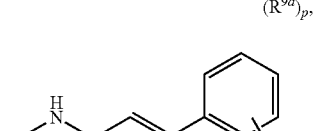 J-41
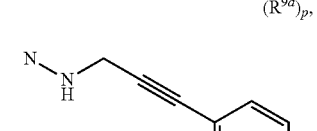 J-42
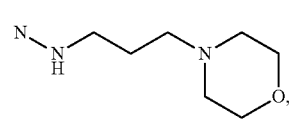 J-43

-continued

J-44

J-45

J-46

J-47

J-48

J-49

J-50 wherein p is 0, 1, 2, 3, 4 or 5.

Embodiment 117. A compound of Embodiment 116 wherein p is 0, 1, 2 or 3.

Embodiment 118. A compound of Embodiment 116 or 117 wherein $W^2$ is selected from J-1, J-2, J-4, J-5, J-7, J-8, J-9, J-10, J-12, J-13, J-14, J-15, J-16, J-19, J-20, J-21, J-23, J-26, J-28, J-29, J-30, J-31, J-32, J-34, J-35, J-36, J-37, J-38, J-39, J-43, J-44, J-45 and J-50.

Embodiment 119. A compound of Embodiment 118 wherein $W^2$ is selected from J-1, J-2, J-4, J-5, J-7, J-8, J-9, J-10, J-12, J-13, J-14, J-15, J-16, J-19, J-20, J-21, J-23 and J-26.

Embodiment 120. A compound of Embodiment 119 wherein $W^2$ is selected from J-1, J-2, J-4 and J-5.

Embodiment 121. A compound of Embodiment 120 wherein $W^2$ is selected from J-1, J-2 and J-4.

Embodiment 122. A compound of Embodiment 121 wherein $W^2$ is J-1.

Embodiment 123. A compound of Embodiment 121 wherein $W^2$ is J-2.

Embodiment 124. A compound of Embodiment 119 wherein $W^2$ is selected from J-7, J-8, J-9, J-10, J-12, J-14, J-15, J-16, J-20, J-21, J-23 and J-26.

Embodiment 124a. A compound of Embodiment 119 wherein $W^2$ is selected from J-7, J-9, J-10, J-12, J-14, J-15, J-16, J-20, J-21, J-23 and J-26.

Embodiment 125. A compound of Embodiment 124 wherein $W^2$ is selected from J-7, J-8, J-12, J-23 and J-26.

Embodiment 125a. A compound of Embodiment 124a wherein $W^2$ is selected from J-7, J-12, J-23 and J-26.

Embodiment 125b. A compound of Embodiment 124a wherein $W^2$ is J-7.

Embodiment 125c. A compound of Embodiment 124 wherein $W^2$ is J-8.

Embodiment 126. A compound of Embodiment 124 wherein $W^2$ is selected from J-9, J-10, J-14, J-15, J-16, J-20 and J-21.

Embodiment 127. A compound of Embodiment 118 wherein $W^2$ is selected from J-28, J-29, J-30, J-31, J-32, J-34, J-35, J-36, J-37, J-38, J-39, J-43, J-44, J-45 and J-50.

Embodiment 128. A compound of Embodiment 127 wherein $W^2$ is selected from J-28, J-29, J-30, J-31, J-32 and J-50.

Embodiment 129. A compound of Embodiment 128 wherein $W^2$ is selected from J-28, J-30 and J-50.

Embodiment 130. A compound of Embodiments 129 wherein $W^2$ is J-50.

Embodiment 131. A compound of Embodiment 127 wherein $W^2$ is selected from J-34, J-36, J-37, J-38 and J-39.

Embodiment 132. A compound of Formula 1 or any one of Embodiments 1 through 115 wherein $W^2$ is $NOR^{12}$.

Embodiment 133. A compound of Formula 1 or any one of Embodiments 1 through 115 wherein $W^2$ is $NNR^{13}R^{14}$.

Embodiment 134. A compound of Formula 1 or any one of Embodiments 1 through 133 wherein Z is hydrogen.

Embodiment 135. A compound of Formula 1 or any one of Embodiments 1 through 133 wherein Z is cyano.

Embodiment 136. A compound of Formula 1 or any one of Embodiments 1 through 133 wherein Z is halogen.

Embodiment 137. A compound of Formula 1 or any one of Embodiments 1 through 133 wherein Z is Q.

Embodiment 138. A compound of Formula 1 or any one of Embodiments 1 through 133 wherein Z is $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_2$-$C_4$ alkoxyalkyl, $C_2$-$C_4$ alkylthioalkyl, $C_2$-$C_4$ alkylsulfinylalkyl, $C_2$-$C_4$ alkylsulfonylalkyl, $C_2$-$C_4$ alkylcarbonyl, $C_2$-$C_4$ haloalkylcarbonyl, $C_2$-$C_5$ alkoxycarbonyl, $C_2$-$C_5$ alkylaminocarbonyl, $C_3$-$C_5$ dialkylaminocarbonyl, $C_2$-$C_4$ aminocarbonylalkyl or $C_3$-$C_6$ cycloalkyl, each optionally substituted by up to one Q and up to 2 substituents selected from $C_1$-$C_3$ alkyl, $C_1$-$C_3$ haloalkyl, $C_1$-$C_3$ alkoxy, hydroxyl and cyano.

Embodiment 139. A compound of Embodiment 138 wherein Z is $C_1$-$C_4$ alkyl, $C_2$-$C_4$ alkenyl, $C_2$-$C_4$ alkynyl, $C_1$-$C_4$ haloalkyl, $C_2$-$C_4$ alkoxyalkyl, $C_2$-$C_4$ alkylcarbonyl, $C_2$-$C_5$ alkoxycarbonyl, $C_2$-$C_5$ alkylaminocarbonyl, $C_3$-$C_5$ dialkylaminocarbonyl, $C_2$-$C_4$ aminocarbonylalkyl or $C_3$-$C_6$ cycloalkyl, each optionally substituted by up to one Q.

Embodiment 140. A compound of Embodiment 139 wherein Z is $C_1$-$C_2$ alkyl, $C_2$-$C_4$ alkenyl, $C_2$-$C_4$ alkynyl, $C_1$-$C_2$ haloalkyl, $C_2$-$C_4$ alkoxyalkyl, $C_2$-$C_4$ alkylcarbonyl or $C_2$-$C_5$ alkoxycarbonyl each optionally substituted by one Q.

Embodiment 141. A compound of Embodiment 140 wherein Z is $CH_3$, $CF_3$, $C(=O)CH_3$, $CO_2Me$ or $CO_2Et$.

Embodiment 141a. A compound of Embodiment 140 wherein Z is CH$_3$.

Embodiment 141b. A compound of Formula 1 or any one of Embodiments 1 through 133 wherein Z is CH$_3$ or hydrogen.

Embodiment 142. A compound of Formula 1 or any one of Embodiments 1 through 133 and Embodiments 137 through 140 wherein Q is selected from one of Q-1 through Q-102 depicted in Exhibit 4; and p (relating to Q) is 0, 1, 2, 3 or 4.

Embodiment 142a. A compound of Formula 1 or any one of Embodiments 1 through 133 and Embodiments 137 through 140 wherein Q is selected from one of Q-1 through Q-103 depicted in Exhibit 4; and p (relating to Q) is 0, 1, 2, 3 or 4.

Embodiment 143. A compound of Embodiment 142 wherein p (relating to Q) is 0, 1, 2 or 3.

Embodiment 144. A compound of Embodiment 142 or 143 wherein Q is selected from Q-1, Q-20, Q-32 through Q-34, Q-45 through Q-47, Q-60 through Q-73, Q-76 through Q-79, Q-84 through Q-94 and Q-98 through Q-102.

Embodiment 145. A compound of Embodiment 144 wherein Q is selected from Q-1, Q-45, Q-63, Q-64, Q-65, Q-68, Q-69, Q-70, Q-71, Q-72, Q-73, Q-76, Q-78, Q-79, Q-84, Q-85, Q-98, Q-99, Q-100, Q-101 and Q-102.

Embodiment 146. A compound of Embodiment 145 wherein Q is selected from Q-45, Q-63, Q-64, Q-65, Q-68, Q-69, Q-70, Q-71, Q-72, Q-84 and Q-85.

Embodiment 147. A compound of Embodiment 146 wherein Q is selected from Q-45, Q-63, Q-65, Q-70, Q-71, Q-72, Q-84 and Q-85.

Embodiment 148. A compound of Embodiment 147 wherein Q is Q-45.

Embodiment 149. A compound of Embodiment 142 or 143 wherein when Z is Q, then said Q is selected from Q-1 through Q-59 and Q-95 through Q-97.

Embodiment 150. A compound of Embodiment 149 wherein when Z is Q, then said Q is Q-32, Q-33, Q-34, Q-36, Q-38, Q-39, Q-45, Q-46 or Q-47.

Embodiment 151. A compound of Embodiment 150 wherein when Z is Q, then said Q is Q-45.

Embodiment 152. A compound of Formula 1 or any one of Embodiments 1 through 133 wherein Z is selected from Z-1 through Z-29 depicted in Exhibit 6;

Exhibit 6

—H,  Z-1

—CH$_3$,  Z-2

—CH$_2$CH$_3$,  Z-3

—Cl,  Z-4

—CN,  Z-5

—CF$_3$,  Z-6

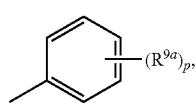  Z-7

-continued

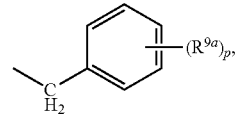  Z-8

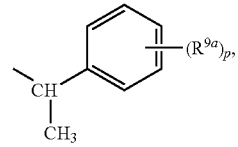  Z-9

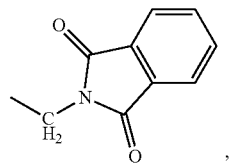  Z-10

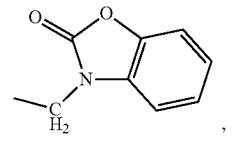  Z-11

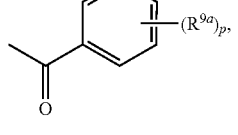  Z-12

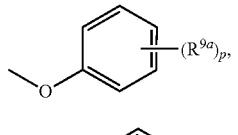  Z-13

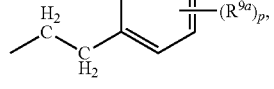  Z-14

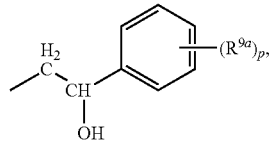  Z-15

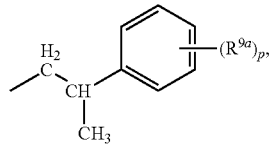  Z-16

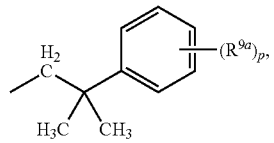  Z-17

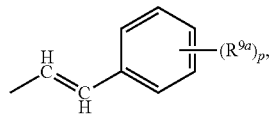  Z-18

-continued

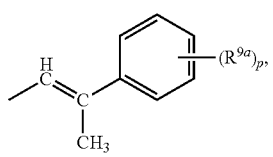 Z-19

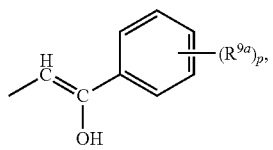 Z-20

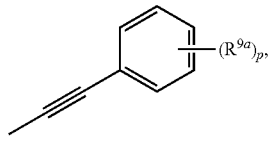 Z-21

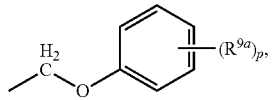 Z-22

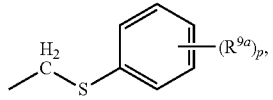 Z-23

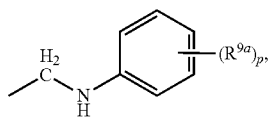 Z-24

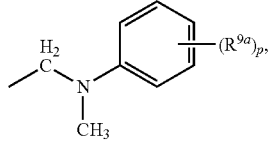 Z-25

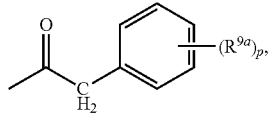 Z-26

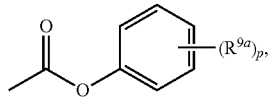 Z-27

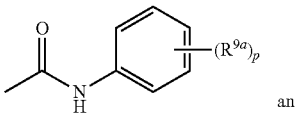 Z-28

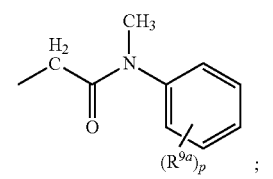 Z-29 wherein p (relating to $W^2$) is 0, 1, 2, 3, 4 or 5.

Embodiment 153. A compound of Embodiment 152 wherein p (relating to $W^2$) is 0, 1, 2 or 3.

Embodiment 154. A compound of Embodiment 152 or 153 wherein Z is selected from Z-1, Z-2, Z-4, Z-5, Z-10, Z-11, Z-14, Z-15, Z-18, Z-19 and Z-20.

Embodiment 155. A compound of Embodiment 154 wherein Z is selected from Z-1, Z-2, Z-14, Z-15 and Z-18.

Embodiment 156. A compound of Embodiment 155 wherein Z is Z-1 or Z-2.

Embodiment 157. A compound of Embodiment 156 wherein Z is Z-1.

Embodiment 158. A compound of Embodiment 156 wherein Z is Z-2.

Embodiment 159. A compound of Embodiment 155 wherein Z is selected from Z-14, Z-15 and Z-18.

Embodiment 160. A compound of Embodiment 159 wherein Z is Z-14.

Embodiment 161. A compound of Embodiment 159 wherein Z is Z-15.

Embodiment 162. A compound of Embodiment 159 wherein Z is Z-18.

Embodiment 163. A compound of Formula 1 or any one of Embodiments 1 through 162 wherein the group $C(=W^2)Z$ is selected from L-1 through L-100 depicted in Exhibit 7;

Exhibit 7

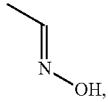 L-1

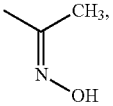 L-2

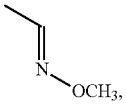 L-3

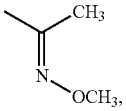 L-4

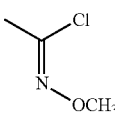 L-5

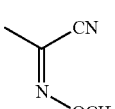 L-6

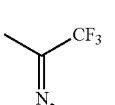 L-7

-continued
L-8
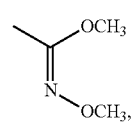
L-9
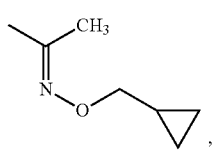
L-10
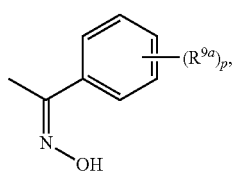
L-11
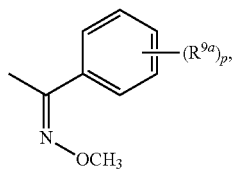
L-12
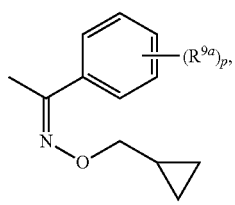
L-13
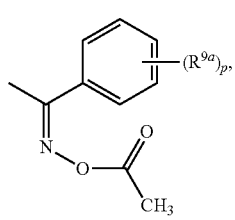
L-14
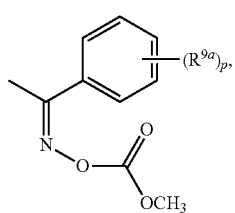
L-15
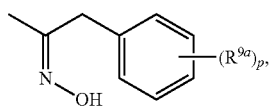
L-16
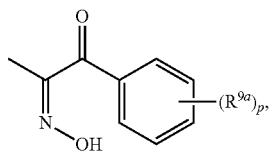
-continued
L-17
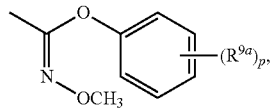
L-18
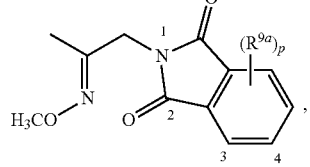
L-19
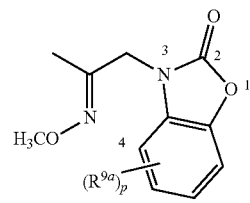
L-20
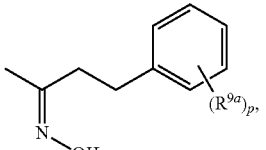
L-21
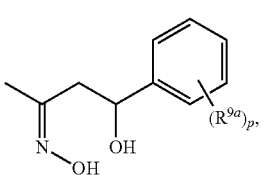
L-22
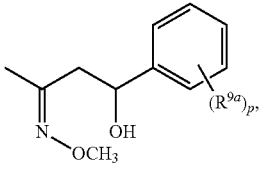
L-23
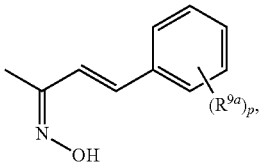
L-24
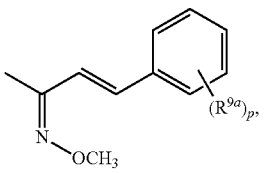
L-25
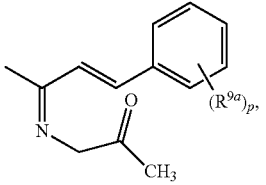

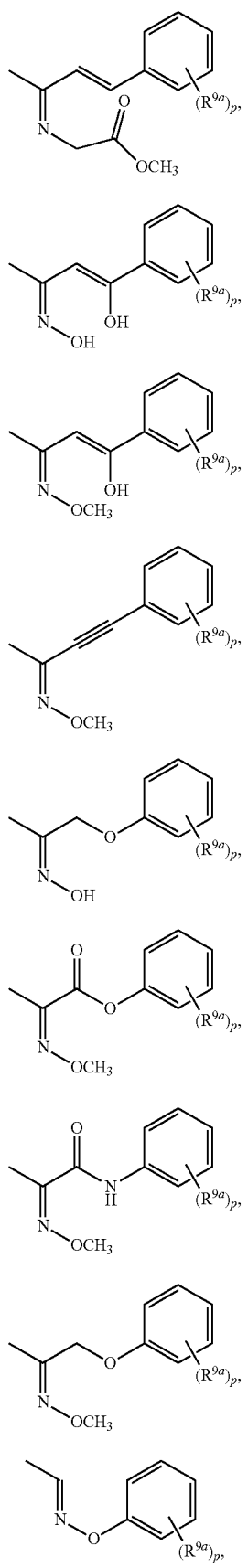
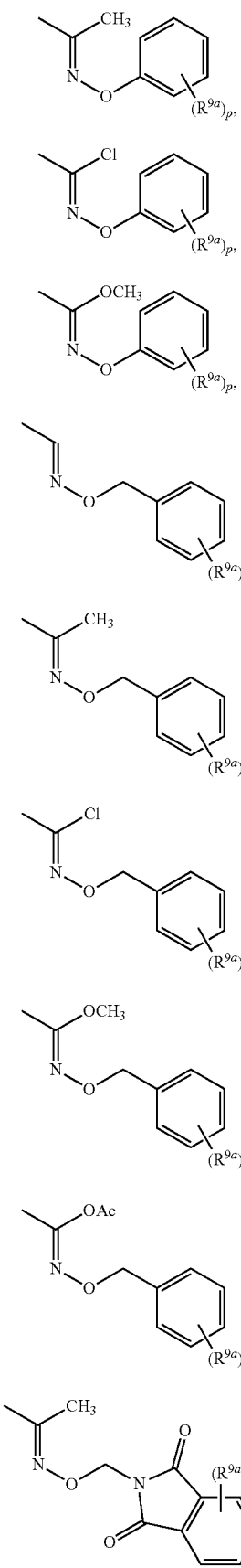

-continued

L-44

L-45

L-46

L-47

L-48

L-49

L-50

L-51

-continued

L-52

L-53

L-54

L-55

L-56

L-57

L-58

L-59

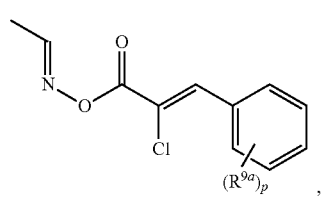
L-60
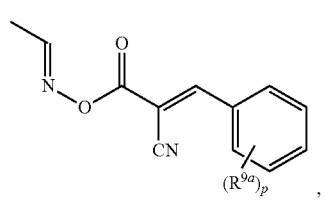
L-61
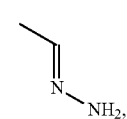
L-62
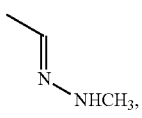
L-63
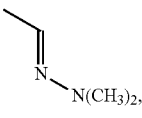
L-64
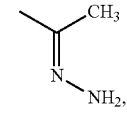
L-65
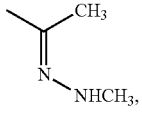
L-66
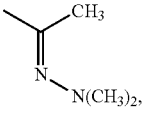
L-67
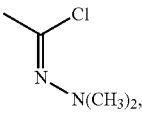
L-68
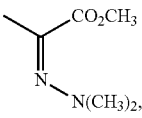
L-69
L-70
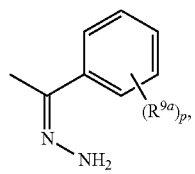
L-71
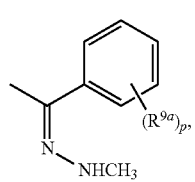
L-72
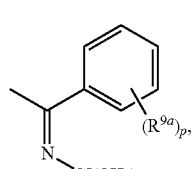
L-73
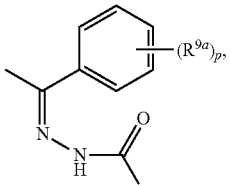
L-74
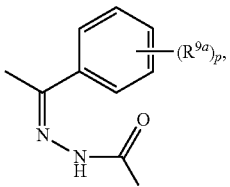
L-75
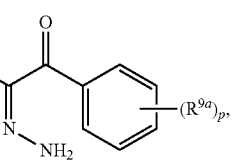
L-76
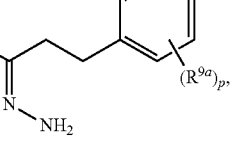
L-77
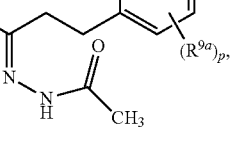
L-78

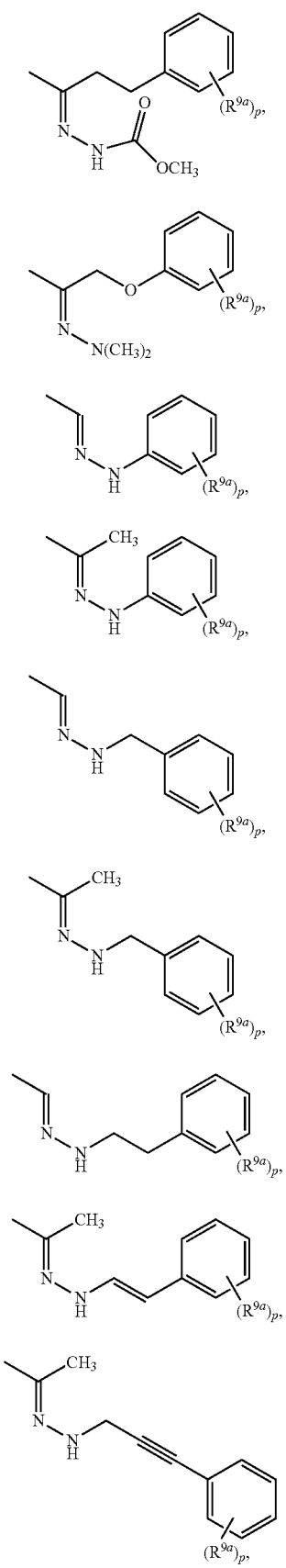
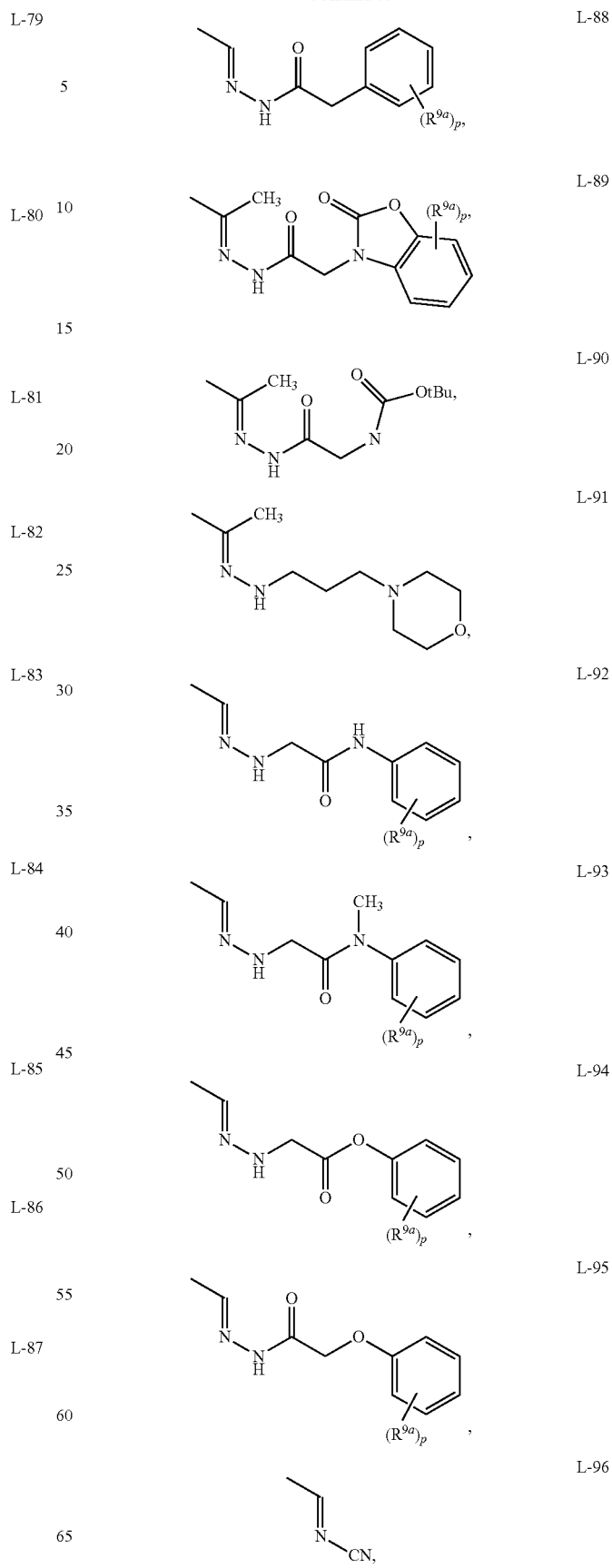

-continued

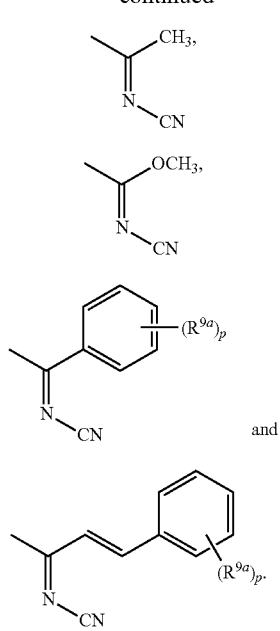

wherein p (relating to the group C(=W²)Z) is 0, 1, 2, 3, 4 or 5.

Embodiment 164. A compound of Embodiment 163 wherein p (relating to the group C(=W²)Z) is 0, 1, 2 or 3.

Embodiment 165. A compound of Embodiment 163 or 164 wherein the group C(=W²)Z is selected from L-1, L-2, L-10, L-21 through L-26, L-34, L-35, L-36, L-38, L-39, L-40, L-43, L-45, L-46, L-48, L-49, L-50, L-53, L-55, L-57, L-60, L-62 through L-67, L-83, L-84, L-96 and L-97.

Embodiment 166. A compound of Embodiment 165 wherein the group C(=W²)Z is selected from L-1, L-2, L-10, L-21, L-22, L-23, L-38, L-39, L-45, L-46, L-48, L-49, L-57 and L-60.

Embodiment 166a. A compound of Embodiment 166 wherein the group C(=W²)Z is selected from L-38, L-39, L-45, L-46, L-48 and L-49.

Embodiment 166b. A compound of Embodiment 166a wherein the group C(=W²)Z is L-45 or L-46.

Embodiment 167. A compound of Embodiment 166 wherein the group C(=W²)Z is L-21 or L-23.

Embodiment 168. A compound of Embodiment 167 wherein the group C(=W²)Z is L-21.

Embodiment 169. A compound of Embodiment 167 wherein the group C(=W²)Z is L-23.

Embodiment 170. A compound of Formula 1 or any one of Embodiments 1 through 169 wherein each $R^{9a}$ is independently halogen, hydroxy, amino, cyano, nitro, $C_1$-$C_6$ alkyl, $C_2$-$C_6$ alkenyl, $C_2$-$C_6$ alkynyl, $C_3$-$C_6$ cycloalkyl, $C_4$-$C_{10}$ cycloalkylalkyl, $C_4$-$C_{10}$ alkylcycloalkyl, $C_5$-$C_{10}$ alkylcycloalkylalkyl, $C_6$-$C_{14}$ cycloalkylcycloalkyl, $C_1$-$C_6$ haloalkyl, $C_2$-$C_6$ haloalkenyl, $C_2$-$C_6$ haloalkynyl, $C_3$-$C_6$ halocycloalkyl, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_1$-$C_4$ hydroxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkyl-carbonylthio, $C_2$-$C_6$ alkylaminocarbonyl, $C_3$-$C_8$ dialkylaminocarbonyl or $C_3$-$C_6$ trialkylsilyl; or
phenyl optionally substituted with up to 3 substituents independently selected from halogen, $C_1$-$C_2$ alkyl, $C_1$-$C_2$ haloalkyl and $C_1$-$C_2$ alkoxy; or
a 5- to 6-membered heteroaromatic ring containing ring members selected from carbon atoms and up to 4 heteroatoms independently selected from up to 2 O, up to 2 S and up to 4 N atoms, and optionally substituted with up to 3 substituents independently selected from halogen, cyano, $C_1$-$C_2$ alkyl, $C_1$-$C_2$ haloalkyl, $C_1$-$C_2$ alkoxy and $C_1$-$C_2$ haloalkoxy on carbon atom ring members and cyano, $C_1$-$C_2$ alkyl and $C_1$-$C_2$ alkoxy on nitrogen atom ring members.

Embodiment 171. A compound of Embodiment 170 wherein each $R^{9a}$ is independently halogen, amino, cyano, $C_1$-$C_6$ alkyl, $C_2$-$C_6$ alkenyl, $C_2$-$C_6$ alkynyl, $C_3$-$C_6$ cycloalkyl, $C_4$-$C_{10}$ cycloalkylalkyl, $C_1$-$C_6$ haloalkyl, $C_3$-$C_6$ halocycloalkyl, $C_1$-$C_4$ alkoxy, $C_1$-$C_4$ haloalkoxy, $C_1$-$C_4$ alkylthio, $C_1$-$C_4$ alkylsulfonyl, $C_1$-$C_4$ alkylamino, $C_2$-$C_8$ dialkylamino, $C_2$-$C_4$ alkoxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylaminocarbonyl or $C_3$-$C_8$ dialkylaminocarbonyl; or
phenyl optionally substituted with up to 3 substituents independently selected from halogen, $C_1$-$C_2$ alkyl, $C_1$-$C_2$ haloalkyl and $C_1$-$C_2$ alkoxy.

Embodiment 172. A compound of Embodiment 171 wherein each $R^{9a}$ is independently halogen, $C_1$-$C_6$ alkyl, $C_1$-$C_6$ haloalkyl or $C_1$-$C_4$ alkoxy.

Embodiment 173. A compound of Formula 1 or any one of Embodiments 1 through 172 wherein each $R^{9b}$ is independently hydrogen, $C_1$-$C_3$ alkyl, $C_2$-$C_3$ alkylcarbonyl, $C_2$-$C_3$ alkoxycarbonyl or $C_3$-$C_6$ cycloalkyl.

Embodiment 174. A compound of Formula 1 or any one of Embodiments 1 through 173 wherein $R^7$ when taken alone (i.e. not taken together with $R^3$) is H, $C_1$-$C_2$ alkyl, $C_1$-$C_2$ haloalkyl, $CH_3C(=O)$, $CF_3C(=O)$ or $CH_3OC(=O)$.

Embodiment 175. A compound of Embodiment 174 wherein $R^7$ when taken alone is H or $C_1$-$C_2$ alkyl.

Embodiment 176. A compound of Embodiment 175 wherein $R^7$ when taken alone is H or methyl.

Embodiment 177. A compound of Formula 1 or any one of Embodiments 1 through 176 wherein $R^7$ is taken alone.

Embodiment 178. A compound of Formula 1 or any one of Embodiments 1 through 177 wherein A is $CHR^{15}$.

Embodiment 179. A compound of Embodiment 178 wherein $R^{15}$ is H, halogen, cyano, hydroxy, —CHO, $C_1$-$C_4$ alkyl, $C_1$-$C_4$ haloalkyl, $C_2$-$O_5$ alkoxycarbonyl or $C_1$-$C_4$ alkoxy.

Embodiment 180. A compound of Embodiment 179 wherein $R^{15}$ is H, halogen, cyano, hydroxy, methyl or methoxy.

Embodiment 181. A compound of Embodiment 180 wherein $R^{15}$ is H.

Embodiment 182. A compound of Formula 1 or any one of Embodiments 1 through 177 wherein A is $NR^{16}$.

Embodiment 183. A compound of Embodiment 182 wherein $R^{16}$ is H, $C_1$-$C_4$ alkyl, $C_1$-$C_4$ haloalkyl, $C_2$-$C_4$ alkylcarbonyl, $C_2$-$C_4$ haloalkylcarbonyl or $C_2$-$C_4$ alkoxycarbonyl.

Embodiment 184. A compound of Embodiment 183 wherein $R^{16}$ is H, methyl, methylcarbonyl or methoxycarbonyl.

Embodiment 185. A compound of Embodiment 184 wherein $R^{16}$ is H.

Embodiment 186. A compound of Formula 1 or any one of Embodiments 1 through 185 wherein each $R^{18}$ and $R^{19}$ independently is selected from $C_1$-$C_6$ alkyl, $C_3$-$C_4$ alkenyl, $C_3$-$C_4$ alkynyl, $C_1$-$C_4$ haloalkyl, $C_3$-$C_6$ haloalkenyl, $C_3$-$C_6$ haloalkynyl, $C_2$-$C_6$ alkoxyalkyl and $C_3$-$C_6$ cycloalkyl.

Embodiment 187. A compound of Embodiment 186 wherein each $R^{18}$ and $R^{19}$ selected from $C_1$-$C_6$ alkyl, $C_3$-$C_4$ alkenyl, $C_3$-$C_4$ alkynyl and $C_1$-$C_4$ haloalkyl.

Embodiment 188. A compound of Embodiment 187 wherein each $R^{18}$ and $R^{19}$ independently is $C_1$-$C_4$ alkyl.

Embodiment 189. A compound of Formula 1 or any one of Embodiments 1 through, 185 wherein $R^{20}$ is selected from H, cyano, hydroxy, amino and $C_1$-$C_6$ alkyl.

Embodiment 190. A compound of Formula 1 or any one of Embodiments 1 through 185 or 189 wherein $R^{21}$ is selected from H and $C_1$-$C_6$ alkyl.

Embodiment 191. A compound of Formula 1 or any one of Embodiments 1 through 185, wherein $R^{20}$ and $R^{21}$ are taken together as —(CH$_2$)$_4$—, —(CH$_2$)$_5$— or —(CH$_2$)$_2$O(CH$_2$)$_2$—.

Embodiment 192. A compound of Embodiment 191 wherein $R^{20}$ and $R^{21}$ are taken together as —(CH$_2$)$_4$— or —(CH$_2$)$_2$O(CH$_2$)$_2$—.

Embodiment 193. A compound of Embodiment 192 wherein $R^{20}$ and $R^{21}$ are taken together as —(CH$_2$)$_4$—.

Embodiment 194. A compound of Formula 1 or any one of Embodiments 1 through 185 wherein $R^{22}$ is H, halogen, cyano or $C_1$-$C_4$ alkyl.

Embodiment 195. A compound of Embodiment 194 wherein $R^{22}$ is H, halogen or cyano.

Embodiment 196. A compound of Embodiment 195 wherein $R^{22}$ is Cl or cyano.

Embodiment 197. A compound of Formula 1 or any one of Embodiments 1 through 196, wherein when Z is hydrogen, unsubstituted $C_1$-$C_6$ alkyl, $C_1$-$C_6$ haloalkyl, unsubstituted $C_3$-$C_6$ cycloalkyl or unsubstituted phenyl; then $R^{12}$ or $R^{14}$ are independently hydrogen or $C_2$-$C_4$ alkylcarbonyl optionally substituted by up to one $Q^1$ and up to 2 substituents selected from $C_1$-$C_3$ alkyl, $C_1$-$C_3$ haloalkyl, $C_1$-$C_3$ alkoxy, hydroxyl and cyano.

Embodiments of this invention, including Embodiments 1-197 above as well as any other embodiments described herein, can be combined in any manner, and the descriptions of variables in the embodiments pertain not only to the compounds of Formula 1 but also to the starting compounds and intermediate compounds useful for preparing the compounds of Formula 1. In addition, embodiments of this invention, including Embodiments 1-197 above as well as any other embodiments described herein, and any combination thereof, pertain to the compositions and methods of the present invention.

Combinations of Embodiments 1-197 are illustrated by:

Embodiment A1. A compound of Formula 1 wherein
E is E-1;
X is X-1, X-2, X-3, X-4 or X-5; and
G is a 5-membered heterocyclic ring optionally substituted with up to 2 substituents independently selected from $R^{29a}$ on carbon atom ring members and $R^{30a}$ on nitrogen atom ring members.

Embodiment A2. A compound of Embodiment A1 wherein
X is X-1, X-2 or X-3;
G is selected from G-1 through G-48 shown in Exhibit 3;
$R^{29a}$ is H;
each $R^{30a}$ is independently hydrogen or methyl; and
Q is selected from Q-1 through Q-102.

Embodiment A3. A compound of Embodiment A2 wherein
$R^{1a}$ is U-1, U-20 or U-50;
each $R^{33a}$ is independently halogen, $C_1$-$C_3$ alkyl, $C_1$-$C_3$ haloalkyl or $C_2$-$C_3$ alkoxyalkyl;
k is 0, 1, 2 or 3;
A is CHR$^{15}$;
$R^{15}$ is H;
W is O;
X is X-1;
n is 0;
G is G-1;
each $R^{9a}$ is independently halogen, $C_1$-$C_6$ alkyl, $C_1$-$C_6$ haloalkyl or $C_1$-$C_4$ alkoxy; and
p is 0, 1, 2 or 3.

Embodiment A4. A compound of Embodiment A3 wherein
$W^2$ is selected from J-1, J-2 and J-4;
Z is $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_2$-$C_4$ alkoxyalkyl, $C_2$-$C_4$ alkylthioalkyl, $C_2$-$C_4$ alkylsulfinylalkyl, $C_2$-$C_4$ alkylsulfonylalkyl, $C_2$-$C_4$ alkylcarbonyl, $C_2$-$C_4$ haloalkylcarbonyl, $C_2$-$C_5$ alkoxycarbonyl, $C_2$-$C_5$ alkylaminocarbonyl, $C_3$-$C_5$ dialkylaminocarbonyl, $C_2$-$C_4$ aminocarbonylalkyl or $C_3$-$C_6$ cycloalkyl, each optionally substituted by up to one Q and up to 2 substituents selected from $C_1$-$C_3$ alkyl, $C_1$-$C_3$ haloalkyl, $C_1$-$C_3$ alkoxy, hydroxyl and cyano; and
Q is Q-45.

Embodiment A5. A compound of Embodiment A4 wherein C(=W$^2$)Z is selected from L-20 through L-25.

Embodiment A6. compound of Embodiment A3 wherein
$W^2$ is NOR$^{12}$;
$R^{12}$ is $C_1$-$C_2$ alkyl optionally substituted by up to one $Q^1$ or when $R^{12}$ is $Q^1$ then $Q^1$ is Q-103;
Z is CH$_3$ or hydrogen; and
$Q^1$ is Q-45.

Embodiment A7. A compound of Embodiment A6 wherein C(=W$^2$)Z is selected from L-38, L-39, L-45, L-46, L-48 and L-49.

Specific embodiments include compounds of Formula 1 selected from the group consisting of:

3-(2,6-difluorophenyl)-3-hydroxy-1-[2-[1-[2-[5-methyl-3-(trifluoromethyl)-1H-pyrazol-1-yl]acetyl]-4-piperidinyl]-4-thiazolyl]-1-propanone 1-oxime;

3-(2,6-difluorophenyl)-1-[2-[1-[2-[5-methyl-3-(trifluoromethyl)-1H-pyrazol-1-yl]acetyl]-4-piperidinyl]-4-thiazolyl]-2-propen-1-one 1-oxime;

2-[5-methyl-3-(trifluoromethyl)-1H-pyrazol-1-yl]-1-[4-[4-[1-[(2-phenylethoxy)imino]ethyl]-2-thiazolyl]-1-piperidinyl]ethanone;

2-[1-[2-[5-methyl-3-(trifluoromethyl)-1H-pyrazol-1-yl]acetyl]-4-piperidinyl]-4-thiazolecarboxaldehyde 4-[O-(1-phenylethyl)oxime];

3-(2,6-difluorophenyl)-1-[2-[1-[2-[5-methyl-3-(trifluoromethyl)-1H-pyrazol-1-yl]acetyl]-4-piperidinyl]-4-thiazolyl]-2-propen-1-one 1-(O-methyloxime); and 3-(2,6-difluorophenyl)-1-[2-[1-[2-[5-methyl-3-(trifluoromethyl)-1H-pyrazol-1-yl]acetyl]-4-piperidinyl]-4-thiazolyl]-2-propen-1-one 1-(O-acetyloxime).

This invention provides a fungicidal composition comprising a compound of Formula 1 (including all stereoisomers, or an N-oxide, or a salt thereof), and at least one other fungicide. Of note as embodiments of such compositions are compositions comprising a compound corresponding to any of the compound embodiments described above.

This invention provides a fungicidal composition comprising a compound of Formula 1 (including all stereoisomers, or an N-oxide, or a salt thereof) (i.e. in a fungicidally effective amount), and at least one additional component selected from the group consisting of surfactants, solid diluents and liquid diluents. Of note as embodiments of such compositions are compositions comprising a compound corresponding to any of the compound embodiments described above.

This invention provides a method for controlling plant diseases caused by fungal plant pathogens comprising applying to the plant or portion thereof, or to the plant seed, a fungicidally effective amount of a compound of Formula 1 (including all stereoisomers, or an N-oxide, or a salt thereof). Of note as embodiment of such methods are methods comprising applying a fungicidally effective amount of a compound corresponding to any of the compound embodiments describe above. Of particular note are embodiments where the compounds are applied as compositions of this invention.

Further embodiments of this invention include embodiments of Formula 1A. Embodiments of Formula 1A include geometric and stereoisomers, tautomers, N-oxides, and salts thereof, and reference to "a compound of Formula 1A" includes the definitions of substituents specified in the Summary of the Invention unless further defined in the Embodiments.

Embodiment B1. A compound of Formula 1A wherein E is E-1.

Embodiment B2. A compound of Formula 1A or Embodiment B1 wherein $R^{1a}$ is U-1, U-20 or U-50.

Embodiment B3. A compound of Formula 1A or Embodiments B1 through B2 wherein A is $CH_2$, NH or C=O.

Embodiment B4. A compound of Formula 1A or Embodiments B1 through B3 wherein X is X-1.

Embodiment B5. A compound of Formula 1A or Embodiments B1 through B4 wherein n is 0.

Embodiment B6. A compound of Formula 1A or Embodiments B1 through B5 wherein W is O.

Embodiment B7. A compound of Formula 1A or Embodiments B1 through B6 wherein G is G-1.

Embodiment B8. A compound of Formula 1A or Embodiments B1 through B7 wherein $Z^1$ is $CH_2CH_2Q$, CH=CHQ, C≡CQ and $CH_2CH(OH)Q$.

Embodiment B8a. A compound of Formula 1A or Embodiments B1 through B7 wherein $Z^1$ is CH=CHQ or $CH_2CH(OH)Q$.

Embodiment B8b. A compound of Formula 1A or Embodiments B1 through B7 wherein $Z^1$ is CH=CHQ.

Embodiment B9. A compound of Formula 1A or Embodiments B1 through B8 wherein Q is an optionally substituted phenyl or optionally substituted 5- to 6-membered heterocyclic ring.

Combinations of Embodiments 1B-B-9 are illustrated by:

Embodiment C1. A compound of Formula 1A wherein
E is E-1;
$R^{1a}$ is U-1, U-20 or U-50;
A is $CH_2$, NH or C=O;
X is X-1;
n is 0;
W is O;
G is G-1;
$Z^1$ is $CH_2CH_2Q$, CH=CHQ, C≡CQ and $CH_2CH(OH)Q$; and
Q is an optionally substituted phenyl or optionally substituted 5- to 6-membered heterocyclic ring.

Embodiment C2. A compound of Formula 1A wherein
E is E-1;
$R^{1a}$ is U-1, U-20 or U-50;
A is $CH_2$, NH or C=O;
X is X-1;
n is 0;
W is O;
G is G-1;
$Z^1$ is CH=CHQ; and
Q is an optionally substituted phenyl or optionally substituted 5- to 6-membered heterocyclic ring.

Embodiment C3. A compound of Formula 1A wherein
E is E-1;
$R^{1a}$ is U-1, U-20 or U-50;
A is $CH_2$, NH or C=O;
X is X-1;
n is 0;
W is O;
G is G-1;
$Z^1$ is CH=CHQ; and
Q is selected from Q-32, Q-33, Q-34, Q-36, Q-38, Q-39, Q-45, Q-46, Q-47, Q-63, Q-65, Q-70, Q-71, Q-72, Q-84 and Q-85.

Specific embodiments include compounds of Formula 1A selected from the group consisting of:

3-(2,6-difluorophenyl)-1-[2-[1-[2-[5-methyl-3-(trifluoromethyl)-1H-pyrazol-1-yl]acetyl]-4-piperidinyl]-4-thiazolyl]-2-propen-1-one.

One or more of the following methods and variations as described in Schemes 1-28 can be used to prepare the compounds of Formula 1. The definitions of E, X, G, W, $W^1$, $W^2$, Z, A, $A^1$, Q, $R^{1a}$, $R^{1b}$, $R^2$, $R^3$, $R^4$, $R^5$, $R^7$, $R^8$, $R^{12}$, $R^{13}$, $R^{14}$, $R^{16}$, $R^{19}$, $R^{20}$, $R^{21}$, $R^{22}$, $R^{24}$, $R^{25}$, $R^{26}$ and $R^{27}$ (in the compounds of Formulae 1-48) below are as defined above in the Summary of the Invention unless otherwise noted. Compounds of Formulae 1-1k are various subsets of the compounds of Formula 1, and all substituents for Formulae 1a-1k are as defined above for Formula 1.

As shown in Scheme 1, compounds of Formula 1a (Formula 1 wherein E is E-1, A is $CHR^{15}$ or C=O) wherein W is O can be prepared by coupling an acid chloride of Formula 2 with an amine of Formula 3 in the presence of an acid scavenger. Typical acid scavengers include amine bases such as triethylamine, N,N-diisopropylethylamine and pyridine. Other scavengers include hydroxides such as sodium and potassium hydroxide and carbonates such as sodium carbonate and potassium carbonate. In certain instances it is useful to use polymer-supported acid scavengers such as polymer-bound N,N-diisopropylethylamine and polymer-bound 4-(dimethylamino)pyridine. One skilled in the art will recognize that mixtures may result when an amine of Formula 3 contains a second NH function and standard methods of separation can be employed to isolate the desired isomer.

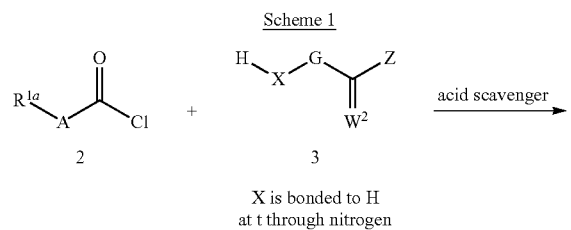

Scheme 1

X is bonded to H
at t through nitrogen

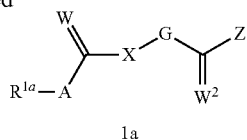

1a wherein E is E-1, A is CHR$^{15}$ or C(=O) and W is O

Acid salts of the Formula 3 amines can also be used in this reaction, provided that at least 2 equivalents of the acid scavenger is present. Typical acids used to form salts with amines include hydrochloric acid, oxalic acid and trifluoroacetic acid. In a subsequent step, amides of Formula 1a wherein W is O can be converted to thioamides of Formula 1a wherein W is S using a variety of standard thiating reagents such as phosphorus pentasulfide or 2,4-bis (4-methoxyphenyl)-1,3-dithia-2,4-diphosphetane-2,4-disulfide (Lawesson's reagent).

An alternate procedure for the preparation of compounds of Formula 1a wherein W is O is depicted in Scheme 2 and involves coupling of an acid of Formula 4 with an amine of Formula 3 (or its acid salt) in the presence of a dehydrative coupling reagent such as dicyclohexylcarbodiimide (DCC), 1-(3-dimethylaminopropyl)-3-ethylcarbodiimide hydrochloride (EDC) or O-benzotriazol-1-yl-N,N,N',N'-tetramethyluronium hexafluoro-phosphate (HBTU). Polymer-supported reagents are again useful here, such as polymer-bound cyclohexylcarbodiimide. These reactions are typically run at 0-40° C. in a solvent such as dichloromethane or acetonitrile in the presence of a base such as triethylamine or N,N-diisopropylethylamine. One skilled in the art will recognize that mixtures may result when an amine of Formula 3 contains a second NH function and standard methods of separation can be employed to isolate the desired isomer.

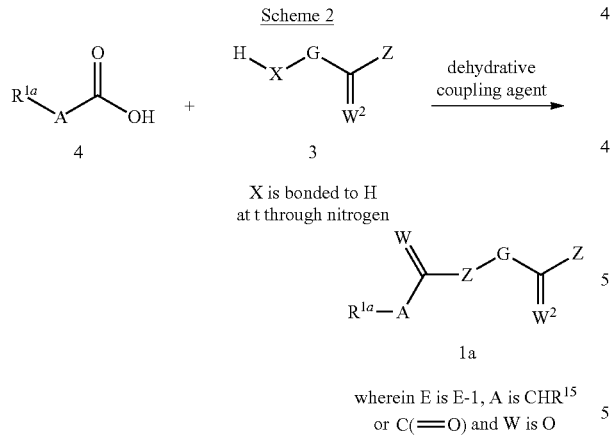

The acids of Formula 4 are known or can be prepared by methods known to one skilled in the art. For example, R$^{1a}$CH$_2$COOH where R$^{1a}$ is linked to the acetic acid residue via a heteroatom can be prepared by reacting the corresponding R$^{1a}$H with a haloacetic acid or ester in the presence of base; see, for example, U.S. Pat. No. 4,084,955. R$^{1a}$CH$_2$COOH wherein R$^{1a}$ is linked to the acetic acid residue via a carbon atom can be prepared from the corresponding R$^{1a}$CH$_2$-halogen compounds by displacement of the halogen with cyanide followed by hydrolysis; see, for example, K. Adachi, *Yuki Gosei Kagaku Kyokaishi* 1969, 27, 875-876; or from R$^{1a}$C(=O)CH$_3$ by the Willgerodt-Kindler reaction; see, for example, H. R. Darabi et al., *Tetrahedron Letters* 1999, 40, 7549-7552 and M. M. Alam and S. R. Adapa, *Synthetic Communications* 2003, 33, 59-63 and references cited therein; or from R$^{1a}$Br or R$^{1a}$I by palladium-catalyzed cross-coupling with tert-butyl acetate or diethyl malonate followed by ester hydrolysis; see, for example, W. A. Moradi and S. L. Buchwald, *J. Am. Chem. Soc.* 2001, 123, 7996-8002 and J. F. Hartwig et al., *J. Am. Chem. Soc.* 2002, 124, 12557-12565.

As the synthetic literature includes many amide-forming methods, the synthetic procedures of Schemes 1 and 2 are simply representative examples of a wide variety of methods useful for the preparation of Formula 1 compounds. One skilled in the art also realizes that acid chlorides of Formula 2 can be prepared from acids of Formula 4 by numerous well-known methods.

Certain compounds of Formula 1a (Formula 1 wherein E is E-1, A is CHR$^{15}$ or C=O, and W is O) wherein R$^{1a}$ is linked to A via a heteroatom can be prepared by reaction of the compound of Formula 5 and a haloacetamide or oxalyl chloride of Formula 6 as shown in Scheme 3. The reaction is carried out in the presence of a base such as sodium hydride, potassium carbonate or triethylamine in a solvent such as tetrahydrofuran, N,N-dimethylformamide or acetonitrile at 0 to 80° C. The haloacetamide of Formula 6 can be prepared by the reaction of an amine of Formula 3 with an α-halo carboxylic acid halide or an α-halo carboxylic acid or its anhydride, analogous to the amide-forming reactions described in Schemes 1 and 2, respectively. The oxalyl chlorides of Formula 6 (i.e. where A is C(=O) can be prepared by the reaction of an amine of Formula 3 and oxalyl chloride as known to one skilled in the art.

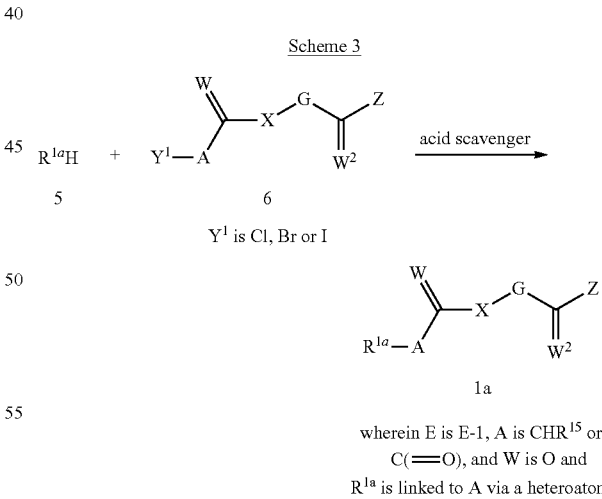

Compounds of Formula 1b (Formula 1 wherein E is E-1 and A is NR$^{16}$), wherein R$^{16}$ is H, and W is O or S, can be prepared by reaction of an amine of Formula 3 with an isocyanate or isothiocyanate, respectively, of Formula 7 as depicted in Scheme 4. This reaction is typically carried out at ambient temperature in an aprotic solvent such as dichloromethane or acetonitrile.

Scheme 4

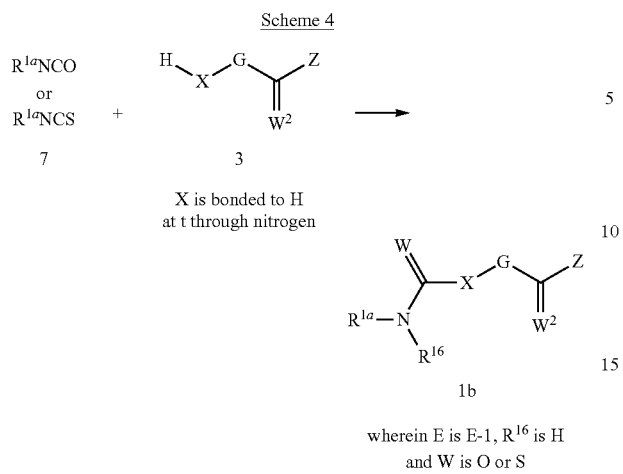

wherein E is E-1, R¹⁶ is H
and W is O or S

Compounds of Formula 1b can also be prepared by the reaction of an amine of Formula 8 with a carbamoyl or thiocarbamoyl chloride or imidazole of Formula 9 as shown in Scheme 5. When $Y^2$ is chlorine, the reaction is typically carried out in the presence of an acid scavenger. Typical acid scavengers include amine bases such as triethylamine, N,N-diisopropylethylamine and pyridine. Other scavengers include hydroxides such as sodium and potassium hydroxide and carbonates such as sodium carbonate and potassium carbonate. The carbamoyl or thiocarbamoyl chlorides of Formula 9 (wherein $Y^2$ is Cl) can be prepared from amines of Formula 3 by treatment with phosgene or thiophosgene, respectively, or their equivalents, while carbamoyl or thiocarbamoyl imidazoles of Formula 9 (wherein $Y^2$ is imidazol-1-yl) can be prepared from amines of Formula 3 by treatment with 1,1'-carbonyldiimidazole or 1,1'-thiocarbonyldiimidazole, respectively, according to general methods known to one skilled in the art.

Scheme 5

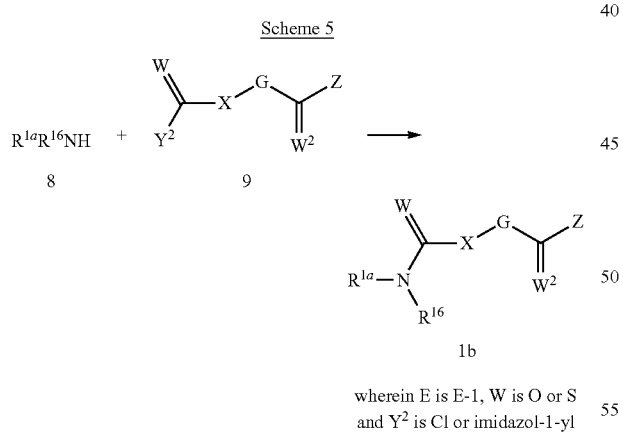

wherein E is E-1, W is O or S
and $Y^2$ is Cl or imidazol-1-yl

As shown in Scheme 6, compounds of Formula 1c (Formula 1 wherein E is E-2,) wherein W is O can be prepared by coupling an acid chloride of Formula 10 with an amine of Formula 3 in the presence of an acid scavenger, analogous to the method described in Scheme 1. In a subsequent step, compounds of Formula 1c wherein W is O are converted to the corresponding thioamides wherein W is S using a variety of standard thiating reagents such as phosphorus pentasulfide or 2,4-bis(4-methoxyphenyl)-1,3-dithia-2,4-diphosphetane-2,4-disulfide (Lawesson's reagent).

Scheme 6

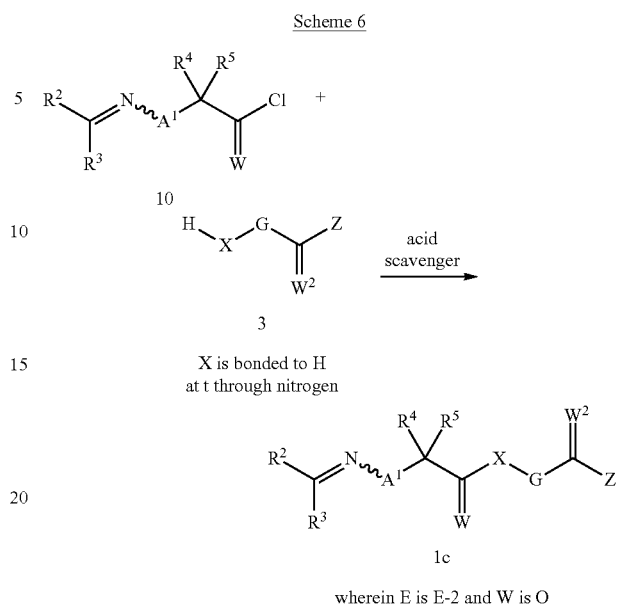

wherein E is E-2 and W is O

An alternate procedure for the preparation of compounds of Formula 1c (Formula 1 wherein E is E-2 and W is O) is depicted in Scheme 7 and involves coupling of an acid of Formula 11 with an amine of Formula 3 (or its acid salt) in the presence of a dehydrative coupling reagent analogous to the method described in Scheme 2. The acids of Formula 11 are known or can be prepared by methods known to one skilled in the art. For leading references see, for example, Schumann, Paquette et al., J. Med. & Pharm. Chem. 1962, 5, 464-77; Van Dijk, Jan et al., J. Med. Chem. 1977, 20(9), 1199-206; A. Balsamo et al., J. Med. Chem. 1989, 32, 1398-1401 and references cited therein, and U.S. Pat. No. 4,584,014.

Scheme 7

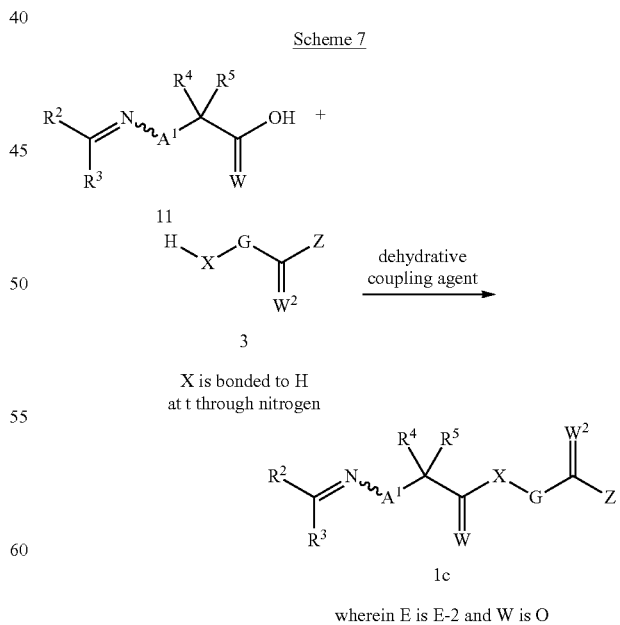

wherein E is E-2 and W is O

Analogous to Scheme 6, compounds of Formula 1c wherein W is O are converted to the corresponding thioamides wherein W is S using a variety of standard thiating reagents such as phosphorus pentasulfide or 2,4-bis(4-methoxyphenyl)-1,3-dithia-2,4-diphosphetane-2,4-disulfide (Lawesson's reagent).

Acid chlorides of Formula 10 can be prepared from acids of Formula 11 by numerous well known methods.

As the synthetic literature includes many amide-forming methods, the methods of Schemes 6 and 7 are simply representative examples of a wide variety of methods useful for the preparation of Formula 1 compounds.

Compounds of Formula 1c (Formula 1 wherein E is E-2,) wherein $A^1$ is —O—, —S— and —N($R^7$)— and W is O can be prepared by reaction of a compound of Formula 12 and a haloacetamide of Formula 13 wherein $Y^3$ is Cl, Br or I as shown in Scheme 8. The reaction is carried out in the presence of a base such as sodium hydride or potassium carbonate in a solvent such as tetrahydrofuran, N,N-dimethylformamide or acetonitrile typically at 0 to 80° C. The imines, oximes and hydrazones of Formula 12 are known or can be prepared by methods known in the art; see, for example, S. Dayagi et al., in *The Chemistry of the Carbon-Nitrogen Double Bond*, ed. S. Patei, Interscience, New York 1970; S. R. Sandler et al., *Organic Functional Group Preparations*, Academic Press, New York 1972, 3, 372 and G. Hilgetag et al., *Preparative Organic Chemistry*, John Wiley & Sons, New York 1972, 504-515.

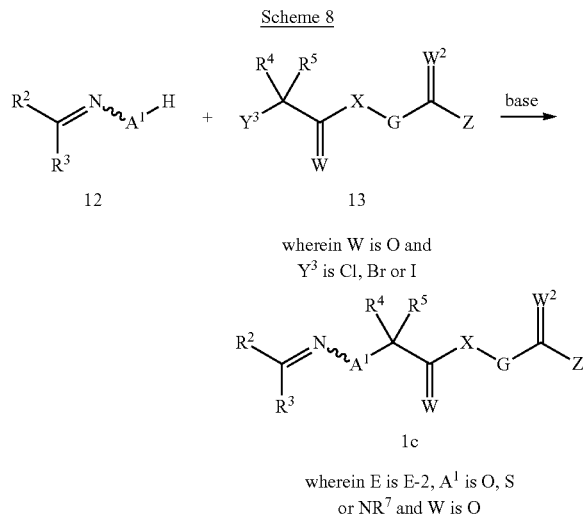

Haloacetamide compounds of Formula 13 can be prepared by the reaction of an amine of Formula 3 with an α-halo carboxylic acid halide or an α-halo carboxylic acid or its anhydride, analogous to the amide-forming reactions described in Schemes 1 and 2, respectively.

Compounds of Formula 1c (Formula 1 wherein E is E-2) wherein $A^1$ is —OC($R^8$)$_2$—, —SC($R^8$)$_2$— or —N($R^7$)C($R^8$)$_2$— and $R^5$ is H can be prepared by a base-catalyzed condensation reaction of a compound of Formula 12a with an α,β-unsaturated amide of Formula 14 as depicted in Scheme 9 wherein V in Formula 12a and C($R^8$)$_2$ in Formula 14 forms $A^1$ in Formula 1c. The reaction is carried out in the presence of a base such as sodium or potassium hydroxide, sodium hydride or potassium carbonate in a solvent such as tetrahydrofuran, N,N-dimethylformamide, ethanol or acetonitrile typically at 0 to 80° C. The α,β-unsaturated amide of Formula 14 can be prepared by coupling of the corresponding α,β-unsaturated acid or acid chloride with an amine of Formula 3 by a method analogous to methods described in Scheme 1 and 2.

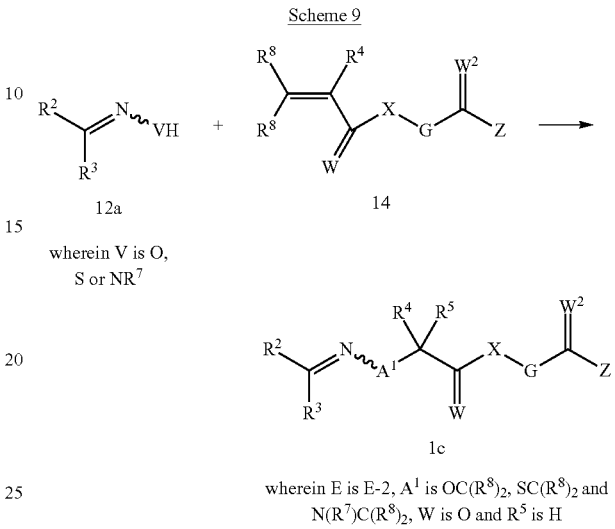

Compounds of Formula 1c (Formula 1 wherein E is E-2) can also be prepared by reacting a compound of Formula 15 with a compound of Formula 16 as illustrated in Scheme 10. The reaction can be carried out in a solvent such as ethanol, tetrahydrofuran or water, and optionally in the presence of an acid catalyst such as acetic acid, hydrochloric acid or sulfuric acid. Acid salts of Formula 16 can also be used in the method of Scheme 10, preferably in the presence of at least one molar equivalent of an acid scavenger such as pyridine or triethylamine. Typical acids used to form salts with amines include hydrochloric acid, oxalic acid and trifluoroacetic acid. The reaction of amines with carbonyl compounds is well known see, for example, S. Dayagi et al. in *The Chemistry of the Carbon-Nitrogen Double Bond*, ed. S. Patei, Interscience, New York 1970; S. R. Sandler et al., *Organic Functional Group Preparations*, Academic Press, New York 1972, 3, 372 and G. Hilgetag et al., *Preparative Organic Chemistry*, John Wiley & Sons, New York 1972, 504-515. Compounds of Formula 15 are known or can be prepared by methods known to one skilled in the art. Compounds of Formula 16 can be prepared directly or by deprotection of corresponding N-protected compounds of Formula 16. The N-protected compounds of Formula 16 can be prepared by methods analogous to those already described for Schemes 1, 2, 3, and 4. The choice and use of a suitable N-protected nitrogen will be apparent to one skilled in the art; for representative examples see T. W. Greene and P. G. M. Wuts, *Protective Groups in Organic Synthesis*, 2nd ed.; Wiley: New York, 1991.

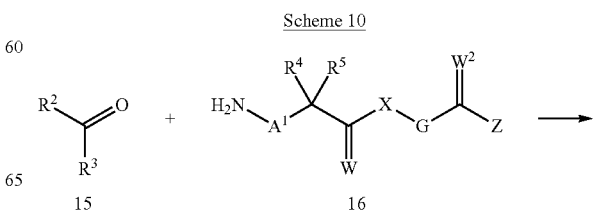

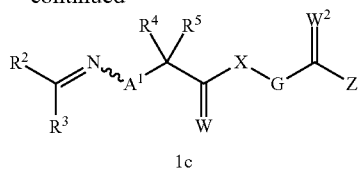

1c wherein E is E-2 and W is O

As shown in Scheme 11 certain compounds of Formulae 1d-1g (Formula 1 wherein E is E-3 and $W^1$ is $OR^{18}$, $SR^{19}$, $NR^{20}R^{21}$ or CN) can be prepared by reacting an imidoyl chloride of Formula 17 with a compound of Formula 18 in the presence of an acid scavenger. Suitable acid scavengers include, but are not limited to, amine bases such as triethylamine, N,N-diisopropylethylamine and pyridine, hydroxides such as sodium and potassium hydroxide, and carbonates such as sodium carbonate and potassium carbonate. Alternatively, the compounds of Formulae 17 and 18 can be contacted in the absence of an acid scavenger to provide compounds Formulae 1d-1f as the corresponding HCl salts, which are also compounds of the present invention. If desired, the HCl salts can be free-based by standard methods to give compounds of Formulae 1d-1f. Regardless of whether the reaction is conducted with or without an acid scavenger, it is typically conducted in a suitable organic solvent at a temperature between about 20 and 100° C. A variety of solvents can be used to form the suitable solvent for this method, for example nitriles, such as acetonitrile, ethers such as tetrahydrofuran, and halogenated hydrocarbons such as dichloromethane, and amides such as N,N-dimethylformamide, and mixtures thereof. Compounds of Formulae 1d-1g can be generally classified as isoureas, isothioureas, guanidines and cyanoamidines, respectively. For leading references on these classes of compounds see J. Lon Mathias, *Organic Preparations and Procedures International* 1980, 12(5), 309-326; *Comprehensive Organic Chemistry*, vol. 2, I. O. Sutherland, Ed., Pergamon Press, Oxford; *Rodd's Chemistry of Carbon Compounds*, vol. 1C, Elsevier, New York; A. R. Katritzky et al., *J. Organic Chem.* 2004, 69, 309-313. One skilled in the art will recognize that certain compounds of Formulae 1d, 1f and 1g can be prepared from the corresponding compound of Formula 1e by treatment with an appropriate compound of Formula 18. For example, the preparation of thiuronium salts and their conversion to guanidines is described in the literature, see C. R. Rasmussen et al., *Synthesis* 1988, 6, 460-466. Imidoyl chlorides of Formula 17 can be prepared from compounds of Formula 1b (Formula 1 wherein E is E-1, A is NH) by treating with thionyl chloride, phosphorous oxychloride or phosphorous pentachloride in a solvent such as dichlormethane. For typical reactions conditions see, for example, W. Zielinski et al., *Heterocycles* 1998, 48, 319-327 or PCT Patent Publication WO/2009/094445. Many compounds of Formula 18 are commercially available and can be prepared by methods well documented in the chemistry art.

Scheme 11

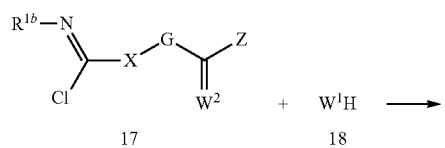

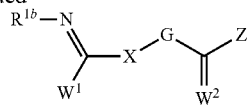

1d wherein E is E-3, $W^1$ is $OR^{18}$
1e wherein E is E-3, $W^1$ is $SR^{19}$
1f wherein E is E-3, $W^1$ is $NR^{20}R^{21}$
1g wherein E is E-3, $W^1$ is CN In an alternate procedure shown in Scheme 12, certain compounds of Formulae 1d-1f and Formula 1h (Formula 1 wherein E is E-3 and $W^1$ is $CR^{22}$) can be prepared by reacting an amine of Formula 3 with an imidoyl chloride of Formula 19 using conditions analogous to those described in Scheme 11. Many imidoyl chlorides of Formula 19 can be prepared by methods disclosed in the art, for example, see R. Bonnett in The Chemistry of the Carbon-Nitrogen Double Bond, S. Patei, Ed., Interscience Publishers, and references cited therein. Some imidoyl chlorides of Formula 19 are commercially available (e.g., Formula 19 wherein $R^{1b}$ is phenyl, substituted phenyl or lower alkyl and $W^1$ is OMe, SMe, or $N(Me)_2$ can be commercially obtained) and can be prepared by methods documented in the chemistry art.

Scheme 12

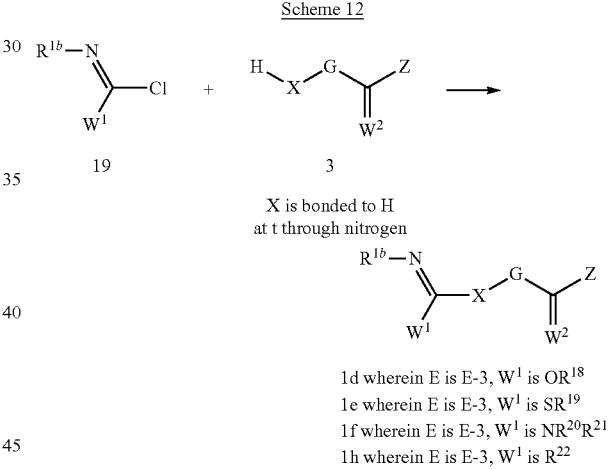

1d wherein E is E-3, $W^1$ is $OR^{18}$
1e wherein E is E-3, $W^1$ is $SR^{19}$
1f wherein E is E-3, $W^1$ is $NR^{20}R^{21}$
1h wherein E is E-3, $W^1$ is $R^{22}$ Schemes 11 and 12 are representative of just two methods of preparing compounds of Formula 1e. In another method, as shown in Scheme 13, compounds of Formula 1e can be prepared by reacting a thiourea of Formula 1b (Formula 1 wherein E is E-1, A is NH and W is S) with an alkylating or acylating agent of a compound of Formula 20 wherein $Y^4$ is a nucleophic reaction leaving group such as halide (e.g., Cl, Br, I) or sulfonate (e.g., mesylate, triflate, p-toluenesulfonate), and the like. The method can be conducted in the presence of an acid scavenger and a suitable organic solvent at a temperature between about 0 and 100° C. Suitable solvents include, for example, dichloromethane, tetrahydrofuran, acetonitrile, N,N-dimethylformamide, and mixtures thereof. Suitable acid scavengers comprise, for example, amine bases such as triethylamine, N,N-diisopropylethylamine and pyridine, hydroxides such as sodium and potassium hydroxide and carbonates such as sodium carbonate and potassium carbonate. Alternatively, compounds of Formulae 1b and 20 can be contacted in the absence of an acid scavenger to provide the corresponding isothiuronium salts of Formula 1e, which are also compounds of the present invention. In a subsequent reaction the salt can be free-based using standard methods described in the art to provide compounds of Formula 1e. For an example illustrating the preparation of thiuronium salts and their conversion to guanidines see C. R. Rasmussen et al., *Synthesis* 1988, 6, 460-466 or PCT Patent Publication WO/2009/094445. Many compounds of Formula 20 are known and can be prepared by general methods disclosed in the art.

Scheme 13

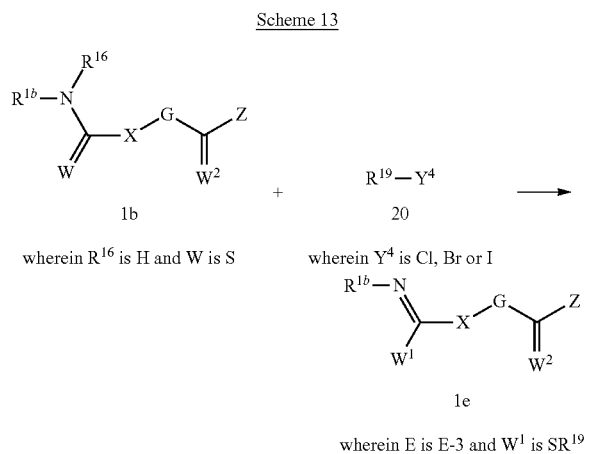

wherein $R^{16}$ is H and W is S wherein $Y^4$ is Cl, Br or I wherein E is E-3 and $W^1$ is $SR^{19}$ Compounds of Formula 1e can also be prepared by reacting an amine of Formula 3 with a dithiocarbamic acid of Formula 21 as illustrated in Scheme 14. The reaction of Scheme 14 is typically conducted in a suitable solvent at a temperature between about 0 to 100° C. Examples of suitable solvents include acetonitrile, tetrahydrofuran, dichloromethane, N,N-dimethylformamide, and mixtures thereof. Dithiocarbamic acids of Formula 21 can be prepared from the corresponding amines, carbon disulfide and two equivalents of a base, followed by treatment with an alkylating agent according to the general method of Alvarez-Ibarra et al., *Organic Preparations and Procedures* 1991, 23(5), 611-616.

Scheme 14

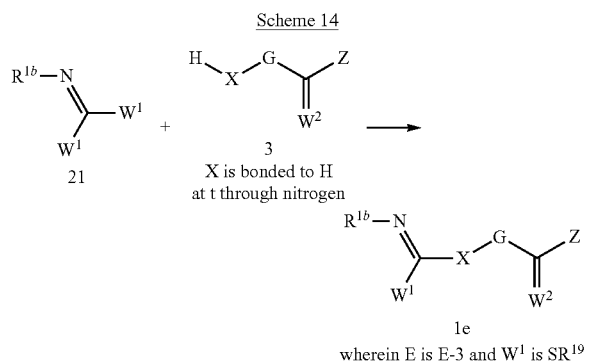

21

3
X is bonded to H
at t through nitrogen 1e
wherein E is E-3 and $W^1$ is $SR^{19}$ Certain compounds of Formula 1h wherein $R^{22}$ is H can be prepared by treating an amine of Formula 3 with a methoxy or ethoxy imine of Formula 22 as shown in Scheme 15. Imines of Formula 22 can be obtained from the corresponding amines. The procedure involves heating the amines with trimethylorthoformate or triethylorthoformate in toluene or xylenes in the presence of a catalytic amount of p-toluenesulfonic acid.

Scheme 15

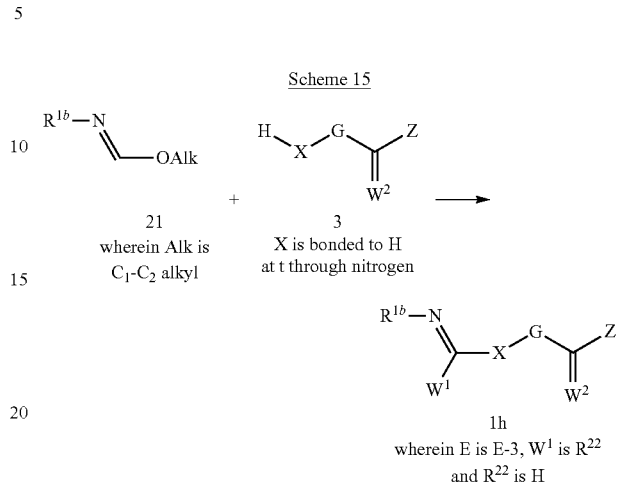

21
wherein Alk is
$C_1$-$C_2$ alkyl

3
X is bonded to H
at t through nitrogen 1h
wherein E is E-3, $W^1$ is $R^{22}$
and $R^{22}$ is H Compounds of Formula 1 wherein a carbon in X is linked via v to a nitrogen atom in G, can be prepared by displacement of an appropriate leaving group (i.e. $Y^5$) in a compound of Formula 23 with a nitrogen-containing heterocycle of Formula 24 in the presence of a base as depicted in Scheme 16. Suitable bases include sodium hydride or potassium carbonate, and the reaction can be carried out in a solvent such as N,N-dimethylformamide or acetonitrile at 0 to 80° C. Suitable leaving groups in the compounds of Formula 23 include bromide, iodide, mesylate ($OS(O)_2CH_3$), triflate ($OS(O)_2CF_3$) and the like. Compounds of Formula 23 can be prepared from the corresponding compounds wherein $Y^5$ is OH, using general methods known in the art.

Scheme 16

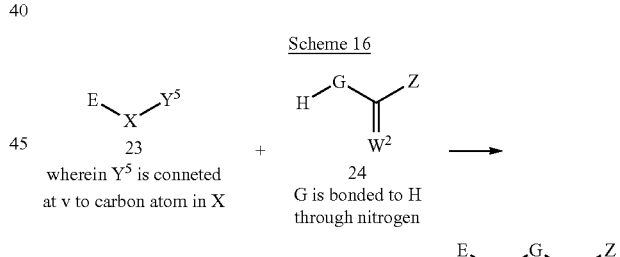

23
wherein $Y^5$ is conneted
at v to carbon atom in X

24
G is bonded to H
through nitrogen

1

Compounds of Formula 1 wherein a nitrogen in X is linked via v to a carbon atom in G can be prepared by reaction of a compound of Formula 25 with a heterocyclic compound of Formula 26 wherein $Y^6$ is a leaving group (e.g., bromide, iodide, mesylate ($OS(O)_2CH_3$), triflate ($OS(O)_2CF_3$) and the like) as shown in Scheme 17. The reaction can be carried out in the presence of a base such as potassium carbonate in a solvent such as dimethylsulfoxide, N,N-dimethylformamide or acetonitrile at temperatures between about 0 to 80° C. Compounds of Formula 26 can be prepared from corresponding compounds wherein $Y^6$ is OH by methods known to one skilled in the art.

Scheme 17

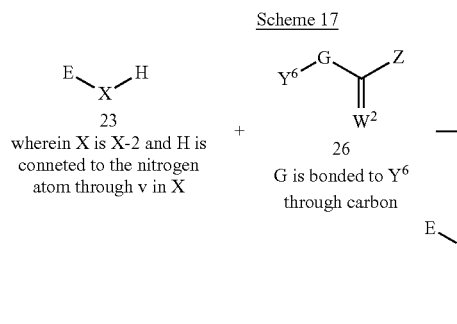

Compounds of Formula 1 can also be prepared by reaction of a suitably functionalized compound of Formula 27 with a suitably functionalized compound of Formula 28 as shown in Scheme 18. The functional groups $Y^7$ and $Y^8$ are selected from, but not limited to, moieties such as aldehydes, ketones, esters, acids, amides, thioamides, nitriles, amines, alcohols, thiols, hydrazines, oximes, amidines, amideoximes, olefins, acetylenes, halides, alkyl halides, methanesulfonates, trifluoromethanesulfonates, boronic acids, boronates, and the like, which under the appropriate reaction conditions, will allow the construction of the various heterocyclic rings G. As an example, reaction of a compound of Formula 27 where $Y^7$ is a thioamide group with a compound of Formula 28 where $Y^8$ is a bromoacetyl group will give a ketone of Formula 29 where G is a thiazole ring.

The synthetic literature describes many general methods for forming 5-membered heteroaromatic rings (e.g., G-1 through G-48); see, for example, *Comprehensive Heterocyclic Chemistry*, Vol. 4-6, A. R. Katritzky and C. W. Rees editors, Pergamon Press, New York, 1984; *Comprehensive Heterocyclic Chemistry II*, Vol. 2-4, A. R. Katritzky, C. W. Rees, and E. F. Scriven editors, Pergamon Press, New York, 1996; and the series, *The Chemistry of Heterocyclic Compounds*, E. C. Taylor, editor, Wiley, New York. One skilled in the art knows how to select the appropriate functional groups to construct the desired heterocyclic ring G. Compounds of Formula 28 are known or can be prepared by methods known in the art.

Scheme 18

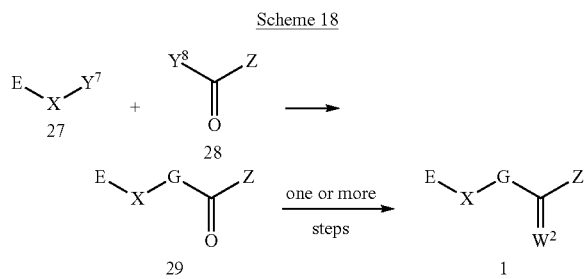

Compounds of Formula 1 where G is bonded to C(=W²)Z through a G ring nitrogen can also be prepared by displacement of an appropriate leaving group $Y^9$ on C(=W²)Z of Formula 31 with a compound of Formula 30 in the presence of a base as depicted in Scheme 19. Suitable bases include triethylamine or N,N-diisopropylethylamine and the reaction is carried out in a solvent such as ethanol or tetrahydrofuran at temperatures between about 0 to 80° C. Suitable leaving groups in the compounds of Formula 31 include, for example, chlorine, bromide and the like. Compounds of Formula 31 can be prepared from corresponding compounds wherein $Y^9$ is H by halogenation with a chlorinating such as N-chlorosuccinimide in a solvent such at acetonitrile or N,N-dimethylformamide at temperatures between 0 and 100° C. Compounds of Formula 31 can also be prepared by additional methods known in the art; see, for example, *Comprehensive Organic Functional Group Transformation*, Vol. 5, A. R. Katritzky, O. Meth-Cohn, and C. W. Rees editors, Elsevier Science Inc., New York, 1995, (e.g. hydroxamoyl halides, pages 664-674 and hydrazonyl halides, pages 675-682).

Scheme 19

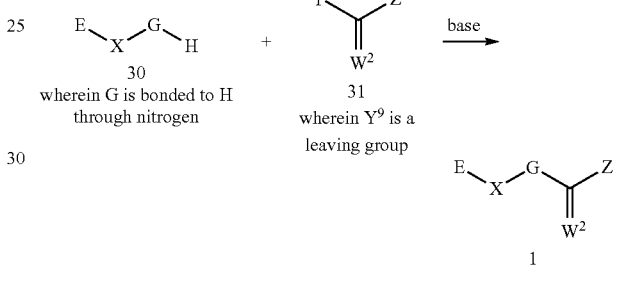

As shown in Scheme 20, compounds of Formula 1 can also be prepared by reacting compounds of Formula 32 with nucleophiles of Formula 33 where a heteroatom in Z is linked to the hydrogen shown in HZ. Reaction conditions and preparation of compounds of Formula 32 are analogous to those described for Scheme 19 above.

Many of the nucleophiles of Formula 33 are known or can be prepared by general methods known in the art.

Scheme 20

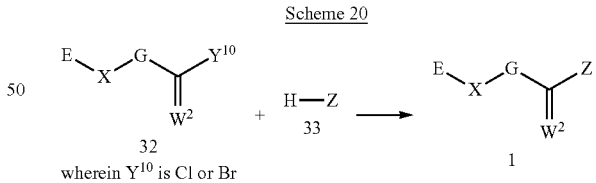

Oximes and hydrazones of Formula 1 as shown in Scheme 21 can readily be prepared by methods known to one skilled in the art. For example, oximes of Formula 1 when W² is NOR¹² can be prepared by reacting the corresponding-substituted hydroxylamine or hydroxylamine hydrochloride 34 with a ketone 29 where Z is a carbon linked fragment other than H or an aldehyde 29 where Z is H. These reactions are typically run at 0-80° C. in a solvent such as ethanol or tetrahydrofuran in the presence of a base such as triethylamine or pyridine; see, for example, PCT Patent Publication WO 2008/006874. One skilled in the art will recognize that mixtures of syn and anti isomers may result.

Scheme 21

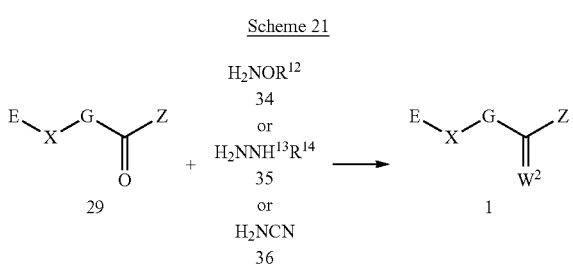

Hydrazones of Formula 1, when $W^2$ is $NNR^{13}R^{14}$ can similarly be prepared by heating an aldehyde 29 wherein is Z is H or a ketone 29 wherein Z is a carbon linked fragment other than H with a hydrazine or a substituted hydrazine in a solvent such as ethanol or tetrahydrofuran; see for example, A. J. Turbiak and H. D. H. Showalter, *Synthesis* 2009, 23, 4022-4026.

The reactions can also be carried out in the presence of an acid; see for example, R. Kulandasamy et al., *European Journal of Medicinal Chemistry* 2009, 44(11), 4376-4384. Many additional methods are known to one skilled in the art which can be used to prepare the oximes and hydrazones Formula 1; see, for example, *Comprehensive Organic Functional Group Transformation*, Vol. 3, A. R. Katritzky, O. Meth-Cohn, and C. W. Rees editors, Elsevier Science Inc., New York, 1995, (e.g. oximes, pages 425-429 and hydrazones, pages 444-448).

Many of the compounds of Formulas 34, 35, and 36 are commercially available. In addition, many general methods are described in the synthetic literature for preparing the compounds of Forumlas 34 and 35; see, for example, *Comprehensive Organic Functional Group Transformation*, Vol. 2, A. R. Katritzky, O. Meth-Cohn, and C. W. Rees editors, Elsevier Science Inc., New York, 1995, (e.g. hydroxyamines 34, pages 102-103 and hydrazines 35, pages 373-376).

The methods described in PCT Patent Publication WO 2009/055514 to prepare aldehydes of Formula 29a wherein Z is H and ketones of Formula 29b wherein Z is $CH_3$ and references cited therein are particularly useful to prepare the compounds of Formula 29.

The α, β unsaturated ketones of Formula 29c are also particularly useful. They are prepared by reacting a methyl ketone of Formula 29b with an aldehyde of Formula 37 in the presence a mild Lewis Acid catalyst such as basic alumina; see, for example R. S. Varma, et. al. *Synthetic Communication* 1985, 15(4), 279-284 and references cited therein. The reactions can be carried out neat or in a chlorinated solvent such as dichloromethane. This method is exemplified in Example 2, Step A.

Scheme 22

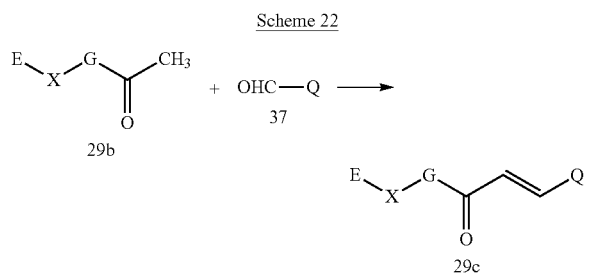

The compounds of Formula 1i wherein $W^2$ is $NOR^{12}$ and Z is $CH_2CH(OH)Q$ can be prepared in three steps as outlined in Scheme 23. In a modified Mukaiyama aldol reaction a ketone of Formula 29b is reacted with an aldehyde of Formula 37 in the presence of a silylating agent such as 1,1,1-trifluoromethane sulfonic acid, (1,1-dimethylethyl)dimethylsilyl ester and a mild base such as N-ethyl-N-(1-methylethyl)-2-propane amine; see, for example, C. W. Downey *J. Org. Chem.* 2008, 73(8), 3299-3302. The intermediate silyl alcohol of Formula 29d is converted to an oxime as described in Scheme 23. The O silyl protecting group is then removed with a fluoride source such as tetra-n-butylammonium fluoride to provide compounds of Formula 1i. A detailed description of these transformations can be found in synthesis Example 6 below.

Scheme 23

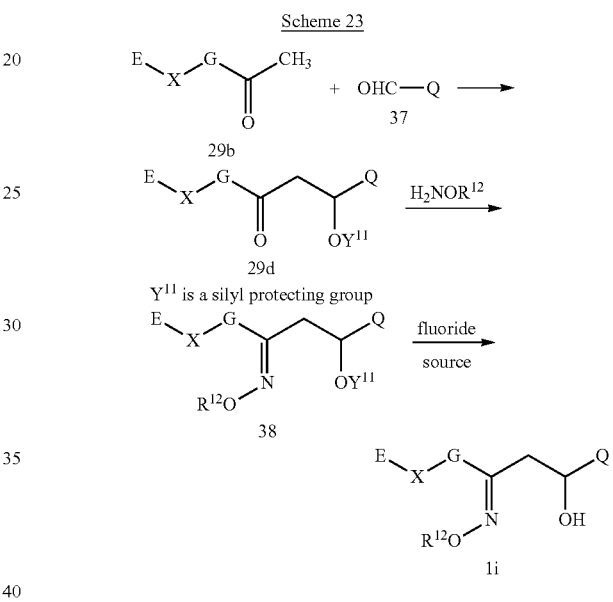

As the synthetic literature includes many ketone-forming methods, the synthetic procedures of Schemes 21, 22 and 23 are simply representative examples of a wide variety of methods useful for the preparation the ketones of Formula 29.

One skilled in the art will also recognize that compounds of Formula 1 where $W^2$ is $NOR^{12}$ or $NNR^{13}R^{14}$ wherein $R^{12}$ is H and one or both of $R^{13}R^{14}$ are H can be subjected to various electrophilic, nucleophilic, radical, organometallic, oxidation, and reduction reactions to add substituents or modify existing substituents as shown in Scheme 24. Example of acylation wherein $W^2$ is NO(C=O)Me and alkylation wherein $W^2$ is $NOCH_2CH_2C_6H_5$ are described in synthesis Example 3 and Example 1 Step F respectively below.

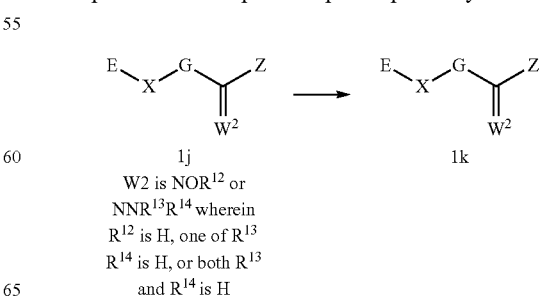

1j
W2 is $NOR^{12}$ or
$NNR^{13}R^{14}$ wherein
$R^{12}$ is H, one of $R^{13}$
$R^{14}$ is H, or both $R^{13}$
and $R^{14}$ is H 1k Amines of Formula 3 can be prepared from compounds of Formula 39 wherein $Y^{12}$ is an amine protecting group via a deprotection reaction as shown in Scheme 25. A wide array of amine protecting groups are suitable for the method of Scheme 25 (see, for example, T. W. Greene and P. G. M. Wuts, *Protective Groups in Organic Synthesis,* 2nd ed.; Wiley: New York, 1991), and the choice of the appropriate protecting groups will be apparent to one skilled in chemical synthesis. After deprotection, the amine of Formula 3 can be isolated as its acid salt or the free amine by general methods known in the art.

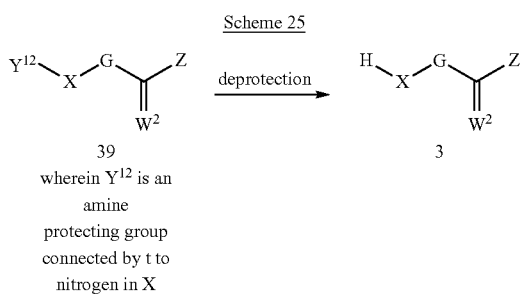

One skilled in the art will recognize that many compounds of Formula 39 can be prepared by methods analogous to those described in Schemes 16 through 23 above where the group E is replaced by $Y^{12}$. Thus, compounds corresponding to Formulae 23, 25, 27, 29, 29a, 29b, 29c, 30 and 32 in which E is replaced by $Y^{12}$ are useful intermediates for the preparation of compounds of Formula 1.

Thioamides of Formula 40 are particularly useful intermediates for preparing compounds of Formula 1 and 39. A thioamide of Formula 40 can be prepared by the addition of hydrogen sulfide to the corresponding nitrile of Formula 41 wherein $Y^{13}$ is a nitrile moiety connected to carbon at v in X as shown in Scheme 26. The methods of Scheme 26 can be carried out by contacting a compound of Formula 41 with hydrogen sulfide in the presence of an amine such as pyridine, diethylamine or diethanolamine. Alternatively, hydrogen sulfide can be used in the form of its bisulfide salt with an alkali metal or ammonia. This type of reaction is well documented in the literature see; for example, European Patent EP 696581.

As also shown in Scheme 26, a thioamide of Formula 40 can be prepared by the reaction of a compound of Formula 41 (wherein $Y^{13}$ is H and connected to nitrogen at v in X) is contacted with thiocarbonyl diimidazole followed by treatment with ammonia as described by J. L. Collins, et. al., *J. Med. Chem.* 1998, 41(25), 5037-5054.

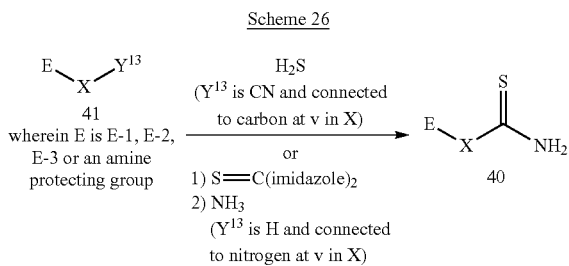

The core 6-membered and 7-membered heterocyclic ring systems depicted in the above Schemes (X in Formula 1) are known or can be prepared by methods known to one skilled in the art. The synthetic literature describes many general methods for forming saturated and partially unsaturated 6- and 7-membered heterocyclic ring systems. See, for example, *Comprehensive Heterocyclic Chemistry*, Vol. 3 and 7, A. R. Katritzky and C. W. Rees editors, Pergamon Press, New York, 1984; *Comprehensive Heterocyclic Chemistry II*, Vol. 6 and 9, A. R. Katritzky, C. W. Rees, and E. F. Scriven editors, Pergamon Press, New York, 1996; and the series, *The Chemistry of Heterocyclic Compounds*, E. C. Taylor, editor, Wiley, New York. In addition, numerous specific examples of many of these ring systems can be found in the original synthetic literature via structure searches using electronic databases such as Scifinder and Bielstein as known to one skilled in the art. One skilled in the art will know how to select the appropriate protecting groups and functional groups to construct the desired heterocyclic rings.

For example, the intermediate cyano compound 41a wherein the core heterocycle is a hexahydropyridazine (e.g., X-5) can be prepared by a three step sequence outlined in Scheme 27. The tetrahydropyridazine 42 is hydroxylated in the presence of mercuric acetate to give compound 43 (see Vartanyan, R. S. et al. *Armyanskii Khimicheskii Zhurnal* 1991, 44(4), 259). The hydroxyl group in compound 43 can be converted into its corresponding mesylate and displaced with a cyanide anion using standard methods to give compound 41a.

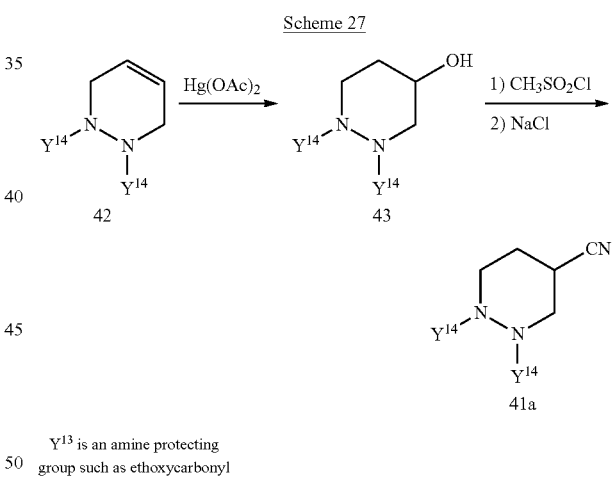

In a second example, the intermediate cyano compound 41b wherein the core heterocycle is a tetrahydro-1,2-oxazine (e.g., X-4) can be prepared in eight steps as outlined in Scheme 28. The primary hydroxyl groups of triol 44 are protected, the secondary hydroxyl group is mesylated and displaced by cyanide followed by deprotection to give cyanodiol 46. Mesylation followed by base treatment gives olefin 47 and the mesyl group is displaced by an O,N di-protected hydroxylamine. The O protecting group can be removed followed by base catalyzed cyclization to provide a compound of Formula 41b.

Scheme 28

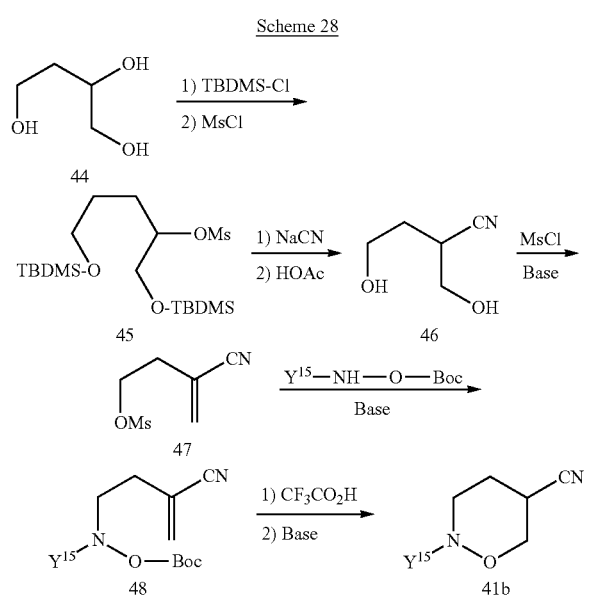

$Y^{15}$ is an amine protecting group such as ethoxycarbonyl
Ms is CH$_3$SO$_2$Cl Alternatively, tetrahydro-1,2-oxazines (e.g. X-4) can be prepared by cycloaddition of nitrosyl hydride or nitrosoformaldehyde with substituted dienes as described by Ensley, H. E. and Mahadevan, S., *Tetrahedron Lett.* 1989, 30(25), 3255, or by reaction of substituted 1,4-dibromobutanes with N-hydroxyurethane as described by Riddell, F. G. and Williams, D. A. R., *Tetrahedron* 1974, 30(9), 1083.

It is recognized that some reagents and reaction conditions described above for preparing compounds of Formula 1 may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis*, 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula 1. One skilled in the art will also recognize that it may be necessary to perform a combination of the steps illustrated in the above schemes in an order other than that implied by the particular sequence presented to prepare the compounds of Formula 1.

One skilled in the art will also recognize that compounds of Formula 1 and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Examples are, therefore, to be construed as merely illustrative, and not limiting of the disclosure in any way whatsoever. Steps in the following Examples illustrate a procedure for each step in an overall synthetic transformation, and the starting material for each step may not have necessarily been prepared by a particular preparative run whose procedure is described in other Examples or Steps. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane; "s" means singlet, "d" means doublet, "t" means triplet, "q" means quartet, "m" means multiplet, "dd" means doublet of doublets, "dt" means doublet of triplets, "br s" means broad singlet.

Example 1

Preparation of 2-[5-methyl-3-(trifluoromethyl)-1H-pyrazol-1-yl]-1-[4-[4-[-1-[(2-phenethylethoxy)imino]ethyl]-2-thiazolyl]-1-piperidinyl]ethanone Step A: Preparation of 1-(2-chloroacetyl)-4-piperidinecarbonitrile A mixture of 4-piperidinecarbonitrile (200 g, 1.80 mol) and 40% aqueous potassium carbonate solution (342 g, 0.99 mol) in dichloromethane (1 L) was cooled to –10° C., and a solution of chloroacetyl chloride (210 g, 1.86 mol) in dichloromethane (300 mL) was added over about 75 minutes while maintaining the reaction mixture at –10 to 0° C. After the addition was complete, the reaction mixture was separated, the upper aqueous phase was extracted with dichloromethane (2×300 mL), and the combined organic phases were concentrated under reduced pressure to give 312 g of the title compound as a liquid which slowly crystallized on standing. This compound was of sufficient purity to use in subsequent reactions.

$^1$H NMR (CDCl$_3$): δ 1.8-2.1 (m, 4H), 2.95 (m, 1H), 3.5-3.8 (m, 4H), 4.08 (q, 2H).

Step A1: Alternative Preparation of 1-(2-chloroacetyl)-4-piperidinecarbonitrile

A solution of N-(1,1-dimethylethyl)-4-piperidinecarboxamide (201 g, 1.0 mol) in dichloromethane (1 L) was cooled under nitrogen to 5° C., and chloroacetyl chloride (124 g, 1.1 mol) in 300 mL of dichloromethane was added dropwise over 30 minutes while maintaining the reaction mixture at 0 to 5° C. Then 20% aqueous potassium carbonate solution (450 g, 0.65 mol) was added dropwise over 30 minutes while keeping reaction temperature between 0 and 5° C. The reaction mixture was stirred for an additional 30 minutes at 0° C., and then allowed to warm to room temperature. The layers were separated, and the aqueous layer was extracted with dichloromethane (200 mL). The combined dichloromethane layers were concentrated under reduced pressure to yield a solid, which was triturated with 400 mL of hexanes. The slurry was filtered, and the filter cake was washed with 100 mL of hexanes and dried in a vacuum oven overnight at 50° C. to give 185.5 g of 1-(2-chloroacetyl)-N-(1,1-dimethylethyl)-4-piperidinecarboxamide as a solid, melting at 140.5-141.5° C.

$^1$H NMR (CDCl$_3$): δ 1.35 (s, 9H), 1.6-2.0 (m, 4H), 2.25 (m, 1H), 2.8 (t, 1H), 3.2 (t, 1H), 3.9 (d, 1H), 4.07 (s, 2H), 4.5 (d, 1H), 5.3 (br s, 1H).

To a solution of 1-(2-chloroacetyl)-N-(1,1-dimethylethyl)-4-piperidinecarboxamide (26.1 g, 0.10 mol) in N,N-dimethylformamide (35 mL) was added phosphorus oxychloride (18.8 g, 0.123 mol) dropwise over 30 minutes while allowing the temperature of the reaction mixture to rise to 37° C. The reaction mixture was heated at 55° C. for 1 h and then was slowly added to water (about 150 g) cooled with ice to maintain a temperature of about 10° C. The pH of the reaction mixture was adjusted to 5.5 with 50% NaOH aqueous solution. The mixture was extracted with dichloromethane (4×100 mL), and the combined extract was concentrated under reduced pressure to give 18.1 g of the title compound as a solid. This compound was of sufficient purity to use in subsequent reactions.

Step B: Preparation of 1-[2-[5-methyl-3-(trifluoromethyl)-1H-pyrazol-1-yl]acetyl]-4-piperidinecarbonitrile A solution of 3-methyl-5-trifluoromethylpyrazole (9.3 g, 62 mmol) and 45% aqueous potassium hydroxide solution (7.79 g, 62 mmol) in N,N-dimethylformamide (25 mL) was cooled to 5° C., and 1-(2-chloroacetyl)-4-piperidinecarbonitrile (i.e. the product of Example 1, Step A or A1) (11.2 g, 60 mmol) was added. The reaction mixture was stirred for 8 h at 5-10° C., then diluted with water (100 mL), and filtered. The filter cake was washed with water and dried at 50° C. in a vacuum-oven to give 15 g of the title compound as a solid containing 3% of its regioisomer, i.e. 1-[2-[3-methyl-5-(trifluoromethyl)-1H-pyrazol-1-yl]acetyl]-4-piperidinecarbonitrile.
$^1$H NMR (CDCl$_3$): δ 1.88 (m, 4H), 2.32 (s, 3H), 2.95 (m, 1H), 3.7 (m, 4H), 5.0 (q, 2H), 6.34 (s, 1H).

Step C: Preparation of 1-[2-[5-methyl-3-(trifluoromethyl)-1H-pyrazol-1-yl]acetyl]-4-piperidinecarbothioamide Hydrogen sulfide gas was passed into a solution of 1-[2-[5-methyl-3-(trifluoromethyl)-1H-pyrazol-1-yl]acetyl]-4-piperidinecarbonitrile (i.e. the product of Example 1, Step B) (9.0 g, 30 mmol) and diethanolamine (3.15 g, 30 mmol) in N,N-dimethylformamide (15 mL) at 50° C. in a flask equipped with dry-ice condenser. The hydrogen sulfide feed was stopped when the reaction mixture became saturated with hydrogen sulfide, as indicated by condensation on the cold-finger. The reaction mixture was stirred for an additional 30 minutes at 50° C. Then excess hydrogen sulfide gas was sparged into the scrubber by a subsurface nitrogen flow, and water (70 mL) was gradually added. The reaction mixture was cooled to 5° C., filtered, and washed with water (2×30 mL). The filter cake was dried at 50° C. in a vacuum-oven to give 8.0 g of the title compound as a solid, melting at 185-186° C.
$^1$H NMR (CDCl$_3$): δ 1.7 (m, 2H), 2.0 (m, 2H), 2.29 (m, 3H), 2.65 (t, 1H), 3.0 (m, 1H), 3.2 (t, 1H), 4.0 (d, 1H), 4.6 (d, 1H), 4.96 (d, 1H), 5.4 (d, 1H), 6.35 (s, 1H), 7.4 (br s, 1H), 7.5 (br s, 1H).

Step D: Preparation of 1-[4-(4-acetyl-2-thiazolyl)-1-piperidinyl]-2-[5-methyl-3-trifluoromethyl)-1H-pyrazol-1-yl)ethanone A mixture of 1-bromobutane-2,3-dione (12.4 g, 75.2 mmol) and 1-[2-[5-methyl-3-(trifluoromethyl)-1H-pyrazol-1-yl]acetyl]-4-piperidinecarbothioamide (i.e. the product of Example 1, Step C) (20.0 g, 59.8 mmol) in methanol (300 mL) was stirred overnight at room temperature. The reaction was concentrated under reduced pressure and the resulting residue triturated with hexanes and diethyl ether, filtered and air dried. This solid was partitioned between dichloromethane and saturated sodium bicarbonate. The organic phase was separated, dried over magnesium sulfate, filtered and concentrated to give a thick oil. This oil was triturated with hexanes and diethyl ether to provide 23.1 g of the title compound as a solid.
$^1$H NMR (CDCl$_3$): δ 1.73-1.90 (m, 2H), 2.14-2.28 (m, 2H), 2.33 (s, 3H), 2.64 (s, 3H), 2.81-3.00 (m, 1H), 3.32 (br s, 2H), 3.95-4.15 (m, 1H), 4.50-4.69 (m, 1H), 5.00 (m, 2H) 6.34 (s, 1H), 8.05 (s, 1H).

Step E: Preparation of 1-[4-[4-[1-(hydroxyimino) ethyl)-2-thiazolyl]-1-piperidinyl]-2-[5-methyl-3-(trifluoromethyl)-1H-pyrazol-1-yl]ethanone A mixture of 1-[4-(4-acetyl-2-thiazolyl)-1-piperidinyl]-2-[5-methyl-3-trifluoromethyl)-1H-pyrazol-1-yl)ethanone (i.e. the product of Example 1, Step D) (4.5 g, 11.25 mmol) and hydroxylamine hydrochloride (0.945 g, 13.5 mmol) in methanol (60 mL) was heated at reflux for 6 h. The reaction mixture was concentrated under reduced pressure and partitioned between saturated sodium bicarbonate and dichloromethane. The organic phase was separated and the aqueous phase was extracted two additional times with dichloromethane. The organic phases were combined, washed with saturated sodium chloride, dried over magnesium sulfate, filtered, and concentrated to provide 4.2 g of the title compound.
$^1$H NMR (CDCl$_3$): δ 1.55 (s, 3H), 1.72-1.85 (m, 2H), 2.13-2.28 (m, 2H), 2.32 (s, 3H), 2.78-2.94 (m, 1H), 3.22-3.38 (m, 2H), 4.05 (d, 1H), 4.59 (d, 1H), 4.99 (dd, 2H), 6.34 (s, 1H), 7.33 (br. s, 1H), 7.43 (s, 1H).

Step F: Preparation of 2-[5-methyl-3-(trifluoromethyl)-1H-pyrazol-1-yl]-1-[4-[4-[-1-[(2-phenethylethoxy)imino]ethyl]-2-thiazolyl]-1-piperidinyl]ethanone A mixture of 1-[4-[4-[1-(hydroxyimino)ethyl)-2-thiazolyl]-1-piperidinyl]-2-[5-methyl-3-(trifluoromethyl)-1H-pyrazol-1-yl]ethanone (0.5 g, 1.2 mmol) (i.e. the product of Example 1, Step E), (2-bromoethyl)benzene (0.277 g, 1.5 mmol), and cesium carbonate (0.487 g, 1.5 mmol) in acetonitrile (6 mL) was heated at 60° C. overnight, diluted with dichloromethane, and filtered through a fritted SPE tube (Varian® bond elute reservoir). The reaction was concentrated under reduced pressure and the resulting residue purified via silica gel chromatography (hexanes: ethyl acetate gradient) to provide 0.17 g of the title compound.
$^1$H NMR (CDCl$_3$): δ 1.77 (m, 2H), 2.10-2.38 (m, 8H), 2.80-2.95 (m, 1H), 3.04 (t, 2H), 3.30 (m, 2H), 4.02 (d, 1H), 4.42 (t, 2H), 4.58 (d, 1H), 4.99 (dd, 2H), 6.33 (s, 1H), 7.15-7.38 (m, 5H), 7.46 (s, 1H).

Example 2

Preparation of 3-(2,6-difluorophenyl)-1-[2-[1-[2-[5-methyl-3-(trifluoromethyl)-1H-pyrazol-1-yl]acetyl]-4-piperidinyl]-4-thiazolyl]-2-propen-1-one 1-oxime Step A: Preparation of 3-(2,6-difluorophenyl)-1-[2-[1-[2-[5-methyl-3-(trifluoromethyl)-1H-pyrazol-1-yl]acetyl]-4-piperidinyl]-4-thiazolyl]-2-propen-1-one To a solution of 1-[4-(4-(4-acetyl-2-thiazolyl)-1-piperidinyl]-2-[5-methyl-3-trifluoromethyl)-1H-pyrazol-1-yl)ethanone (i.e. the product of Example 1, Step D) (1.0 g, 2.5 mmol) in dichloromethane (20 mL) was added 2,6-difluorobenzaldehyde (0.45 g, 4.25 mmol), followed by of powdered basic alumina (7.7 g, 75 mmol). The reaction mixture was heated at reflux for 20 h. Upon cooling, the suspended solid was collected by filtration and washed with dichloromethane. The filtrate was concentrated under reduced pressure and the resulting oil further purified by flash column chromatography on silica gel (1:1 hexanes/ethyl acetate) to provide the 847 mg of the title compound (a compound of Formula 1A) as a solid foam.

$^1$H NMR (CDCl$_3$): δ 1.75-1.94 (m, 2H), 2.17-2.31 (m, 2H), 2.34 (s, 3H), 2.87-3.05 (m, 1H), 3.28-3.42 (m, 2H), 4.02-4.17 (m, 1H), 4.52-4.66 (m, 1H), 4.91-5.09 (m, 2H), 6.34 (s, 1H), 6.91-7.04 (m, 2H), 7.20-7.41 (m, 1H), 7.96-8.16 (m, 2H), 8.21 (s, 1H).

Step B: Preparation of 3-(2,6-difluorophenyl)-1-[2-[1-[2-[5-methyl-3-(trifluoromethyl)-1H-pyrazol-1-yl]acetyl]-4-piperidinyl]-4-thiazolyl]-2-propen-1-one 1-oxime A solution of 3-(2,6-difluorophenyl)-1-[2-[1-[2-[5-methyl-3-(trifluoromethyl)-1H-pyrazol-1-yl]acetyl]-4-piperidinyl]-4-thiazolyl]-2-propen-1-one (i.e. the product of Example 2, Step A) (0.5 g, 0.93 mmol) and hydroxylamine hydrochloride (0.078 g, 1.14 mmol) in methanol (10 mL) was heated at reflux for 2 h. The reaction mixture was concentrated under reduced pressure and partitioned between dichloromethane and saturated sodium bicarbonate. The mixture was poured onto a Celite® extraction tube (ChemElute® diatomaceous earth-based liquid-liquid exchange cartridge), eluted with dichloromethane and concentrated to provide 0.5 g of the title compound.

$^1$H NMR (CDCl$_3$): δ 1.74-1.96 (m, 2H), 2.15-2.40 (m, 5H), 2.84-3.05 (m, 1H), 3.35 (d, 2H), 3.99-4.15 (m, 1H), 4.51-4.65 (m, 2H), 4.91-5.12 (m, 2H), 6.34 (br s, 1H), 6.83-7.04 (m, 2H), 7.17-7.54 (m, 3H), 7.78-8.26 (m, 2H).

Example 3

Preparation of 3-(2,6-difluorophenyl)-1-[2-[1-[2-[5-methyl-3-(trifluoromethyl)-1H-pyrazol-1-yl]acetyl]-4-piperidinyl]-4-thiazolyl]-2-propen-1-one 1-(O-acetyloxime)

A solution of 3-(2,6-difluorophenyl)-1-[2-[1-[2-[5-methyl-3-(trifluoromethyl)-1H-pyrazol-1-yl]acetyl]-4-piperidinyl]-4-thiazolyl]-2-propen-1-one 1-oxime (i.e. the product of Example 2, Step B) (0.10 g, 0.189 mmol), acetyl chloride (0.017 g, 0.22 mmol) and triethylamine (0.022 g, 0.22 mmol) in dichloromethane (5 mL) was stirred for 2 hr and shaken with 1 mL of 1 N hydrochloric acid. The mixture was poured onto a Celite® extraction tube, eluted with dichloromethane and concentrated to give 0.11 g of crude material which was purified via silica gel chromatography (hexanes-ethyl acetate gradient) to provide 0.11 g of the title compound.

$^1$H NMR (CDCl$_3$): δ 1.53-1.67 (m, 1H), 1.75-1.93 (m, 2H), 2.11-2.44 (m, 6H), 2.93 (t, 1H), 3.25-3.44 (m, 2H), 3.93-4.20 (m, 1H), 4.44-4.66 (m, 1H), 5.00 (s, 2H), 6.33 (s, 1H), 6.83-7.05 (m, 2H), 7.17-7.38 (m, 2H), 7.44 (d, 1H), 7.69-7.90 (m, 2H).

Example 4

Preparation of 3-(2,6-difluorophenyl)-1-[2-[1-[2-[5-methyl-3-(trifluoromethyl)-1H-pyrazol-1-yl]acetyl]-4-piperidinyl]-4-thiazolyl]-2-propen-1-one 1-(O-methyloxime)

A mixture of 3-(2,6-difluorophenyl)-1-[2-[1-[2-[5-methyl-3-(trifluoromethyl)-1H-pyrazol-1-yl]acetyl]-4-piperidinyl]-4-thiazolyl]-2-propen-1-one (i.e. the product of Example 2, Step A) (0.25 g, 0.48 mmol) and methoxyamine hydrochloride (0.047 g, 0.58 mmol) in methanol (10 mL) was heated overnight at 60° C. The reaction was concentrated under reduced pressure, partitioned between dichloromethane and saturated sodium bicarbonate. The mixture was eluted from a Celite® extraction tube (ChemElute® diatomaceous earth-based liquid-liquid exchange cartridge) with dichloromethane and concentrated to provide 0.26 g of the title compound.

$^1$H NMR (CDCl$_3$): δ 1.85 (m, 2H), 2.10-2.41 (m, 5H), 2.85-3.05 (m, 1H), 3.33 (m, 2H), 3.94-4.16 (m, 4H), 4.47-4.61 (m, 1H), 4.99 (br s, 2H), 6.33 (br s, 1H), 6.91 (br s, 2H), 7.12-7.35 (m, 2H), 7.47-7.60 (m, 1H), 7.69-8.05 (m, 1H).

Example 5

Preparation of 3-(2,6-difluorophenyl)-1-[2-[1-[2-[5-methyl-3-(trifluoromethyl)-1H-pyrazol-1-yl]acetyl]-4-piperidinyl]-4-thiazolyl]-1-propanone 1-oxime A mixture of 3-(2,6-difluorophenyl)-1-[2-[1-[2-[5-methyl-3-(trifluoromethyl)-1H-pyrazol-1-yl]acetyl]-4-piperidinyl]-4-thiazolyl]-2-propen-1-one (i.e. the product of Example 2, Step A) (0.25 g, 0.48 mmol), zinc dust (0.25 g, 3.8 mmol) and saturated ammonium chloride (0.25 mL) in ethanol (5 mL) was stirred overnight, concentrated to dryness, treated with dichloromethane and filtered. The filtrate was concentrated and purified via silica gel chromatography (hexanes: ethyl acetate gradient) to provide 0.025 g of 3-(2,6-difluorophenyl)-1-[2-[1-[2-[5-methyl-3-(trifluoromethyl)-1H-pyrazol-1-yl]acetyl]-4-piperidinyl]-4-thiazolyl]-1-propanone.

This intermediate was taken up in 2 mL of methanol and treated with 5 drops of 50% aqueous hydroxylamine. The solution was heated at 60° C. for 30 minutes and concentrated under reduced pressure to give 0.025 g of the title compound.

$^1$H NMR (CDCl$_3$): δ 1.82 (br s, 2H), 2.11-2.27 (m, 2H), 2.27-2.39 (m, 3H), 2.84-3.18 (m, 5H), 3.31 (d, 2H), 4.03 (d, 1H), 4.52 (d, 1H), 4.90-5.11 (m, 2H), 6.34 (s, 1H), 6.77-6.91 (m, 2H), 7.14 (m, 1H), 7.44 (s, 1H), 8.10 (br s, 1H).

Example 6

Preparation of 3-(2,6-difluorophenyl)-3-hydroxy-1-[2-[1-[2-[5-methyl-3-(trifluoromethyl)-1H-pyrazol-1-yl]acetyl]-4-piperidinyl]-4-thiazolyl]-1-propanone 1-oxime Step A: Preparation of 3-(2,6-difluorophenyl)-3-[[(1,1-dimethylethyl)dimethylsilyl]oxy]-1-[2-[1-[2-[5-methyl-3-(trifluoromethyl)-1H-pyrazol-1-yl]acetyl]-4-piperidinyl]-4-thiazolyl]-1-propanone 1-oxime To a solution of 2,6-difluorobenzaldehyde (0.177 g, 1.25 mmol) in dichloromethane (5 mL) was added N-ethyl-N-(1-methylethyl)-2-propane amine (0.436 ml, 2.5 mmol) and 1,1,1-trifluoro-methanesulfonic acid, (1,1-dimethylethyl)dimethylsilyl ester (0.430 mL, 1.875 mmol). The reaction was stirred for 15 minutes and a solution of 1-[4-(4-acetyl-2-thiazolyl)-1-piperidinyl]-2-[5-methyl-3-(trifluoromethyl)-1H-pyrazol-1-yl)ethanone (i. e. the product of Example 1, Step D) (0.5 g, 1.25 mmol) dissolved in dichloromethane (2 mL) was added dropwise over 5 minutes. The resulting reaction was stirred for 6 hours and concentrated under reduced pressure. The residue was purified via silica gel chromatography (20% ethyl acetate: hexanes to 100% ethyl acetate eluant) to provide 0.62 g of the title compound.

$^1$H NMR (CDCl$_3$): δ −0.17 (s, 3H), −0.04 (s, 3H), 0.74 (s, 9H), 1.73-1.93 (m, 2H), 2.12-2.28 (m, 2H), 2.34 (s, 3H), 2.87-3.06 (m, 1H), 3.21-3.43 (m, 3H), 3.91-4.09 (m, 2H), 4.47-4.64 (m, 1H), 4.92-5.10 (m, 2H), 5.74-5.89 (m, 1H), 6.40 (s, 1H), 6.79-6.95 (m, 2H), 7.17-7.26 (m, 1H), 8.08 (s, 1H).

Step B: Preparation of 3-(2,6-difluorophenyl)-3-[[(1, 1-dimethylethyl)dimethylsilyl]oxy]-1-[2-[1-[2-[5-methyl-3-(trifluoromethyl)-1H-pyrazol-1-yl]acetyl]-4-piperidinyl]-4-thiazolyl]-1-propanone 1-oxime To a solution of 3-(2,6-difluorophenyl)-3-[[(1,1-dimethylethyl)dimethylsilyl]oxy]-1-[2-[1-[2-[5-methyl-3-(trifluoromethyl)-1H-pyrazol-1-yl]acetyl]-4-piperidinyl]-4-thiazolyl]-1-propanone 1-oxime (i. e. the product of Example 6, Step A) (0.62 g, 0.945 mmol) in methanol (10 ml) was added 50% aqueous hydroxylamine (4.26 mmol). The reaction was heated at reflux for 4 hours and concentrated under reduced pressure. The resulting oily residue was dissolved in dichloromethane, dried over magnesium sulfate, filtered, and concentrated to give 0.6 g of title product. This compound was of sufficient purity to use in subsequent reactions.

$^1$H NMR (CDCl3): δ −0.22 to −0.19 (m, 3H), −0.13 (s, 3H), 0.69 (s, 9H), 1.70-1.88 (m, 2H), 2.12-2.28 (m, 2H), 2.34 (s, 3H), 2.86-2.96 (m, 1H), 3.26-3.39 (m, 3H), 3.45-3.57 (m, 2H), 3.99-4.10 (m, 1H), 4.52-4.62 (m, 1H), 5.01 (s, 2H), 5.63-5.72 (m, 1H), 6.35 (s, 1H), 6.78-6.90 (m, 2H), 7.14-7.24 (m, 1H), 7.54 (s, 1H).

Step C: Preparation of 3-(2,6-difluorophenyl)-3-hydroxy-1-[2-[1-[2-[5-methyl-3-(trifluoromethyl)-1H-pyrazol-1-yl]acetyl]-4-piperidinyl]-4-thiazolyl]-1-propanone 1-oxime To a solution of 3-(2,6-difluorophenyl)-3-[[(1,1-dimethylethyl)dimethylsilyl]oxy]-1-[2-[1-[2-[5-methyl-3-(trifluoromethyl)-1H-pyrazol-1-yl]acetyl]-4-piperidinyl]-4-thiazolyl]-1-propanone 1-oxime (i.e. the product of Example 6, Step B) (0.25 g, 0.37 mmol) in tetrahydrofuran (5 mL) was added a 1 M solution of tetra-n-butylammonium fluoride in tetrahydrofuran (0.55 mL). The resulting solution was stirred at room temperature for 2 h, concentrated under reduced pressure and treated with minimal dichloromethane and water. The resulting mixture was eluted on a Celite® extraction tube (ChemElute® diatomaceous earth-based liquid-liquid exchange cartridge) with dichloromethane and concentrated to provide 0.225 g of the title compound.

$^1$H NMR (CDCl$_3$): δ 1.70-1.88 (m, 2H), 2.08-2.26 (m, 2H), 2.33 (s, 3H), 2.77-2.99 (m, 1H), 3.15-3.42 (m, 3H), 3.49-3.68 (m, 1H), 3.93-4.07 (m, 1H), 4.47-4.60 (m, 1H), 5.00 (d, 2H), 5.44-5.58 (m, 1H), 6.33 (s, 1H), 6.73-6.95 (m, 2H), 7.15-7.24 (m, 1H), 7.40 (s, 1H), 7.48-7.54 (m, 1H).

Example 7

Preparation of 1-[4-(4-hydroxyimino)phenylmethyl]-2-thiazolyl]-1-piperidinyl]-2-[5-methyl-3-(trifluoromethyl)-1H-prrazol-1-yl]ethanone Step A: Preparation of 3-bromo-1-phenyl-1,2-propanedione To a solution of 1-phenyl-1,2-propanedione (5 g, 34.0 mmol) in 1,2-dichloroethane (100 mL) bromine (1.71 mL, 5.33 g, 33.3 mmol) was added dropwise. The solution was stirred for 1.5 h at room temperature and concentrated under reduced pressure to give 7.5 g of a mixture of the title compound (25%) and un-reacted 1-phenyl-1,2-propanedione (75%) as a brown liquid. This mixture was of sufficient purity to use in subsequent reactions. $^1$H NMR (CDCl$_3$): δ 4.39 (s, 2H), 7.50 (t, 2H), 7.60-7.75 (m, 1H), 8.08 (d, 2H).

Step B: Preparation of 1-[4-(4-benzoyl-2-thiazolyl)-1-piperidinyl]-2-[5-methyl-3-(trifluoromethyl)-1H-prrazol-1-yl]ethanone A mixture of 3-bromo-1-phenyl-1,2-propanedione (25%) containing 1-phenyl-1,2-propanedione (75%) (i.e. the product of Example 7, Step A) (6.5 g, 7.2 mmol) and 1-[2-[5-methyl-3-(trifluoromethyl)-1H-pyrazol-1-yl]acetyl]-4-piperidinecarbothioamide (2.4 g, 7.2 mmol) in acetone (125 mL) was stirred at rt overnight. The mixture was concentrated under reduced pressure. The resulting solids were filtered, rinsed with diethyl ether and partitioned between ethyl acetate and water. The phases were separated and the lower aqueous phase was extracted with ethyl acetate (3×50 mL). The combined organic phase was washed with brine, dried over magnesium sulfate, filtered and concentrated onto silica gel. Elution with ethyl acetate (100%) and trituration with n-butly chloride and hexanes gave 1-[4-(benzoyl-4,5-dihydro-4-hydroxy-2-thiazolyl)-1-piperidinyl]]-2-[5-methyl-3-(trifluoromethyl)-1H-pyrazol-1-yl]ethanone.

A sample similarly prepared and purified by MPLC provided the following NMR.

$^1$H NMR (CDCl$_3$): δ 1.65-1.83 (m, 2H), 2.05-2.15 (m, 2H), 2.30 (s, 3H), 2.85-2.96 (m, 2H), 3.20-3.30 (m, 1H), 3.43 (d, 1H), 3.90-4.00 (m, 1H), 4.45 (d, 1H), 4.95 (s, 2H), 5.20 (d, 1H), 6.32 (s, 1H), 7.47 (t, 2H), 7.60 (t, 1H), 7.90 (d, 2H).

A solution of this intermediate, trifluoroacetic acid (5 mL) and dichloromethane (10 mL) was stirred at rt for 4 h. The reaction was concentrated under reduced pressure and partitioned between water and ethyl acetate. The lower aqueous phase was extracted with ethyl acetate (2×30 mL) and the combined organic phase, washed with brine, dried over magnesium sulfate, filtered and concentrated under reduced pressure to give 2.5 g of the title compound as an amber solid foam.

$^1$H NMR (CDCl$_3$): δ 1.78-1.90 (m, 2H), 2.28 (br t, 2H), 2.33 (s, 3H), 2.93 (t, 1H), 3.25-3.40 (m, 2H), 4.08 (d, 1H), 4.61 (d, 1H), 4.95-5.05 (m, 2H), 6.38 (s, 1H), 7.50 (t, 2H), 7.62 (t, 1H), 8.13 (s, 1H), 8.18 (d, 2H).

Step C: Preparation of 1-[4-[4-[(hydroxyimino)phenylmethyl]-2-thiazolyl]-1-piperidinyl-2-[5-methyl-3-(trifluoromethyl)-1H-pyrazol-1-yl]ethanone A solution of 1-[4-(4-benzoyl-2-thiazolyl)-1-piperidinyl]-2-[5-methyl-3-(trifluoromethyl)-1H-prrazol-1-yl]ethanone (i.e. the product of Example 7, Step B) (2.42 g, 5.24 mmol), hydroxylamine hydrochloride (0.90 g, 13.10 mmol) and pyridine (12 mL) was heated at 110° C. for 3 h and stirred at rt overnight. The reaction was concentrated under reduced pressure, water was added and the aqueous phase extracted with ethyl acetate (2×10 mL). The combined organic phase was washed with brine, dried over magnesium sulfate, filtered and concentrated under reduced pressure to give 2.34 g of the title compound as a mixture of syn and anti isomers which slowly solidified on standing.

$^1$H NMR (CDCl$_3$): δ 1.70-1.82 (m, 2H), 2.18-2.30 (m, 2H), 2.30 and 2.33 (two s, 3H), 2.80-2.93 (m, 1H), 3.20-3.40 (m, 2H), 4.00-4.06 (m, 1H), 4.53-5-65 (m, 1H), 4.98-5.10 (m, 2H), 6.33 (s, 1H), 7.00-7.63 (m, 6H), 8.22 and 12.40 (two s, 1H).

The syn and anti isomers were separated by MPLC.

$^1$H NMR (CDCl$_3$): δ 1.74-1.86 (m, 2H), 2.21 (br t, 2H), 2.33 (s, 3H), 2.89 (t, 1H), 3.27-3.40 (m, 2H), 4.08 (br d, 1H), 4.62 (br d, 1H), 4.93-5.07 (m, 2H), 6.34 (s, 1H), 7.38-7.59 (m, 6H), 12.48 (br s, 1H) for Isomer A.

$^1$H NMR (CDCl$_3$): δ 1.70-1.89 (m, 2H), 2.20 (br t, 2H), 2.30 (s, 3H), 2.87 (t, 1H), 3.19-3.39 (m, 2H), 4.00 (br d, 1H), 4.55 (br d, 1H), 4.96 (s, 2H), 6.33 (s, 1H), 7.00 (s, 1H), 7.42-7.50 (m, 5H), 8.83 (br s, 1H) for Isomer B.

Example 8

Preparation of of 4-[4-[(hydroxyimino)methyl]-2-thiazolyl]-1-[[5-methyl-3-(trifluoromethyl)-1H-pyrazol-1-yl]acetyl]piperidine Step A: Preparation of 2-(4-piperidinyl)-4-thiazole-carboxaldehydemono-hydrochloride To a solution of 1,1-dimethylethyl 4-(4-formyl-2-thiazolyl)-1-piperidinecarboxylate (1.0 g, 3.4 mmol) in dichloromethane (20 mL) was added a solution of hydrogen chloride in diethyl ether (2.0 mL, 15 ml, 30 mmol). The reaction mixture was stirred under nitrogen at room temperature for 2 h and then evaporated under reduced pressure to give 1.2 g of the title compound as a white solid.

$^1$H NMR (CDCl$_3$) δ 2.31-2.38 (m, 2H), 2.44-2.50 (m, 2H), 3.11-3.20 (m, 2H), 3.36-3.44 (m, 1H), 3.57-3.65 (m, 2H), 8.14 (s, 1H), 10.01 (s, 1H).

Step B: Preparation of 4-(4-formyl-2-thiazolyl)-1-[[5-methyl-3-(trifluoromethyl)-1H-pyrazol-1-yl]acetyl]piperidine To a solution of 5-methyl-3-(trifluoromethyl)-1H-pyrazole-1-acetic acid (0.8 g, 3.8 mmol) in dichloromethane (10 mL) was added oxalyl chloride (2.4 g, 19.2 mmol) and two drops of N,N-dimethylformamide, resulting in slight exotherm. The reaction mixture was then heated at reflux for 15 minutes. The reaction mixture was concentrated in vacuo, the residue was suspended in tetrahydrofuran (10 mL) and treated with a solution of 2-(4-piperidinyl)-4-thiazolecarboxaldehyde monohydrochloride (i.e. the product of Example 8, Step A) (1.1 g, 5.1 mmol) in tetrahydrofuran (10 mL), followed by dropwise addition of triethylamine (1.2 g, 11.9 mmol). The reaction mixture was stirred overnight at room temperature and then partitioned between 1 N aqueous hydrochloric acid and ethyl acetate. The organic layer was separated, and the aqueous layer was extracted with additional ethyl acetate (2×30 mL). The combined organic layers were washed with 1 N aqueous hydrochloric acid, saturated aqueous sodium bicarbonate solution, and brine. The organic layer was dried (MgSO$_4$) and evaporated under reduced pressure to give 0.8 g of the title compound as a yellow oil.

$^1$H NMR (CDCl$_3$): δ 1.79-1.90 (m, 2H), 2.18-2.29 (m, 2H), 2.33 (s, 3H), 2.87-2.94 (m, 1H), 3.28-3.40 (m, 2H), 4.05-4.15 (m, 1H), 4.56-4.64 (m, 1H), 4.99-5.02 (m, 2H), 6.35 (s, 1H), 8.12 (s, 1H), 10.01 (s, 1H).

Step B1: Alternative Preparation of 4-(4-formyl-2-thiazolyl)-1-[[5-methyl-3-(trifluoromethyl)-1H-pyrazol-1-yl]acetyl]piperidine To a mixture of 1-[2-[5-methyl-3-(trifluoromethyl)-1H-pyrazol-1-yl]acetyl]-4-piperidinecarbothioamide (i.e. the product of Example 1, Step C) (20 g, 59.9 mmol) in isopropyl alcohol (90 mL) was added 1,3-dichloroacetone (8.99 g, 71.3 mmol) and the reaction mixture heated at 65 for 1.5 h. After cooling, a solution of sodium carbonate (7.39 g, 70.0 mmol) in water (92 mL) was added dropwise. After 2 h additional water (31 mL) was added and the resulting precipitate rinsed with water (62 mL). Drying overnight under reduced pressure at 45° C. provided 18.24 g of the title compound as a light gray solid.

$^1$H NMR (CDCl$_3$): δ 1.70-1/85 (m, 2H), 2.20 (t, 2H), 2.32 (s, 3H), 2.88 (t, 1H), 3.20-3.38 (m, 2H), 4.03 (d, 1H), 4.55 (d, 1H), 4.95-5.05 (m, 2H), 4.67 (s, 2H), 6.34 (s, 1H), 7.22 (s, 1H).

To a mixture of 1-[4-[4-(chloromethyl)-2-thiazolyl]-1-piperidinyl]-2-[5-methyl-3-(trifluoromethyl)-1H-pyraol-1-yl]ethanone (18.24 g, 44.9 mmol), sodium bromide (1 g, 9.7 mmol), carbon tetrachloride (60 mL) and dimethylsulfoxide (50 mL) was added 4-methylmorpholine 4-oxide (13.69 g, 116.6 mmol). The mixture was stirred at room temperature for 2 days then pardoned between water and dichloromethane. The organic layer was separated and the aqueous layer was extracted with additional dichloromethane (2×100 mL). The combined organic layers were dried (MgSO$_4$) and evaporated under reduced pressure and purified by MPLC to 8.43 g of the title compound as a white solid.

Step C: Preparation of 4-[4-[(hydroxyimino)methyl]-2-thiazolyl]-1-[[5-methyl-3-(trifluoromethyl)-1H-pyrazol-1-yl]acetyl]piperidine To a solution of 4-(4-formyl-2-thiazolyl)-1-[[5-methyl-3-(trifluoromethyl)-1H-pyrazol-1-yl]acetyl]piperidine (i.e. the product of Example 8, Step B) (0.8 g, 2.07 mmol) in ethyl alcohol (15 mL) was added hydroxylamine (50% aqueous solution, 0.136 g, 4.1 mmol) and the reaction mixture was stirred at room temperature for 10 minutes. The reaction mixture was concentrated under reduced pressure to give a yellow oil, which was purified by flash column chromatography on silica gel using 50% ethyl acetate in hexanes as eluant to give 0.7 g of the title compound as a white solid. This compound can be used as an intermediate to make compounds of the invention (via alkylation of the hydroxyimino group).

$^1$H NMR (CDCl$_3$): δ 1.72-1.85 (m, 2H), 2.17-2.27 (m, 2H), 2.32 (s, 3H), 2.82-2.91 (m, 1H), 3.25-3.37 (m, 2H), 4.02-4.09 (m, 1H), 4.58-4.63 (m, 1H), 4.95-5.03 (m, 2H), 6.35 (s, 1H), 7.43 (s, 1H), 7.71 (s, 1H), 8.19 (s, 1H).

By the procedures described herein together with methods known in the art, the following compounds of Tables 1a to 8v can be prepared. The following abbreviations are used in the Tables which follow: Me means methyl, Et means ethyl, Ph means phenyl, n means normal, i means iso, OMe means methoxy, SMe means methylthio, —CN means cyano, Ph means phenyl and —NO$_2$ means nitro.

Fragments E-1a through E-3d shown below are referred to in the Tables.

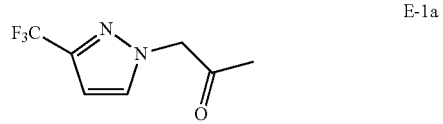

E-1a

-continued

| | |
|---|---|
| E-1b | |
| E-1c | |
| E-1d | |
| E-1e | |
| E-1f | |
| E-1g | |
| E-1h | |
| E-1i | |
| E-1j | |
| E-1k | |

-continued

| | |
|---|---|
| E-1l | |
| E-1m | |
| E-1n | |
| E-2a | |
| E-2b | |
| E-2c | |
| E-2d | |
| E-3a | |
| E-3b | |
| E-3c | |
| E-3d | |

The invention includes but is not limited to the following exemplary species.

TABLE 1a

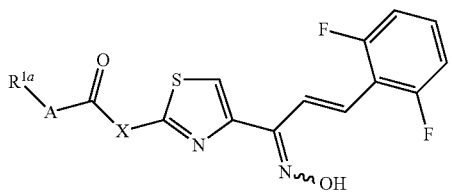

| $R^{1a}$ | $R^{1a}$ |
|---|---|
| Ph | 3-ethylphenyl |
| 2-methylphenyl | 3-(CF$_3$)phenyl |
| 2-methoxyphenyl | 3-cyanophenyl |
| 2-chlorophenyl | 3-nitrophenyl |
| 2-bromophenyl | 2,5-dichlorophenyl |
| 2-ethoxyphenyl | 5-bromo-2-chlorophenyl |
| 2-(methylthio)phenyl | 2-chloro-5-methylphenyl |
| 3-chlorophenyl | 2-methoxy-5-(CF$_3$)phenyl |
| 3-bromophenyl | 2,5-diethylphenyl |
| 3-iodophenyl | 3-methylpyrazol-1-yl |
| 3-methylphenyl | 3-chloropyrazol-1-yl |
| 2-chloro-5-(CF$_3$)phenyl | 3-bromopyrazol-1-yl |
| 2,5-dibromophenyl | 3-(CF$_3$)pyrazol-1-yl |
| 2-bromo-5-methylphenyl | 3,5-dimethylpyrazol-1-yl |
| 2-bromo-5-(CF$_3$)phenyl | 3-chloro-5-methylpyrazol-1-yl |
| 5-chloro-2-methylphenyl | 3-bromo-5-methylpyrazol-1-yl |
| 5-bromo-2-methylphenyl | 5-methoxy-3-methylpyrazol-1-yl |
| 2,5-dimethylphenyl | 3,5-diethylpyrazol-1-yl |
| 2-methyl-5-(CF$_3$)phenyl | 5-ethyl-3-(CF$_3$)pyrazol-1-yl |
| 5-cyano-2-methylphenyl | 2,5-dimethyl-3-furyl |
| 2-methyl-5-nitrophenyl | 2,5-dimethyl-3-thienyl |
| 5-chloro-2-methoxyphenyl | 2,5-dichloro-3-thienyl |
| 5-bromo-2-methoxyphenyl | 1,4-dimethyl-3-pyrrolyl |
| 2-methoxy-5-methylphenyl | 1,4-dimethyl-3-pyrazolyl |
| 3-ethyl-5-methylpyrazol-1-yl | 1,3-dimethyl-4-pyrazolyl |
| 5-methyl-3-(CF$_3$)pyrazol-1-yl | 2,5-dimethyl-4-oxazolyl |
| 5-methyl-3-(C$_2$F$_5$)pyrazol-1-yl | 2,5-dimethyl-4-thiazolyl |
| 5-chloro-3-methylpyrazol-1-yl | 3,6-dimethyl-2-pyridyl |
| 3,5-dichloropyrazol-1-yl | 2,5-dimethyl-3-pyridyl |
| 5-chloro-3-(CF$_3$)pyrazol-1-yl | 2,5-dimethyl-4-pyridyl |
| 5-bromo-3-methylpyrazol-1-yl | 3,6-dichloro-2-pyridyl |
| 3,5-dibromopyrazol-1-yl | 2,5-dichloro-3-pyridyl |
| 5-bromo-3-(CF$_3$)pyrazol-1-yl | 2,5-dichloro-4-pyridyl |
| 3,5-dimethyl-2-thienyl | 4-bromo-3-pyridazinyl |
| 3,5-dichloro-2-thienyl | 4-(CF$_3$)-2-pyrimidinyl |
| 3,5-dimethyl-2-furyl | 3,6-dimethyl-2-pyrazinyl |
| 4-methyl-2-(CF$_3$)-5-thiazolyl | 2,5-dimethyl-4-pyrimidinyl |
| 4-methyl-2-(CF$_3$)-5-oxazolyl | 4-methoxy-5-pyrimidinyl |
| 1-methyl-4-(CF$_3$)-2-imidazolyl | 3,6-dimethyl-4-pyridazinyl |
| 2,4-dimethyl-1-pyrrolyl | 1-methyl-4-(CF$_3$)imidazol-2-yl |
| 1-methyl-3-(CF$_3$)pyrazol-5-yl | 3,5-bis-(CF$_3$)pyrazol-1-yl |
| 3-bromo-5-(CF$_3$)pyrazol-1-yl | 3-chloro-5-(CF$_3$)-pyrazol-1-yl |
| 3-methyl-5-(CF$_3$)-pyrazol-1-yl | 3,5-bis-(difluoromethoxy)pyrazol-1-yl |
| 3-methoxy-5-(CF$_3$)-pyrazol-1-yl | 3,5-dimethoxypyrazol-1-yl |
| 3,5-dibromopyrazol-1-yl | 5-ethoxy-3-methylpyrazol-1-yl |
| 5-methoxy-3-methylpyrazol-1-yl | 5-ethoxy-3-(CF$_3$)pyrazol-1-yl |
| 5-methoxy-3-(CF$_3$)pyrazol-1-yl | 3,5-dibromotriazol-1-yl |
| 3,5-dichlorotriazol-1-yl | 3-chloro-5-methyltriazol-1-yl |
| 3-methyl-5-chlorotriazol-1-yl | 3-bromo-5-methyltriazol-1-yl |
| 3-methyl-5-bomotriazol-1-yl | 3-(CF$_3$)-5-chlorotriazol-1-yl |
| 3-chloro-5-(CF$_3$)triazol-1-yl | 3-(CF$_3$)-5-bromotriazol-1-yl |
| 3-bromo-5-(CF$_3$)triazol-1-yl | 3,5-bis(CF$_3$)triazol-1-yl |
| n-butyl | Trifluoromethoxyethyl |
| i-amyl | 2-methoxyethoxy |
| 3-methyl-2-buten-1-yl | 3,3,3-trifluoropropoxy |
| propargyl | 2,2,2-trifluoroethylcarbonyloxy |
| 4,4,4-trifluorobutan-1-yl | allyloxy |
| 3,3-dichloro-2-propen-1-yl | propylthio |
| 2-(CF$_3$)cyclopropyl-1-yl | 3,3,3-trifluoropropylthio |
| i-butoxy | 3,3,3-trifluoropropylamino |
| 2,2,2-trifluoroethoxymethyl | |

A is CHR$^{15}$, R$^{15}$ is H, X is X-1 and n is 0.

The present disclosure also includes Table 1b through 1d, each of which is constructed the same as Table 1a above except that the table heading in Table 1a (i.e. "A is CHR$^{15}$, R$^{15}$ is H, X is X-1 and n is 0" is replaced with the respective table headings shown below. For example, in Table 1b the table heading is "A is CHR$^{15}$, R$^{15}$ is H, X is X-2 and n is 0" and R$^{1a}$ is as defined in Table 1a above. Thus, the first entry in Table 1b specifically discloses a compound of Formula 1 wherein A is CHR$^{15}$, R$^{15}$ is H, X is X-2, n is 0 and R$^{1a}$ is phenyl.

| | Table Headings | | | |
|---|---|---|---|---|
| Table | A is | X is | n | R$^{6b}$ is |
| 1b | CHR$^{15}$, R$^{15}$ is H | X-2 | 0 | — |
| 1c | CHR$^{15}$, R$^{15}$ is H | X-4 | 0 | — |
| 1d | CHR$^{15}$, R$^{15}$ is H | X-5 | 0 | H |

TABLE 2

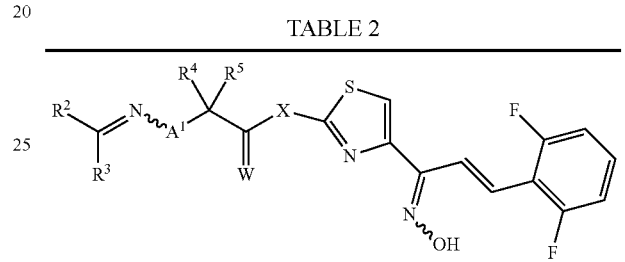

| $R^2$ | $R^3$ | $R^4$ | $R^5$ | $A^1$ |
|---|---|---|---|---|
| CH$_3$ | CH$_3$ | H | H | O |
| CH$_3$ | CH$_3$ | H | H | S |
| CH$_3$ | CH$_3$ | H | H | NH |
| CH$_3$ | CH$_3$ | H | H | N(Me) |
| CH$_3$ | CH$_3$ | H | H | CH$_2$ |
| CH$_3$ | CH$_3$ | H | H | OCH$_2$ |
| CH$_3$ | CH$_3$ | H | H | SCH$_2$ |
| CH$_3$ | CH$_3$ | H | H | NHCH$_2$ |
| CH$_3$ | CH$_3$ | H | H | —N(Me)CH$_2$— |
| CH$_3$ | CH$_3$ | CH$_3$ | H | O |
| CH$_3$ | CH$_3$ | CH$_3$ | CH$_3$ | O |
| CH$_3$ | CH$_3$ | H | H | O |
| CF$_3$ | H | H | H | O |
| CF$_3$ | H | H | H | S |
| CF$_3$ | H | H | H | NH |
| CF$_3$ | H | H | H | N(Me) |
| CF$_3$ | H | H | H | CH$_2$ |
| CF$_3$ | H | H | H | OCH$_2$ |
| CF$_3$ | H | H | H | SCH$_2$ |
| CF$_3$ | H | H | H | NHCH$_2$ |
| CF$_3$ | H | H | H | —N(Me)CH$_2$— |
| CF$_3$ | CH$_3$ | H | H | O |
| CF$_3$ | CH$_3$ | H | H | S |
| CF$_3$ | CH$_3$ | H | H | NH |
| CF$_3$ | CH$_3$ | H | H | N(Me) |
| CF$_3$ | CH$_3$ | H | H | CH$_2$ |
| CF$_3$ | CH$_3$ | H | H | OCH$_2$ |
| CF$_3$ | CH$_3$ | H | H | SCH$_2$ |
| CF$_3$ | CH$_3$ | H | H | NHCH$_2$ |
| CF$_3$ | CH$_3$ | H | H | —N(Me)CH$_2$— |
| CF$_3$ | H | Me | H | O |
| CF$_3$ | CH$_3$ | H | Me | O |
| CF$_3$CH$_2$ | H | H | H | O |
| CF$_3$CH$_2$ | CH$_3$ | H | H | O |
| Et | H | H | H | O |
| Et | CH$_3$ | H | H | O |
| CH$_3$ | H | H | H | O |

X is X-1, W is O and n is 0.

TABLE 3

[Structure: thiazole compound with R^1b-N=C(W^1)-X- linked to thiazole with (2,6-difluorophenyl)-CH=CH-C(=NOH)- substituent]

| R^1b | W^1 | R^1b | W^1 |
|---|---|---|---|
| 2-methylphenyl | OMe | 2-methoxy-5-methylphenyl | NHOH |
| 2-methoxyphenyl | SMe | 2-methoxy-5-(CF_3)-phenyl | NHOMe |
| 2-chlorophenyl | NH_2 | 2,5-diethylphenyl | NHNH_2 |
| 2-bromophenyl | NHOH | 3,5-dimethylpyrazol-1-yl | OMe |
| 2-ethylphenyl | NHOMe | 3,5-dichloropyrazol-1-yl | SMe |
| 2-ethoxyphenyl | NHNH_2 | 3,5-dibromopyrazol-1-yl | NH_2 |
| 2-(methylthio)-phenyl | OMe | 3,5-bis-(CF_3)-pyrazol-1-yl | NHOH |
| 2-(trifluoromethoxy)-phenyl | SMe | 5-methyl-3-(CF_3)-pyrazol-1-yl | NHOMe |
| 3-chlorophenyl | NH_2 | 3,5-dimethyl-1,2,4-triazol-1-yl | NHNH_2 |
| 3-bromophenyl | NHOH | 3,5-dichloro-1,2,4-triazol-1-yl | OMe |
| 3-methylphenyl | NHOMe | 3,5-dibromo-1,2,4-triazol-1-yl | SMe |
| 2,5-dimethylphenyl | NHNH_2 | n-butyl | NH_2 |
| 2,5-dichlorophenyl | OMe | i-amyl | NHOH |
| 2-chloro-5-(CF_3)-phenyl | SMe | 3-methyl-2-buten-1-yl | NHOMe |
| 2,5-dibromophenyl | NH_2 | Propargyl | NHNH_2 |
| 2-bromo-5-(CF_3)-phenyl | NHOH | 4,4,4-trifluorobutan-1-yl | OMe |
| 5-chloro-2-methylphenyl | NHOMe | 3,3-dichloro-2-propen-1-yl | SMe |
| 5-bromo-2-methylphenyl | NHNH_2 | 2-CF_3cyclopropyl-1-yl | NH_2 |
| 2-methyl-5-(CF_3)-phenyl | OMe | i-butoxy | NHOH |
| 5-chloro-2-methoxyphenyl | SMe | Trifluoromethoxyethyl | NHOMe |
| 5-bromo-2-methoxyphenyl | NH_2 | 3,3,3-trifluoropropoxy | NHNH_2 |

X is X-1 and n is 0.

TABLE 4

[Structure: 5-methyl-3-(CF_3)-pyrazole-CH_2-C(=O)-piperidine-G-C(=NOH)-CH=CH-(2,6-difluorophenyl)]

| G | R^29a | R^30a | G | R^29a | R^30a |
|---|---|---|---|---|---|
| G-1 | H | — | G-26 | H | — |
| G-2 | H | — | G-27 | H | — |
| G-3 | H | 1-Me | G-28 | H | — |
| G-4 | H | — | G-29 | H | — |
| G-5 | H | — | G-30 | H | — |
| G-6 | H | 1-Me | G-30 | 5-Me | — |
| G-7 | — | — | G-30 | 5-Cl | — |
| G-8 | — | — | G-30 | 5-Br | — |
| G-9 | — | 1-Me | G-30 | 5-CN | — |
| G-9 | — | H | G-30 | 5-CF_3 | — |
| G-10 | H | — | G-31 | H | — |
| G-11 | H | — | G-32 | H | — |
| G-12 | H | 1-Me | G-33 | H | — |
| G-13 | H | H | G-34 | H | — |
| G-14 | H | — | G-35 | H | — |
| G-14 | 5-Me | — | G-36 | H | — |
| G-15 | H | — | G-37 | H | — |
| G-15 | 5-Me | — | G-38 | H | — |
| G-16 | H | 1-Et | G-39 | H | 1-Me |
| G-17 | H | — | G-40 | H | — |
| G-18 | H | — | G-41 | H | — |
| G-19 | — | H | G-42 | H | 1-Me |
| G-20 | — | — | G-43 | H | 1-Me |
| G-21 | — | — | G-44 | H | — |
| G-22 | H | 1-Me | G-45 | H | — |
| G-23 | H | — | G-46 | — | — |

TABLE 4-continued

[Same structure as Table 4]

| G | R^29a | R^30a | G | R^29a | R^30a |
|---|---|---|---|---|---|
| G-24 | H | — | G-47 | — | — |
| G-25 | H | — | G-48 | — | 1-Me |

In Table 4 the individual G structures are from Exhibit 3 (e.g., G-1 through G-48) where the bond projecting to the left is connected to X of Formula 1 and the bond projecting to the right is bonded to the carbon of C(=W^2)Z. For instance, the first compound listed in Table 4 is a compound of Formula 1 wherein E is E-1a, X is X-1, n is 0, G is G-1, R^29a is H and there is no R^30a substituent. When there is more than one R^29a group in a G structure then all the R^29a groups are as indicated in the table. For instance the fourth compound listed in Table 4 has a thienyl structure (G-4) with both R^29a groups equal to hydrogen.

TABLE 5

[Structure: 5-methyl-3-(CF_3)-pyrazole-CH_2-C(=O)-piperidine-thiazole-C(=NOH)-CH=CH-Q]

| Q | (R^9a)_p | R^9b | Q | (R^9a)_p | R^9b |
|---|---|---|---|---|---|
| Q-1 | H | — | Q-52 | H | — |
| Q-2 | H | — | Q-53 | H | — |
| Q-3 | H | 1-CH_3 | Q-54 | H | — |
| Q-4 | 2-Me | — | Q-55 | H | — |
| Q-5 | 5-(2-F-phenyl) | — | Q-56 | H | — |
| Q-6 | 5-Ph | — | Q-57 | H | — |
| Q-7 | 2-Ph | — | Q-58 | H | — |
| Q-8 | H | — | Q-59 | H | — |
| Q-9 | H | — | Q-60 | H | — |
| Q-10 | H | 1-CH_3 | Q-61 | H | — |
| Q-11 | H | 1-CH_3 | Q-62 | — | — |
| Q-12 | H | 1-CH_3 | Q-63 | H | — |
| Q-13 | H | 4-CH_3 | Q-63 | 3-Cl | — |
| Q-14 | H | 1-CH_3 | Q-63 | 4-CN | — |
| Q-15 | 5-(2-Cl-phenyl) | — | Q-63 | 4-Ph | — |
| Q-16 | Ph | — | Q-63 | 4-CF3 | — |
| Q-17 | Ph | — | Q-63 | 3-CH3 | — |
| Q-18 | H | — | Q-63 | 4-F | — |
| Q-19 | H | — | Q-64 | H | — |
| Q-20 | H | — | Q-65 | H | — |
| Q-21 | H | 1-CH_3 | Q-66 | H | — |
| Q-22 | H | 1-CH_3 | Q-67 | H | — |
| Q-23 | H | 1-CH_3 | Q-68 | H | — |
| Q-24 | 2-Ph | — | Q-69 | H | — |
| Q-25 | 2-Ph | — | Q-70 | H | — |
| Q-26 | H | — | Q-70 | 4-Cl | — |
| Q-27 | H | — | Q-70 | 4-CH_3 | — |
| Q-28 | H | 1-CH_2CH_3 | Q-70 | 4-OCH_3 | — |
| Q-29 | Ph | — | Q-70 | 5-F | — |
| Q-30 | H | — | Q-70 | 5-Cl | — |
| Q-31 | 5-Ph | 1-CH_3 | Q-70 | 6-CH_3 | — |
| Q-32 | 3-CH_3 | — | Q-70 | 6-F | — |
| Q-33 | 4-CH_3 | — | Q-70 | 6-Br | — |
| Q-34 | H | — | Q-70 | 6-CN | — |
| Q-35 | 4-Ph | — | Q-71 | H | — |
| Q-36 | H | — | Q-71 | 5-Cl | — |
| Q-37 | H | — | Q-72 | H | H |
| Q-38 | H | — | Q-72 | — | 1-CH_3 |
| Q-39 | H | — | Q-72 | — | 1-CO_2CH_3 |
| Q-40 | H | — | Q-72 | — | 1-OCH_3 |
| Q-41 | H | — | Q-72 | — | 1-C(=O)CH_3 |
| Q-42 | H | — | Q-73 | — | — |
| Q-43 | H | — | Q-74 | H | — |
| Q-44 | H | — | Q-75 | H | 3-CH_3 |
| Q-45 | 2-F | — | Q-76 | H | — |
| Q-45 | 2-OCF_3 | — | Q-77 | H | — |
| Q-45 | 2-cyclopropyl | — | Q-78 | H | 3-CH_3 |

TABLE 5-continued

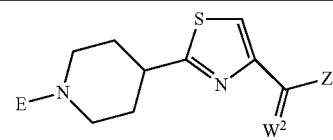

| Q | $(R^{9a})_p$ | $R^{9b}$ | Q | $(R^{9a})_p$ | $R^{9b}$ |
|---|---|---|---|---|---|
| Q-45 | 2-CF$_3$ | — | Q-79 | H | 1-CH$_3$ |
| Q-45 | 2-Ph | — | Q-80 | H | — |
| Q-45 | 2-CN | — | Q-81 | H | — |
| Q-45 | 2,6-di-Cl | — | Q-82 | H | — |
| Q-45 | 2-Cl-6-F | — | Q-83 | H | — |
| Q-45 | 2,6-di-CH$_3$ | — | Q-84 | H | — |
| Q-45 | 2-F-6-CH$_3$ | — | Q-85 | 5,5-di-CH$_3$ | — |
| Q-45 | 2-CH$_3$-6-OCH$_3$ | — | Q-86 | H | 1-CH$_3$ |
| Q-45 | 3-CF$_3$ | — | Q-86 | 5,5-di-CH$_3$ | 1-CH$_3$ |
| Q-45 | 2,4,6-tri-F | — | Q-87 | H | — |
| Q-45 | 2,4,6-tri-CH$_3$ | — | Q-88 | H | 1-CH$_3$ |
| Q-45 | 2,6-di-F-4-OCH$_3$ | — | Q-89 | H | — |
| Q-45 | 3-(1H-1,2,4-triazol-1-yl) | — | Q-90 | H | — |
| Q-45 | 2-(2-pyridinyl) | — | Q-91 | H | — |
| Q-45 | 2-piperidinyl | — | Q-92 | H | 1-CH$_3$ |
| Q-46 | H | — | Q-93 | H | — |
| Q-47 | H | — | Q-94 | H | — |
| Q-48 | 2-F | — | Q-95 | H | 1-CH$_3$ |
| Q-48 | 2,6-di-CH$_3$ | — | Q-96 | H | — |
| Q-48 | 2-CH$_3$-6-OCH$_3$ | — | Q-97 | H | — |
| Q-48 | 2-CF$_3$ | — | Q-98 | H | — |
| Q-48 | 2-Ph | — | Q-99 | H | — |
| Q-48 | 2-CN | — | Q-100 | H | — |
| Q-49 | H | — | Q-101 | H | — |
| Q-50 | H | — | Q-102 | 5,5-di-CH$_3$ | 1-CH$_3$ |
| Q-51 | H | — | Q-103 | 2,6-di-F | — |

In Table 5 the individual Q structures are from Exhibit 4 (e.g., Q-1 through Q-103). For instance, the first compound listed in Table 5 is a compound of Formula 1 wherein E is E-1a, X is X-1, n is 0, G is G-1, $R^{29a}$ is H, Z is alkenyl substituted by Q, Q is Q-1, $(R^{9a})_p$ is H and there is no $R^{9b}$ substituent.

TABLE 7a

| L | $(R^{9a})_p$ | L | $(R^{9a})_p$ | L | $(R^{9a})_p$ |
|---|---|---|---|---|---|
| L-1 | — | L-38 | 2,6-di-Cl | L-61 | H |
| L-2 | — | L-38 | 2,6-di-F | L-62 | — |
| L-3 | — | L-39 | 2-F | L-63 | — |
| L-4 | — | L-39 | 2-Cl | L-64 | — |
| L-5 | — | L-39 | 2-CN | L-65 | — |
| L-6 | — | L-39 | 2-CF3 | L-66 | — |
| L-7 | — | L-39 | 2,6-di-Cl | L-67 | — |
| L-8 | — | L-39 | 2,6-di-F | L-68 | — |
| L-9 | — | L-40 | 2-Cl | L-69 | — |
| L-10 | 2,6-di-F | L-41 | 2-F | L-70 | — |
| L-11 | 2,6-di-Cl | L-42 | 2-CF$_3$ | L-71 | 2-Me |
| L-12 | 2-Cl | L-43 | H | L-72 | H |
| L-13 | 2-F | L-43 | 5-Cl | L-73 | H |
| L-14 | 2,6-di-F | L-44 | H | L-74 | H |
| L-15 | 3-Cl | L-45 | 2-F | L-75 | H |
| L-16 | 4-F | L-45 | 2-Cl | L-76 | 2-Me |
| L-17 | 2-Cl | L-45 | 2-CN | L-77 | 2-F |
| L-18 | 4-Cl | L-45 | 2-CF3 | L-78 | 2-Cl |
| L-19 | 4-F | L-45 | 2,6-di-Cl | L-79 | 2-Me |
| L-20 | 2,6-di-F-4-OMe | L-45 | 2,6-di-F | L-80 | 2,6-di-F |
| L-21 | 2-F | L-46 | 2-F | L-81 | 2,6-di-Me |
| L-22 | 2,6-di-Me | L-46 | 2-Cl | L-82 | 2-F |
| L-23 | 2,4,6-tri-F | L-46 | 2-CN | L-83 | 2,6-di-Cl |
| L-24 | 3-(1H-1,2,4-triazol-1-yl) | L-46 | 2-CF3 | L-84 | 2,6-di-F |
| L-25 | 2-CN | L-46 | 2,6-di-Cl | L-85 | H |
| L-26 | 2-CF$_3$ | L-46 | 2,6-di-F | L-86 | 2-Me |
| L-27 | 2,6-di-Cl | L-47 | 2,6-di-F | L-87 | H |
| L-28 | 2,6-di-Me | L-48 | 2,6-di-Cl | L-88 | 2,6-di-F |
| L-29 | H | L-49 | 2-Cl | L-89 | H |
| L-30 | 2-CF$_3$ | L-50 | 2-F | L-90 | — |

TABLE 6

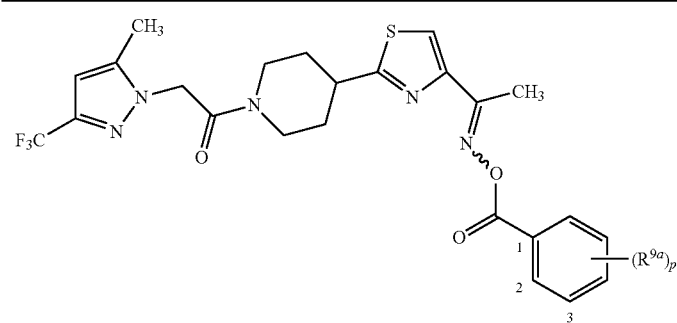

| $(R^{9a})_p$ | $(R^{9a})_p$ | $(R^{9a})_p$ |
|---|---|---|
| 2-CN | 2-CF$_3$ | 2-CO2CH$_2$CH$_3$ |
| 2-NO$_2$ | 2-CH=CHCl | 3-OC(=O)CH$_3$ |
| 2-F-6-CH$_3$ | 2-C≡CCl | 2-C(=O)N(CH$_3$)$_2$ |
| 2,6-di-CH$_3$ | 3-OCH$_3$ | 2-phenyl |
| 2,6-di-Cl | 2-OCF$_3$ | 2-(2,6-di-F-phenyl) |
| 3-Et | 3-SCH$_3$ | 2-(naphthalen-1-yl) |
| 3-CH=CH$_2$ | 2-S(=O)CH$_3$ | 3-(1H-1,2,4-triazol-1-yl) |
| 2-C≡CH | 3-SO$_2$CH$_3$ | 2-(pyridin-3-yl) |
| 2-cyclopropyl | 2-N(CH$_3$)$_2$ | 2-cyclohexyl |
| 2-CH$_2$-cyclohexyl | 2-CH$_2$OCH$_3$ | 2-(4-morpholinyl) |
| 2-[1,1'-bicyclopropyl]-2-yl | 2-C(=O)CH$_3$ | |

TABLE 7a-continued

[Structure: piperidine-thiazole with E-N, and C(=W²)Z group]

| L | $(R^{9a})_p$ | L | $(R^{9a})_p$ | L | $(R^{9a})_p$ |
|---|---|---|---|---|---|
| L-31 | 2,6-di-Cl | L-51 | 2,6-di-F | L-91 | — |
| L-32 | 2-Cl | L-52 | H | L-92 | 2-Me |
| L-33 | 2,6-di-F | L-53 | H | L-93 | 2-F |
| L-34 | H | L-53 | 5-Cl | L-94 | 2,6-di-F |
| L-35 | H | L-54 | — | L-95 | 2,6-di-Cl |
| L-36 | H | L-55 | — | L-96 | — |
| L-37 | H | L-56 | 2-Me | L-97 | — |
| L-38 | 2-F | L-57 | 2-Cl | L-98 | — |
| L-38 | 2-Cl | L-58 | 2,6-di-Cl | L-99 | 2-F |
| L-38 | 2-CN | L-59 | 2,6-di-F | L-100 | 2,6-di-F |
| L-38 | 2-CF3 | L-60 | H | | |

In Table 7a wherein C(=W²)Z is L, the individual L structures are from Exhibit 7 (e.g., L-1 through L-100) where the bond projecting to the left is connected to G of Formula 1. For instance, the first compound listed in Table 7a is a compound of Formula 1 wherein C(=W²)Z is L and L is L-1 (e.g. W² is NOR¹², R¹² is H and Z is H) and there is no $(R^{9a})_p$ substituent.
E is E-1a.

The present disclosure also includes Table 7b through 7v, each of which is constructed the same as Table 7a above except that the Table Heading in Table 7a (i.e. "E is E-1a") is replaced with the respective table headings shown below. For example, in Table 7b the table heading is "E is E-1b". L and $(R^{9a})_p$ are as defined in Table 7a above. Thus, the first entry in Table 7b specifically discloses a compound of Formula 1 wherein L is L-1 and there is no value for the $(R^{9a})_p$ substituent.

| Table | Table Heading |
|---|---|
| 7b | E is E-1b |
| 7c | E is E-1c |
| 7d | E is E-1d |
| 7e | E is E-1e |
| 7f | E is E-1f |
| 7g | E is E-1g |
| 7h | E is E-1h |
| 7i | E is E-1i |
| 7j | E is E-1j |
| 7k | E is E-1k |
| 7l | E is E-1l |
| 7m | E is E-1m |
| 7n | E is E-1n |
| 7o | E is E-2a |
| 7p | E is E-2b |
| 7q | E is E-2c |
| 7r | E is E-2d |
| 7s | E is E-3a |
| 7t | E is E-3b |
| 7u | E is E-3c |
| 7v | E is E-3d |

TABLE 8a

[Structure: E-X-thiazole with C(=W²)Z group]

| L | $(R^{9a})_p$ | X | n | $R^{6b}$ |
|---|---|---|---|---|
| L-1 | — | X-2 | 0 | — |
| L-2 | — | X-4 | 0 | — |

TABLE 8a-continued

[Structure: E-X-thiazole with C(=W²)Z group]

| L | $(R^{9a})_p$ | X | n | $R^{6b}$ |
|---|---|---|---|---|
| L-3 | — | X-4 | 0 | — |
| L-4 | — | X-2 | 0 | — |
| L-20 | 2-F | X-2 | 0 | — |
| L-22 | 2-Cl | X-4 | 0 | — |
| L-23 | 2,6-di-F | X-2 | 0 | — |
| L-23 | 2,6-di-F | X-3 | 0 | — |
| L-23 | 2,6-di-F | X-4 | 0 | — |
| L-23 | 2,6-di-F | X-5 | 0 | H |
| L-23 | 2,6-di-F | X-5 | 0 | CH₃ |
| L-24 | 2,6-di-F | X-2 | 0 | — |
| L-25 | 2,6-di-F | X-2 | 0 | — |
| L-26 | 2,6-di-F | X-2 | 0 | — |
| L-39 | 2,6-di-F | X-2 | 0 | — |
| L-43 | H | X-2 | 0 | — |
| L-46 | 2,6-di-F | X-2 | 0 | — |

In Table 8a wherein C(=W²)Z is L, the individual L structures are from Exhibit 7 (e.g., L-1 through L-100) where the bond projecting to the left is connected to G of Formula 1. For instance, the first compound listed in Table 7a is a compound of Formula 1 wherein C(=W²)Z is L and L is L-1 (e.g. W² is NOR¹², R¹² is H and Z is H) and there is no $(R^{9a})_p$ substituent.
E is E-1a.

The present disclosure also includes Table 8b through 8v, each of which is constructed the same as Table 8a above except that the Table Heading in Table 8a (i.e. "E is E-1a") is replaced with the respective table headings shown below. For example, in Table 8b the table heading is "E is E-1b". L, $(R^{9a})_p$, X, n and $R^{6b}$ are as defined in Table 8a above. Thus, the first entry in Table 8b specifically discloses a compound of Formula 1 wherein L is L-1 and there is no value for $(R^{9a})_p$ substituent.

| Table | Table Heading |
|---|---|
| 8b | E is E-1b |
| 8c | E is E-1c |
| 8d | E is E-1d |
| 8e | E is E-1e |
| 8f | E is E-1f |
| 8g | E is E-1g |
| 8h | E is E-1h |
| 8i | E is E-1i |
| 8j | E is E-1j |
| 8k | E is E-1k |
| 8l | E is E-1l |
| 8m | E is E-1m |
| 8n | E is E-1n |
| 8o | E is E-2a |
| 8p | E is E-2b |
| 8q | E is E-2c |
| 8r | E is E-2d |
| 8s | E is E-3a |
| 8t | E is E-3b |
| 8u | E is E-3c |
| 8v | E is E-3d |

Formulation/Utility

A compound of Formula 1 of this invention (including N-oxides and salts thereof) will generally be used as a fungicidal active ingredient in a composition, i.e. formulation, with at least one additional component selected from the group consisting of surfactants, solid diluents and liquid diluents, which serve as a carrier. The formulation or composition ingredients are selected to be consistent with the physical properties of the active ingredient, mode of application and environmental factors such as soil type, moisture and temperature.

Useful formulations include both liquid and solid compositions. Liquid compositions include solutions (including emulsifiable concentrates), suspensions, emulsions (including microemulsions and/or suspoemulsions) and the like, which optionally can be thickened into gels. The general types of aqueous liquid compositions are soluble concentrate, suspension concentrate, capsule suspension, concentrated emulsion, microemulsion and suspo-emulsion. The general types of nonaqueous liquid compositions are emulsifiable concentrate, microemulsifiable concentrate, dispersible concentrate and oil dispersion.

The general types of solid compositions are dusts, powders, granules, pellets, prills, pastilles, tablets, filled films (including seed coatings) and the like, which can be water-dispersible ("wettable") or water-soluble. Films and coatings formed from film-forming solutions or flowable suspensions are particularly useful for seed treatment. Active ingredient can be (micro)encapsulated and further formed into a suspension or solid formulation; alternatively the entire formulation of active ingredient can be encapsulated (or "overcoated"). Encapsulation can control or delay release of the active ingredient. An emulsifiable granule combines the advantages of both an emulsifiable concentrate formulation and a dry granular formulation. High-strength compositions are primarily used as intermediates for further formulation.

Sprayable formulations are typically extended in a suitable medium before spraying. Such liquid and solid formulations are formulated to be readily diluted in the spray medium, usually water. Spray volumes can range from about one to several thousand liters per hectare, but more typically are in the range from about ten to several hundred liters per hectare. Sprayable formulations can be tank mixed with water or another suitable medium for foliar treatment by aerial or ground application, or for application to the growing medium of the plant. Liquid and dry formulations can be metered directly into drip irrigation systems or metered into the furrow during planting. Liquid and solid formulations can be applied onto seeds of crops and other desirable vegetation as seed treatments before planting to protect developing roots and other subterranean plant parts and/or foliage through systemic uptake.

The formulations will typically contain effective amounts of active ingredient, diluent and surfactant within the following approximate ranges which add up to 100 percent by weight.

|  | Weight Percent | | |
| --- | --- | --- | --- |
|  | Active Ingredient | Diluent | Surfactant |
| Water-Dispersible and Water-soluble Granules, Tablets and Powders | 0.001-90 | 0-99.999 | 0-15 |
| Oil Dispersions, Suspensions, Emulsions, Solutions (including Emulsifiable Concentrates) | 1-50 | 40-99 | 0-50 |
| Dusts | 1-25 | 70-99 | 0-5 |
| Granules and Pellets | 0.001-95 | 5-99.999 | 0-15 |
| High Strength Compositions | 90-99 | 0-10 | 0-2 |

Solid diluents include, for example, clays such as bentonite, montmorillonite, attapulgite and kaolin, gypsum, cellulose, titanium dioxide, zinc oxide, starch, dextrin, sugars (e.g., lactose, sucrose), silica, talc, mica, diatomaceous earth, urea, calcium carbonate, sodium carbonate and bicarbonate, and sodium sulfate. Typical solid diluents are described in Watkins et al., *Handbook of Insecticide Dust Diluents and Carriers*, 2nd Ed., Dorland Books, Caldwell, N.J.

Liquid diluents include, for example, water, N,N-dimethylalkanamides (e.g., N,N-dimethylformamide), limonene, dimethyl sulfoxide, N-alkylpyrrolidones (e.g., N-methylpyrrolidinone), ethylene glycol, triethylene glycol, propylene glycol, dipropylene glycol, polypropylene glycol, propylene carbonate, butylene carbonate, paraffins (e.g., white mineral oils, normal paraffins, isoparaffins), alkylbenzenes, alkylnaphthalenes, glycerine, glycerol triacetate, sorbitol, aromatic hydrocarbons, dearomatized aliphatics, alkylbenzenes, alkylnaphthalenes, ketones such as cyclohexanone, 2-heptanone, isophorone and 4-hydroxy-4-methyl-2-pentanone, acetates such as isoamyl acetate, hexyl acetate, heptyl acetate, octyl acetate, nonyl acetate, tridecyl acetate and isobornyl acetate, other esters such as alkylated lactate esters, dibasic esters and γ-butyrolactone, and alcohols, which can be linear, branched, saturated or unsaturated, such as methanol, ethanol, n-propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol and benzyl alcohol. Liquid diluents also include glycerol esters of saturated and unsaturated fatty acids (typically $C_6$-$C_{22}$), such as plant seed and fruit oils (e.g., oils of olive, castor, linseed, sesame, corn (maize), peanut, sunflower, grapeseed, safflower, cottonseed, soybean, rapeseed, coconut and palm kernel), animal-sourced fats (e.g., beef tallow, pork tallow, lard, cod liver oil, fish oil), and mixtures thereof. Liquid diluents also include alkylated fatty acids (e.g., methylated, ethylated, butylated) wherein the fatty acids may be obtained by hydrolysis of glycerol esters from plant and animal sources, and can be purified by distillation. Typical liquid diluents are described in Marsden, *Solvents Guide*, 2nd Ed., Interscience, New York, 1950.

The solid and liquid compositions of the present invention often include one or more surfactants. When added to a liquid, surfactants (also known as "surface-active agents") generally modify, most often reduce, the surface tension of the liquid. Depending on the nature of the hydrophilic and lipophilic groups in a surfactant molecule, surfactants can be useful as wetting agents, dispersants, emulsifiers or defoaming agents.

Surfactants can be classified as nonionic, anionic or cationic. Nonionic surfactants useful for the present compositions include, but are not limited to: alcohol alkoxylates such as alcohol alkoxylates based on natural and synthetic alcohols (which may be branched or linear) and prepared from the alcohols and ethylene oxide, propylene oxide, butylene oxide or mixtures thereof; amine ethoxylates, alkanolamides and ethoxylated alkanolamides; alkoxylated triglycerides such as ethoxylated soybean, castor and rapeseed oils; alkylphenol alkoxylates such as octylphenol ethoxylates, nonylphenol ethoxylates, dinonyl phenol ethoxylates and dodecyl phenol ethoxylates (prepared from the phenols and ethylene oxide, propylene oxide, butylene oxide or mixtures thereof); block polymers prepared from ethylene oxide or propylene oxide and reverse block polymers where the terminal blocks are prepared from propylene oxide; ethoxylated fatty acids; ethoxylated fatty esters and oils; ethoxylated methyl esters; ethoxylated tristyrylphenol (including those prepared from ethylene oxide, propylene oxide, butylene oxide or mixtures thereof); fatty acid esters, glycerol esters, lanolin-based derivatives, polyethoxylate esters such as polyethoxylated sorbitan fatty acid esters, polyethoxylated sorbitol fatty acid esters and polyethoxylated glycerol fatty acid esters; other sorbitan derivatives such as sorbitan esters; polymeric surfactants such as random copolymers, block copolymers, alkyd peg (polyethylene glycol) resins, graft or comb polymers and star polymers; polyethylene glycols (pegs); polyethylene glycol fatty acid esters; silicone-based surfactants; and sugar-derivatives such as sucrose esters, alkyl polyglycosides and alkyl polysaccharides.

Useful anionic surfactants include, but are not limited to: alkylaryl sulfonic acids and their salts; carboxylated alcohol or alkylphenol ethoxylates; diphenyl sulfonate derivatives; lignin and lignin derivatives such as lignosulfonates; maleic or succinic acids or their anhydrides; olefin sulfonates; phosphate esters such as phosphate esters of alcohol alkoxylates, phosphate esters of alkylphenol alkoxylates and phosphate esters of styryl phenol ethoxylates; protein-based surfactants; sarcosine derivatives; styryl phenol ether sulfate; sulfates and sulfonates of oils and fatty acids; sulfates and sulfonates of ethoxylated alkylphenols; sulfates of alcohols; sulfates of ethoxylated alcohols; sulfonates of amines and amides such as N,N-alkyltaurates; sulfonates of benzene, cumene, toluene, xylene, and dodecyl and tridecylbenzenes; sulfonates of condensed naphthalenes; sulfonates of naphthalene and alkyl naphthalene; sulfonates of fractionated petroleum; sulfosuccinamates; and sulfosuccinates and their derivatives such as dialkyl sulfosuccinate salts.

Useful cationic surfactants include, but are not limited to: amides and ethoxylated amides; amines such as N-alkyl propanediamines, tripropylenetriamines and dipropylenetetramines, and ethoxylated amines, ethoxylated diamines and propoxylated amines (prepared from the amines and ethylene oxide, propylene oxide, butylene oxide or mixtures thereof); amine salts such as amine acetates and diamine salts; quaternary ammonium salts such as quaternary salts, ethoxylated quaternary salts and diquaternary salts; and amine oxides such as alkyldimethylamine oxides and bis-(2-hydroxyethyl)-alkylamine oxides.

Also useful for the present compositions are mixtures of nonionic and anionic surfactants or mixtures of nonionic and cationic surfactants. Nonionic, anionic and cationic surfactants and their recommended uses are disclosed in a variety of published references including *McCutcheon's Emulsifiers and Detergents*, annual American and International Editions published by McCutcheon's Division, The Manufacturing Confectioner Publishing Co.; Sisely and Wood, *Encyclopedia of Surface Active Agents*, Chemical Publ. Co., Inc., New York, 1964; and A. S. Davidson and B. Milwidsky, *Synthetic Detergents*, Seventh Edition, John Wiley and Sons, New York, 1987.

Compositions of this invention may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in *McCutcheon's Volume 2: Functional Materials*, annual International and North American editions published by McCutcheon's Division, The Manufacturing Confectioner Publishing Co.; and PCT Publication WO 03/024222.

The compound of Formula 1 and any other active ingredients are typically incorporated into the present compositions by dissolving the active ingredient in a solvent or by grinding in a liquid or dry diluent. Solutions, including emulsifiable concentrates, can be prepared by simply mixing the ingredients. If the solvent of a liquid composition intended for use as an emulsifiable concentrate is water-immiscible, an emulsifier is typically added to emulsify the active-containing solvent upon dilution with water. Active ingredient slurries, with particle diameters of up to 2,000 μm can be wet milled using media mills to obtain particles with average diameters below 3 μm. Aqueous slurries can be made into finished suspension concentrates (see, for example, U.S. Pat. No. 3,060,084) or further processed by spray drying to form water-dispersible granules. Dry formulations usually require dry milling processes, which produce average particle diameters in the 2 to 10 μm range. Dusts and powders can be prepared by blending and usually grinding (such as with a hammer mill or fluid-energy mill). Granules and pellets can be prepared by spraying the active material upon preformed granular carriers or by agglomeration techniques. See Browning, "Agglomeration", *Chemical Engineering*, Dec. 4, 1967, pp 147-48, *Perry's Chemical Engineer's Handbook*, 4th Ed., McGraw-Hill, New York, 1963, pages 8-57 and following, and WO 91/13546. Pellets can be prepared as described in U.S. Pat. No. 4,172,714. Water-dispersible and water-soluble granules can be prepared as taught in U.S. Pat. No. 4,144,050, U.S. Pat. No. 3,920,442 and DE 3,246,493. Tablets can be prepared as taught in U.S. Pat. No. 5,180,587, U.S. Pat. No. 5,232,701 and U.S. Pat. No. 5,208,030. Films can be prepared as taught in GB 2,095,558 and U.S. Pat. No. 3,299,566.

For further information regarding the art of formulation, see T. S. Woods, "The Formulator's Toolbox—Product Forms for Modern Agriculture" in *Pesticide Chemistry and Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; Hance et al., *Weed Control Handbook*, 8th Ed., Blackwell Scientific Publications, Oxford, 1989; and *Developments in formulation technology*, PJB Publications, Richmond, UK, 2000.

In the following Examples, all percentages are by weight and all formulations are prepared in conventional ways. Compound numbers refer to compounds in Index Tables A-B. Without further elaboration, it is believed that one skilled in the art using the preceding description can utilize the present invention to its fullest extent. The following Examples are, therefore, to be constructed as merely illustrative, and not limiting of the disclosure in any way whatsoever. Percentages are by weight except where otherwise indicated.

Example A

High Strength Concentrate

| | |
|---|---|
| Compound 11 | 98.5% |
| silica aerogel | 0.5% |
| synthetic amorphous fine silica | 1.0% |

Example B

Wettable Powder

| | |
|---|---|
| Compound 13 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0% |

Example C

Granule

| | |
|---|---|
| Compound 23 | 10.0% |
| attapulgite granules (low volatile matter, 0.71/0.30 mm; U.S.S. No. 25-50 sieves) | 90.0% |

Example D

Extruded Pellet

| | |
|---|---|
| Compound 19 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

Example E

Emulsifiable Concentrate

| | |
|---|---|
| Compound 22 | 10.0% |
| polyoxyethylene sorbitol hexoleate | 20.0% |
| $C_6$-$C_{10}$ fatty acid methyl ester | 70.0% |

Example F

Microemulsion

| | |
|---|---|
| Compound 18 | 5.0% |
| polyvinylpyrrolidone-vinyl acetate copolymer | 30.0% |
| alkylpolyglycoside | 30.0% |
| glyceryl monooleate | 15.0% |
| water | 20.0% |

Example G

Seed Treatment

| | |
|---|---|
| Compound 11 | 20.00% |
| polyvinylpyrrolidone-vinyl acetate copolymer | 5.00% |
| montan acid wax | 5.00% |
| calcium ligninsulfonate | 1.00% |
| polyoxyethylene/polyoxypropylene block copolymers | 1.00% |
| stearyl alcohol (POE 20) | 2.00% |
| polyorganosilane | 0.20% |
| colorant red dye | 0.05% |
| water | 65.75% |

Water-soluble and water-dispersible formulations are typically diluted with water to form aqueous compositions before application. Aqueous compositions for direct applications to the plant or portion thereof (e.g., spray tank compositions) typically at least about 1 ppm or more (e.g., from 1 ppm to 100 ppm) of the compound(s) of this invention.

The compounds of this invention are useful as plant disease control agents. The present invention therefore further comprises a method for controlling plant diseases caused by fungal plant pathogens comprising applying to the plant or portion thereof to be protected, or to the plant seed to be protected, an effective amount of a compound of the invention or a fungicidal composition containing said compound. The compounds and/or compositions of this invention provide control of diseases caused by a broad spectrum of fungal plant pathogens in the Basidiomycete, Ascomycete, Oomycete and Deuteromycete classes. They are effective in controlling a broad spectrum of plant diseases, particularly foliar pathogens of ornamental, turf, vegetable, field, cereal, and fruit crops. These pathogens include: Oomycetes, including *Phytophthora* diseases such as *Phytophthora infestans*, *Phytophthora megasperma*, *Phytophthora parasitica*, *Phytophthora cinnamomi* and *Phytophthora capsici*, *Pythium* diseases such as *Pythium aphanidermatum*, and diseases in the Peronosporaceae family such as *Plasmopara viticola*, *Peronospora* spp. (including *Peronospora tabacina* and *Peronospora parasitica*), *Pseudoperonospora* spp. (including *Pseudoperonospora cubensis*) and *Bremia lactucae*; Ascomycetes, including *Alternaria* diseases such as *Alternaria solani* and *Alternaria brassicae*, *Guignardia* diseases such as *Guignardia bidwell*, *Venturia* diseases such as *Venturia inaequalis*, *Septoria* diseases such as *Septoria nodorum* and *Septoria tritici*, powdery mildew diseases such as *Erysiphe* spp. (including *Erysiphe graminis* and *Erysiphe polygoni*), *Uncinula necatur*, *Sphaerotheca fuligena* and *Podosphaera leucotricha*, *Pseudocercosporella herpotrichoides*, *Botrytis* diseases such as *Botrytis cinerea*, *Monilinia fructicola*, *Sclerotinia* diseases such as *Sclerotinia sclerotiorum*, *Magnaporthe grisea*, *Phomopsis viticola*, *Helminthosporium* diseases such as *Helminthosporium tritici repentis*, *Pyrenophora teres*, anthracnose diseases such as *Glomerella* or *Colletotrichum* spp. (such as *Colletotrichum graminicola* and *Colletotrichum orbiculare*), and *Gaeumannomyces graminis*; Basidiomycetes, including rust diseases caused by *Puccinia* spp. (such as *Puccinia recondite*, *Puccinia striiformis*, *Puccinia hordei*, *Puccinia graminis* and *Puccinia arachidis*), *Hemileia vastatrix* and *Phakopsora pachyrhizi*; other pathogens including *Rutstroemia floccosum* (also known as *Sclerontina homoeocarpa*); *Rhizoctonia* spp. (such as *Rhizoctonia solani*); *Fusarium* diseases such as *Fusarium roseum*, *Fusarium graminearum* and *Fusarium oxysporum*; *Verticillium dahliae*; *Sclerotium rolfsii*; *Rynchosporium secalis*;

*Cercosporidium personatum, Cercospora arachidicola* and *Cercospora beticola*; and other genera and species closely related to these pathogens. In addition to their fungicidal activity, the compositions or combinations also have activity against bacteria such as *Erwinia amylovora, Xanthomonas campestris, Pseudomonas syringae*, and other related species.

Plant disease control is ordinarily accomplished by applying an effective amount of a compound of this invention either pre- or post-infection, to the portion of the plant to be protected such as the roots, stems, foliage, fruit, seeds, tubers or bulbs, or to the media (soil or sand) in which the plants to be protected are growing. The compounds can also be applied to seeds to protect the seeds and seedlings developing from the seeds. The compounds can also be applied through irrigation water to treat plants.

Rates of application for these compounds (i.e. a fungicidally effective amount) can be influenced by factors such as the plant diseases to be controlled, the plant species to be protected, ambient moisture and temperature and should be determined under actual use conditions. One skilled in the art can easily determine through simple experimentation the fungicidally effective amount necessary for the desired level of plant disease control. Foliage can normally be protected when treated at a rate of from less than about 1 g/ha to about 5,000 g/ha of active ingredient. Seed and seedlings can normally be protected when seed is treated at a rate of from about 0.1 to about 10 g per kilogram of seed.

Compounds of this invention can also be mixed with one or more other biologically active compounds or agents including fungicides, insecticides, nematocides, bactericides, acaricides, herbicides, herbicide safeners, growth regulators such as insect molting inhibitors and rooting stimulants, chemosterilants, semiochemicals, repellents, attractants, pheromones, feeding stimulants, plant nutrients, other biologically active compounds or entomopathogenic bacteria, virus or fungi to form a multi-component pesticide giving an even broader spectrum of agricultural protection. Thus the present invention also pertains to a composition comprising a compound of Formula 1 (in a fungicidally effective amount) and at least one additional biologically active compound or agent (in a biologically effective amount) and can further comprise at least one of a surfactant, a solid diluent or a liquid diluent. The other biologically active compounds or agents can be formulated in compositions comprising at least one of a surfactant, solid or liquid diluent. For mixtures of the present invention, one or more other biologically active compounds or agents can be formulated together with a compound of Formula 1, to form a premix, or one or more other biologically active compounds or agents can be formulated separately from the compound of Formula 1, and the formulations combined together before application (e.g., in a spray tank) or, alternatively, applied in succession.

Of note is a composition which in addition to the compound of Formula 1 include at least one fungicidal compound selected from the group consisting of the classes (1) methyl benzimidazole carbamate (MBC) fungicides; (2) dicarboximide fungicides; (3) demethylation inhibitor (DMI) fungicides; (4) phenylamide fungicides; (5) amine/morpholine fungicides; (6) phospholipid biosynthesis inhibitor fungicides; (7) carboxamide fungicides; (8) hydroxy(2-amino-) pyrimidine fungicides; (9) anilinopyrimidine fungicides; (10) N-phenyl carbamate fungicides; (11) quinone outside inhibitor (QoI) fungicides; (12) phenylpyrrole fungicides; (13) quinoline fungicides; (14) lipid peroxidation inhibitor fungicides; (15) melanin biosynthesis inhibitors-reductase (MBI-R) fungicides; (16) melanin biosynthesis inhibitors-dehydratase (MBI-D) fungicides; (17) hydroxyanilide fungicides; (18) squalene-epoxidase inhibitor fungicides; (19) polyoxin fungicides; (20) phenylurea fungicides; (21) quinone inside inhibitor (QiI) fungicides; (22) benzamide fungicides; (23) enopyranuronic acid antibiotic fungicides; (24) hexopyranosyl antibiotic fungicides; (25) glucopyranosyl antibiotic: protein synthesis fungicides; (26) glucopyranosyl antibiotic: trehalase and inositol biosynthesis fungicides; (27) cyanoacetamideoxime fungicides; (28) carbamate fungicides; (29) oxidative phosphorylation uncoupling fungicides; (30) organo tin fungicides; (31) carboxylic acid fungicides; (32) heteroaromatic fungicides; (33) phosphonate fungicides; (34) phthalamic acid fungicides; (35) benzotriazine fungicides; (36) benzene-sulfonamide fungicides; (37) pyridazinone fungicides; (38) thiophene-carboxamide fungicides; (39) pyrimidinamide fungicides; (40) carboxylic acid amide (CAA) fungicides; (41) tetracycline antibiotic fungicides; (42) thiocarbamate fungicides; (43) benzamide fungicides; (44) host plant defense induction fungicides; (45) multi-site contact activity fungicides; (46) fungicides other than classes (1) through (45); and salts of compounds of classes (1) through (46).

Further descriptions of these classes of fungicidal compounds are provided below.

(1) "Methyl benzimidazole carbamate (MBC) fungicides" (Fungicide Resistance Action Committee (FRAC) code 1) inhibit mitosis by binding to β-tubulin during microtubule assembly. Inhibition of microtubule assembly can disrupt cell division, transport within the cell and cell structure. Methyl benzimidazole carbamate fungicides include benzimidazole and thiophanate fungicides. The benzimidazoles include benomyl, carbendazim, fuberidazole and thiabendazole. The thiophanates include thiophanate and thiophanate-methyl.

(2) "Dicarboximide fungicides" (Fungicide Resistance Action Committee (FRAC) code 2) are proposed to inhibit a lipid peroxidation in fungi through interference with NADH cytochrome c reductase. Examples include chlozolinate, iprodione, procymidone and vinclozolin.

(3) "Demethylation inhibitor (DMI) fungicides" (Fungicide Resistance Action Committee (FRAC) code 3) inhibit C14-demethylase, which plays a role in sterol production. Sterols, such as ergosterol, are needed for membrane structure and function, making them essential for the development of functional cell walls. Therefore, exposure to these fungicides results in abnormal growth and eventually death of sensitive fungi. DMI fungicides are divided between several chemical classes: azoles (including triazoles and imidazoles), pyrimidines, piperazines and pyridines. The triazoles include azaconazole, bitertanol, bromuconazole, cyproconazole, difenoconazole, diniconazole (including diniconazole-M), epoxiconazole, fenbuconazole, fluquinconazole, flusilazole, flutriafol, hexaconazole, imibenconazole, ipconazole, metconazole, myclobutanil, penconazole, propiconazole, prothioconazole, simeconazole, tebuconazole, tetraconazole, triadimefon, triadimenol, triticonazole and uniconazole. The imidazoles include clotrimazole, imazalil, oxpoconazole, prochloraz, pefurazoate and triflumizole. The pyrimidines include fenarimol and nuarimol. The piperazines include triforine. The pyridines include pyrifenox. Biochemical investigations have shown that all of the above mentioned fungicides are DMI fungicides as described by K. H. Kuck et al. in *Modern Selective Fungicides—Properties, Applications and Mechanisms of Action*, H. Lyr (Ed.), Gustav Fischer Verlag: New York, 1995, 205-258.

(4) "Phenylamide fungicides" (Fungicide Resistance Action Committee (FRAC) code 4) are specific inhibitors of RNA polymerase in Oomycete fungi. Sensitive fungi exposed to these fungicides show a reduced capacity to incorporate uridine into rRNA. Growth and development in sensitive fungi is prevented by exposure to this class of fungicide. Phenylamide fungicides include acylalanine, oxazolidinone and butyrolactone fungicides. The acylalanines include benalaxyl, benalaxyl-M, furalaxyl, metalaxyl and metalaxyl-M/mefenoxam. The oxazolidinones include oxadixyl. The butyrolactones include ofurace.

(5) "Amine/morpholine fungicides" (Fungicide Resistance Action Committee (FRAC) code 5) inhibit two target sites within the sterol biosynthetic pathway, $\Delta^8 \rightarrow \Delta^7$ isomerase and $\Delta^{14}$ reductase. Sterols, such as ergosterol, are needed for membrane structure and function, making them essential for the development of functional cell walls. Therefore, exposure to these fungicides results in abnormal growth and eventually death of sensitive fungi. Amine/morpholine fungicides (also known as non-DMI sterol biosynthesis inhibitors) include morpholine, piperidine and spiroketal-amine fungicides. The morpholines include aldimorph, dodemorph, fenpropimorph, tridemorph and trimorphamide. The piperidines include fenpropidin and piperalin. The spiroketal-amines include spiroxamine.

(6) "Phospholipid biosynthesis inhibitor fungicides" (Fungicide Resistance Action Committee (FRAC) code 6) inhibit growth of fungi by affecting phospholipid biosynthesis. Phospholipid biosynthesis fungicides include phophorothiolate and dithiolane fungicides. The phosphorothiolates include edifenphos, iprobenfos and pyrazophos. The dithiolanes include isoprothiolane.

(7) "Carboxamide fungicides" (Fungicide Resistance Action Committee (FRAC) code 7) inhibit Complex II (succinate dehydrogenase) fungal respiration by disrupting a key enzyme in the Krebs Cycle (TCA cycle) named succinate dehydrogenase. Inhibiting respiration prevents the fungus from making ATP, and thus inhibits growth and reproduction. Carboxamide fungicides include benzamides, furan carboxamides, oxathiin carboxamides, thiazole carboxamides, pyrazole carboxamides and pyridine carboxamides. The benzamides include benodanil, flutolanil and mepronil. The furan carboxamides include fenfuram. The oxathiin carboxamides include carboxin and oxycarboxin. The thiazole carboxamides include thifluzamide. The pyrazole carboxamides include furametpyr, penthiopyrad, bixafen, isopyrazam, N-[2-(1S,2R)-[1,1'-bicyclopropyl]-2-ylphenyl]-3-(difluoromethyl)-1-methyl-1H-pyrazole-4-carboxamide and penflufen (N-[2-(1,3-dimethyl-butyl)phenyl]-5-fluoro-1,3-dimethyl-1H-pyrazole-4-carboxamide). The pyridine carboxamides include boscalid.

(8) "Hydroxy(2-amino-)pyrimidine fungicides" (Fungicide Resistance Action Committee (FRAC) code 8) inhibit nucleic acid synthesis by interfering with adenosine deaminase. Examples include bupirimate, dimethirimol and ethirimol.

(9) "Anilinopyrimidine fungicides" (Fungicide Resistance Action Committee (FRAC) code 9) are proposed to inhibit biosynthesis of the amino acid methionine and to disrupt the secretion of hydrolytic enzymes that lyse plant cells during infection. Examples include cyprodinil, mepanipyrim and pyrimethanil.

(10) "N-Phenyl carbamate fungicides" (Fungicide Resistance Action Committee (FRAC) code 10) inhibit mitosis by binding to β-tubulin and disrupting microtubule assembly. Inhibition of microtubule assembly can disrupt cell division, transport within the cell and cell structure. Examples include diethofencarb.

(11) "Quinone outside inhibitor (QoI) fungicides" (Fungicide Resistance Action Committee (FRAC) code 11) inhibit Complex III mitochondrial respiration in fungi by affecting ubiquinol oxidase. Oxidation of ubiquinol is blocked at the "quinone outside" ($Q_O$) site of the cytochrome $bc_1$ complex, which is located in the inner mitochondrial membrane of fungi. Inhibiting mitochondrial respiration prevents normal fungal growth and development. Quinone outside inhibitor fungicides (also known as strobilurin fungicides) include methoxyacrylate, methoxycarbamate, oximinoacetate, oximinoacetamide, oxazolidinedione, dihydrodioxazine, imidazolinone and benzylcarbamate fungicides. The methoxyacrylates include azoxystrobin, enestroburin (SYP-Z071), picoxystrobin and pyraoxystrobin (SYP-3343). The methoxycarbamates include pyraclostrobin and pyrametostrobin (SYP-4155). The oximinoacetates include kresoxim-methyl and trifloxystrobin. The oximinoacetamides include dimoxystrobin, metominostrobin, orysastrobin, α-[methoxyimino]-N-methyl-2-[[[1-[3-(trifluoromethyl)phenyl]ethoxy]imino]-methyl]benzeneacetamide and 2-[[[3-(2,6-dichlorophenyl)-1-methyl-2-propen-1-ylidene]-amino]oxy]methyl]-α-(methoxyimino)-N-methylbenzeneacetamide.

The oxazolidinediones include famoxadone. The dihydrodioxazines include fluoxastrobin. The imidazolinones include fenamidone. The benzylcarbamates include pyribencarb.

(12) "Phenylpyrrole fungicides" (Fungicide Resistance Action Committee (FRAC) code 12) inhibit a MAP protein kinase associated with osmotic signal transduction in fungi. Fenpiclonil and fludioxonil are examples of this fungicide class.

(13) "Quinoline fungicides" (Fungicide Resistance Action Committee (FRAC) code 13) are proposed to inhibit signal transduction by affecting G-proteins in early cell signaling. They have been shown to interfere with germination and/or appressorium formation in fungi that cause powder mildew diseases. Quinoxyfen and tebufloquin are examples of this class of fungicide.

(14) "Lipid peroxidation inhibitor fungicides" (Fungicide Resistance Action Committee (FRAC) code 14) are proposed to inhibit lipid peroxidation which affects membrane synthesis in fungi. Members of this class, such as etridiazole, may also affect other biological processes such as respiration and melanin biosynthesis. Lipid peroxidation fungicides include aromatic carbon and 1,2,4-thiadiazole fungicides. The aromatic carbon fungicides include biphenyl, chloroneb, dicloran, quintozene, tecnazene and tolclofos-methyl. The 1,2,4-thiadiazole fungicides include etridiazole.

(15) "Melanin biosynthesis inhibitors-reductase (MBI-R) fungicides" (Fungicide Resistance Action Committee (FRAC) code 16.1) inhibit the naphthal reduction step in melanin biosynthesis. Melanin is required for host plant infection by some fungi. Melanin biosynthesis inhibitors-reductase fungicides include isobenzofuranone, pyrroloquinolinone and triazolobenzothiazole fungicides. The isobenzofuranones include fthalide. The pyrroloquinolinones include pyroquilon. The triazolobenzothiazoles include tricyclazole.

(16) "Melanin biosynthesis inhibitors-dehydratase (MBI-D) fungicides" (Fungicide Resistance Action Committee (FRAC) code 16.2) inhibit scytalone dehydratase in melanin biosynthesis. Melanin in required for host plant infection by some fungi. Melanin biosynthesis inhibitors-dehydratase fungicides include cyclopropanecarboxamide, carboxamide and propionamide fungicides. The cyclopropanecarboxamides include carpropamid. The carboxamides include diclocymet. The propionamides include fenoxanil.

(17) "Hydroxyanilide fungicides (Fungicide Resistance Action Committee (FRAC) code 17) inhibit C4-demethylase which plays a role in sterol production. Examples include fenhexamid.

(18) "Squalene-epoxidase inhibitor fungicides" (Fungicide Resistance Action Committee (FRAC) code 18) inhibit squalene-epoxidase in ergosterol biosynthesis pathway. Sterols such as ergosterol are needed for membrane structure and function, making them essential for the development of functional cell walls. Therefore exposure to these fungicides results in abnormal growth and eventually death of sensitive fungi. Squalene-epoxidase inhibitor fungicides include thiocarbamate and allylamine fungicides. The thiocarbamates include pyributicarb. The allylamines include naftifine and terbinafine.

(19) "Polyoxin fungicides" (Fungicide Resistance Action Committee (FRAC) code 19) inhibit chitin synthase. Examples include polyoxin.

(20) "Phenylurea fungicides" (Fungicide Resistance Action Committee (FRAC) code 20) are proposed to affect cell division. Examples include pencycuron.

(21) "Quinone inside inhibitor (QiI) fungicides" (Fungicide Resistance Action Committee (FRAC) code 21) inhibit Complex III mitochondrial respiration in fungi by affecting ubiquinol reductase. Reduction of ubiquinol is blocked at the "quinone inside" ($Q_i$) site of the cytochrome $bc_1$ complex, which is located in the inner mitochondrial membrane of fungi. Inhibiting mitochondrial respiration prevents normal fungal growth and development. Quinone inside inhibitor fungicides include cyanoimidazole and sulfamoyltriazole fungicides. The cyanoimidazoles include cyazofamid. The sulfamoyltriazoles include amisulbrom.

(22) "Benzamide fungicides" (Fungicide Resistance Action Committee (FRAC) code 22) inhibit mitosis by binding to β-tubulin and disrupting microtubule assembly Inhibition of microtubule assembly can disrupt cell division, transport within the cell and cell structure. Examples include zoxamide.

(23) "Enopyranuronic acid antibiotic fungicides" (Fungicide Resistance Action Committee (FRAC) code 23) inhibit growth of fungi by affecting protein biosynthesis. Examples include blasticidin-S.

(24) "Hexopyranosyl antibiotic fungicides" (Fungicide Resistance Action Committee (FRAC) code 24) inhibit growth of fungi by affecting protein biosynthesis. Examples include kasugamycin.

(25) "Glucopyranosyl antibiotic: protein synthesis fungicides" (Fungicide Resistance Action Committee (FRAC) code 25) inhibit growth of fungi by affecting protein biosynthesis. Examples include streptomycin.

(26) "Glucopyranosyl antibiotic: trehalase and inositol biosynthesis fungicides" (Fungicide Resistance Action Committee (FRAC) code 26) inhibit trehalase in inositol biosynthesis pathway. Examples include validamycin.

(27) "Cyanoacetamideoxime fungicides (Fungicide Resistance Action Committee (FRAC) code 27) include cymoxanil.

(28) "Carbamate fungicides" (Fungicide Resistance Action Committee (FRAC) code 28) are considered multi-site inhibitors of fungal growth. They are proposed to interfere with the synthesis of fatty acids in cell membranes, which then disrupts cell membrane permeability. Propamacarb, propamacarb-hydrochloride, iodocarb, and prothiocarb are examples of this fungicide class.

(29) "Oxidative phosphorylation uncoupling fungicides" (Fungicide Resistance Action Committee (FRAC) code 29) inhibit fungal respiration by uncoupling oxidative phosphorylation. Inhibiting respiration prevents normal fungal growth and development. This class includes 2,6-dinitroanilines such as fluazinam, pyrimidonehydrazones such as ferimzone and dinitrophenyl crotonates such as dinocap, meptyldinocap and binapacryl.

(30) "Organo tin fungicides" (Fungicide Resistance Action Committee (FRAC) code 30) inhibit adenosine triphosphate (ATP) synthase in oxidative phosphorylation pathway. Examples include fentin acetate, fentin chloride and fentin hydroxide.

(31) "Carboxylic acid fungicides" (Fungicide Resistance Action Committee (FRAC) code 31) inhibit growth of fungi by affecting deoxyribonucleic acid (DNA) topoisomerase type II (gyrase). Examples include oxolinic acid.

(32) "Heteroaromatic fungicides" (Fungicide Resistance Action Committee (FRAC) code 32) are proposed to affect DNA/ribonucleic acid (RNA) synthesis. Heteroaromatic fungicides include isoxazole and isothiazolone fungicides. The isoxazoles include hymexazole and the isothiazolones include octhilinone.

(33) "Phosphonate fungicides" (Fungicide Resistance Action Committee (FRAC) code 33) include phosphorous acid and its various salts, including fosetyl-aluminum.

(34) "Phthalamic acid fungicides" (Fungicide Resistance Action Committee (FRAC) code 34) include teclofthalam.

(35) "Benzotriazine fungicides" (Fungicide Resistance Action Committee (FRAC) code 35) include triazoxide.

(36) "Benzene-sulfonamide fungicides" (Fungicide Resistance Action Committee (FRAC) code 36) include flusulfamide.

(37) "Pyridazinone fungicides" (Fungicide Resistance Action Committee (FRAC) code 37) include diclomezine.

(38) "Thiophene-carboxamide fungicides" (Fungicide Resistance Action Committee (FRAC) code 38) are proposed to affect ATP production. Examples include silthiofam.

(39) "Pyrimidinamide fungicides" (Fungicide Resistance Action Committee (FRAC) code 39) inhibit growth of fungi by affecting phospholipid biosynthesis and include diflumetorim.

(40) "Carboxylic acid amide (CAA) fungicides" (Fungicide Resistance Action Committee (FRAC) code 40) are proposed to inhibit phospholipid biosynthesis and cell wall deposition. Inhibition of these processes prevents growth and leads to death of the target fungus. Carboxylic acid amide fungicides include cinnamic acid amide, valinamide carbamate and mandelic acid amide fungicides. The cinnamic acid amides include dimethomorph and flumorph. The valinamide carbamates include benthiavalicarb, benthiavalicarb-isopropyl, iprovalicarb, valifenalate and valiphenal. The mandelic acid amides include mandipropamid, N-[2-[4-[[3-(4-chlorophenyl)-2-propyn-1-yl]oxy]-3-methoxyphenyl]ethyl]-3-methyl-2-[(methylsulfonyl)amino]butanamide and N-[2-[4-[[3-(4-chlorophenyl)-2-propyn-1-yl]oxy]-3-methoxyphenyl]ethyl]-3-methyl-2-[(ethylsulfonyl)amino]butanamide.

(41) "Tetracycline antibiotic fungicides" (Fungicide Resistance Action Committee (FRAC) code 41) inhibit growth of fungi by affecting complex 1 nicotinamide adenine dinucleotide (NADH) oxidoreductase. Examples include oxytetracycline.

(42) "Thiocarbamate fungicides (b42)" (Fungicide Resistance Action Committee (FRAC) code 42) include methasulfocarb.

(43) "Benzamide fungicides" (Fungicide Resistance Action Committee (FRAC) code 43) inhibit growth of fungi by delocalization of spectrin-like proteins. Examples include acylpicolide fungicides such as fluopicolide and fluopyram.

(44) "Host plant defense induction fungicides" (Fungicide Resistance Action Committee (FRAC) code P) induce host plant defense mechanisms. Host plant defense induction fungicides include benzo-thiadiazole, benzisothiazole and thiadiazole-carboxamide fungicides. The benzo-thiadiazoles include acibenzolar-S-methyl. The benzisothiazoles include probenazole. The thiadiazole-carboxamides include tiadinil and isotianil.

(45) "Multi-site contact fungicides" inhibit fungal growth through multiple sites of action and have contact/preventive activity. This class of fungicides includes: (45.1) "copper fungicides" (Fungicide Resistance Action Committee (FRAC) code M1)", (45.2) "sulfur fungicides" (Fungicide Resistance Action Committee (FRAC) code M2), (45.3) "dithiocarbamate fungicides" (Fungicide Resistance Action Committee (FRAC) code M3), (45.4) "phthalimide fungicides" (Fungicide Resistance Action Committee (FRAC) code M4), (45.5) "chloronitrile fungicides" (Fungicide Resistance Action Committee (FRAC) code M5), (45.6) "sulfamide fungicides" (Fungicide Resistance Action Committee (FRAC) code M6), (45.7) "guanidine fungicides" (Fungicide Resistance Action Committee (FRAC) code M7), (45.8) "triazine fungicides" (Fungicide Resistance Action Committee (FRAC) code M8) and (45.9) "quinone fungicides" (Fungicide Resistance Action Committee (FRAC) code M9). "Copper fungicides" are inorganic compounds containing copper, typically in the copper(II) oxidation state; examples include copper oxychloride, copper sulfate and copper hydroxide, including compositions such as Bordeaux mixture (tribasic copper sulfate). "Sulfur fungicides" are inorganic chemicals containing rings or chains of sulfur atoms; examples include elemental sulfur. "Dithiocarbamate fungicides" contain a dithiocarbamate molecular moiety; examples include mancozeb, metiram, propineb, ferbam, maneb, thiram, zineb and ziram. "Phthalimide fungicides" contain a phthalimide molecular moiety; examples include folpet, captan and captafol. "Chloronitrile fungicides" contain an aromatic ring substituted with chloro and cyano; examples include chlorothalonil. "Sulfamide fungicides" include dichlofluanid and tolyfluanid. "Guanidine fungicides" include dodine, guazatine, iminoctadine albesilate and iminoctadine triacetate. "Triazine fungicides" include anilazine. "Quinone fungicides" include dithianon.

(46) "Fungicides other than fungicides of classes (1) through (45)" include certain fungicides whose mode of action may be unknown. These include: (46.1) "thiazole carboxamide fungicides" (Fungicide Resistance Action Committee (FRAC) code U5), (46.2) "phenyl-acetamide fungicides" (Fungicide Resistance Action Committee (FRAC) code U6), (46.3) "quinazolinone fungicides" (Fungicide Resistance Action Committee (FRAC) code U7), (46.4) "benzophenone fungicides" (Fungicide Resistance Action Committee (FRAC) code U8) and (46.5) "triazolopyrimidine fungicides". The thiazole carboxamides include ethaboxam. The phenyl-acetamides include cyflufenamid and N-[[(cyclopropylmethoxy)-amino][6-(difluoromethoxy)-2,3-difluorophenyl]-methylene]benzeneacetamide. The quinazolinones include proquinazid. The benzophenones include metrafenone. The triazolopyrimidines include ametoctradin. The (b46) class also includes bethoxazin, fluxapyroxad, neoasozin (ferric methanearsonate), pyriofenone, pyrrolnitrin, quinomethionate, tebufloquin, N-[2-[4-[[3-(4-chlorophenyl)-2-propyn-1-yl]oxy]-3-methoxy-phenyl]ethyl]-3-methyl-2-[(methylsulfonyl)amino]butanamide, N-[2-[4-[[3-(4-chloro-phenyl)-2-propyn-1-yl]oxy]-3-methoxyphenyl] ethyl]-3-methyl-2-[(ethylsulfonyl)amino]-butanamide, 2-[[2-fluoro-5-(trifluoromethyl)phenyl]thio]-2-[3-(2-methoxyphenyl)-2-thiazo-lidinylidene]acetonitrile, 3-[5-(4-chlorophenyl)-2,3-dimethyl-3-isoxazolidinyl]pyridine, 4-fluorophenyl N-[1-[[[1-(4-cyanophenyl)ethyl]sulfonyl]methyl] propyl]carbamate, 5-chloro-6-(2,4,6-trifluorophenyl)-7-(4-methylpiperidin-1-yl)[1,2,4]triazolo[1,5-a]pyrimidine, N-(4-chloro-2-nitrophenyl)-N-ethyl-4-methylbenzenesulfonamide, N-[[(cyclopropylmethoxy)-amino][6-(difluoromethoxy)-2,3-difluorophenyl]methylene]benzeneacetamide, N-[4-[4-chloro-3-(trifluoromethyl)phenoxy]-2,5-dimethylphenyl]-N-ethyl-N-methylmethanimid-amide, 1-[(2-propenylthio)carbonyl]-2-(1-methylethyl)-4-(2-methylphenyl)-5-amino-1H-pyrazol-3-one, N-[9-(dichloromethylene)-1,2,3,4-tetrahydro-1,4-methanonaphthalen-5-yl]-3-(difluoromethyl)-1-methyl-1H-pyrazole-4-carboxamide, 3-(difluoromethyl)-N-[9-(difluoro-methylene)-1,2,3,4-tetrahydro-1,4-methanonaphthalen-5-yl]-1-methyl-1H-pyrazole-4-carboxamide, N-[9-(dibromomethylene)-1,2,3,4-tetrahydro-1,4-methanonaphthalen-5-yl]-3-(difluoromethyl)-1-methyl-1H-pyrazole-4-carboxamide, N-[9-(dibromomethylene)-1,2,3,4-tetrahydro-1,4-methanonaphthalen-5-yl]-1-methyl-3-(trifluoromethyl)-1H-pyrazole-4-carboxamide, N-[9-(difluoromethylene)-1,2,3,4-tetrahydro-1,4-methanonaphthalen-5-yl]-1-methyl-3-(trifluoromethyl)-1H-pyrazole-4-carboxamide and N-[9-(dichloromethylene)-1,2,3,4-tetrahydro-1,4-methanonaphthalen-5-yl]-1-methyl-3-(trifluoromethyl)-1H-pyrazole-4-carboxamide.

Therefore of note is a mixture (i.e. composition) comprising a compound of Formula 1 and at least one fungicidal compound selected from the group consisting of the aforedescribed classes (1) through (46). Also of note is a composition comprising said mixture (in fungicidally effective amount) and further comprising at least one additional component selected from the group consisting of surfactants, solid diluents and liquid diluents. Of particular note is a mixture (i.e. composition) comprising a compound of Formula 1 and at least one fungicidal compound selected from the group of specific compounds listed above in connection with classes (1) through (46). Also of particular note is a composition comprising said mixture (in fungicidally effective amount) and further comprising at least one additional surfactant selected from the group consisting of surfactants, solid diluents and liquid diluents.

Examples of other biologically active compounds or agents with which compounds of this invention can be formulated are: insecticides such as abamectin, acephate, acetamiprid, acrinathrin, amidoflumet (S-1955), avermectin, azadirachtin, azinphos-methyl, bifenthrin, bifenazate, buprofezin, carbofuran, cartap, chlorantraniliprole, chlorfenapyr, chlorfluazuron, chlorpyrifos, chlorpyrifos-methyl, chromafenozide, clothianidin, cyantraniliprole (3-bromo-1-(3-chloro-2-pyridinyl)-N-[4-cyano-2-methyl-6-[(methylamino) carbonyl]phenyl]-1H-pyrazole-5-carboxamide), cyflumetofen, cyfluthrin, beta-cyfluthrin, cyhalothrin, lambda-cyhalothrin, cypermethrin, cyromazine, deltamethrin, diafenthiuron, diazinon, dieldrin, diflubenzuron, dimefluthrin, dimethoate, dinotefuran, diofenolan, emamectin, endosulfan, esfenvalerate, ethiprole, fenothiocarb, fenoxycarb, fenpropathrin, fenvalerate, fipronil, flonicamid, flubendiamide, flucythrinate, tau-fluvalinate, flufenerim (UR-50701), flufenoxuron, fonophos, halofenozide, hexaflumuron, hydramethylnon, imidacloprid, indoxacarb, isofenphos, lufenuron, malathion, meperfluthrin, metaflumizone, metaldehyde, methamidophos, methidathion, methomyl, methoprene, methoxychlor, methoxyfenozide, metofluthrin, milbemycin oxime, monocrotophos, nicotine, nitenpyram, nithiazine, novaluron, noviflumuron (XDE-007), oxamyl, parathion, parathion-methyl, permethrin, phorate, phosalone, phosmet, phosphamidon, pirimicarb, profenofos, profluthrin, pymetrozine, pyrafluprole, pyrethrin, pyridalyl, pyrifluquinazon, pyriprole, pyriproxyfen, rotenone, ryanodine, spinetoram, spinosad, spirodiclofen, spiromesifen (BSN 2060), spirotetramat, sulfoxaflor, sulprofos, tebufenozide, teflubenzuron, tefluthrin, terbufos, tetrachlorvinphos, tetramethylfluthrin, thiacloprid, thiamethoxam, thiodicarb, thiosultap-sodium, tolfenpyrad, tralomethrin, triazamate, trichlorfon and triflumuron; and biological agents including entomopathogenic bacteria, such as *Bacillus thuringiensis* subsp. *aizawai, Bacillus thuringiensis* subsp. *kurstaki,* and the encapsulated delta-endotoxins of *Bacillus thuringiensis* (e.g., Cellcap, MPV, MPVII); entomopathogenic fungi, such as green muscardine fungus; and entomopathogenic virus including baculovirus, nucleopolyhedro virus (NPV) such as HzNPV, AfNPV; and granulosis virus (GV) such as CpGV.

Compounds of this invention and compositions thereof can be applied to plants genetically transformed to express proteins toxic to invertebrate pests (such as *Bacillus thuringiensis* delta-endotoxins). The effect of the exogenously applied fungicidal compounds of this invention may be synergistic with the expressed toxin proteins.

General references for agricultural protectants (i.e. insecticides, fungicides, nematocides, acaricides, herbicides and biological agents) include *The Pesticide Manual,* 13th Edition, C. D. S. Tomlin, Ed., British Crop Protection Council, Farnham, Surrey, U.K., 2003 and *The BioPesticide Manual, 2nd Edition,* L. G. Copping, Ed., British Crop Protection Council, Farnham, Surrey, U.K., 2001.

For embodiments where one or more of these various mixing partners are used, the weight ratio of these various mixing partners (in total) to the compound of Formula 1 is typically between about 1:3000 and about 3000:1. Of note are weight ratios between about 1:300 and about 300:1 (for example ratios between about 1:30 and about 30:1). One skilled in the art can easily determine through simple experimentation the biologically effective amounts of active ingredients necessary for the desired spectrum of biological activity. It will be evident that including these additional components may expand the spectrum of diseases controlled beyond the spectrum controlled by the compound of Formula 1 alone.

In certain instances, combinations of a compound of this invention with other biologically active (particularly fungicidal) compounds or agents (i.e. active ingredients) can result in a greater-than-additive (i.e. synergistic) effect. Reducing the quantity of active ingredients released in the environment while ensuring effective pest control is always desirable. When synergism of fungicidal active ingredients occurs at application rates giving agronomically satisfactory levels of fungal control, such combinations can be advantageous for reducing crop production cost and decreasing environmental load.

Of note is a combination of a compound of Formula 1 with at least one other fungicidal active ingredient. Of particular note is such a combination where the other fungicidal active ingredient has different site of action from the compound of Formula 1. In certain instances, a combination with at least one other fungicidal active ingredient having a similar spectrum of control but a different site of action will be particularly advantageous for resistance management. Thus, a composition of the present invention can further comprise a biologically effective amount of at least one additional fungicidal active ingredient having a similar spectrum of control but a different site of action.

Of particular note are compositions which in addition to compound of Formula 1 include at least one compound selected from the group consisting of (1) alkylenebis(dithiocarbamate)fungicides; (2) cymoxanil; (3) phenylamide fungicides; (4) proquinazid(6-iodo-3-propyl-2-propyloxy-4 (3H)-quinazolinone); (5) chlorothalonil; (6) carboxamides acting at complex II of the fungal mitochondrial respiratory electron transfer site; (7) quinoxyfen; (8) metrafenone; (9) cyflufenamid; (10) cyprodinil; (11) copper compounds; (12) phthalimide fungicides; (13) fosetyl-aluminum; (14) benzimidazole fungicides; (15) cyazofamid; (16) fluazinam; (17) iprovalicarb; (18) propamocarb; (19) validomycin; (20) dichlorophenyl dicarboximide fungicides; (21) zoxamide; (22) fluopicolide; (23) mandipropamid; (24) carboxylic acid amides acting on phospholipid biosynthesis and cell wall deposition; (25) dimethomorph; (26) non-DMI sterol biosynthesis inhibitors; (27) inhibitors of demethylase in sterol biosynthesis; (28) $bc_1$ complex fungicides; and salts of compounds of (1) through (28).

Further descriptions of classes of fungicidal compounds are provided below.

Sterol biosynthesis inhibitors (group (27)) control fungi by inhibiting enzymes in the sterol biosynthesis pathway. Demethylase-inhibiting fungicides have a common site of action within the fungal sterol biosynthesis pathway, involving inhibition of demethylation at position 14 of lanosterol or 24-methylene dihydrolanosterol, which are precursors to sterols in fungi. Compounds acting at this site are often referred to as demethylase inhibitors, DMI fungicides, or DMIs. The demethylase enzyme is sometimes referred to by other names in the biochemical literature, including cytochrome P-450 (14DM). The demethylase enzyme is described in, for example, *J. Biol. Chem.* 1992, 267, 13175-79 and references cited therein. DMI fungicides are divided between several chemical classes: azoles (including triazoles and imidazoles), pyrimidines, piperazines and pyridines. The triazoles include azaconazole, bromuconazole, cyproconazole, difenoconazole, diniconazole (including diniconazole-M), epoxiconazole, etaconazole, fenbuconazole, fluquinconazole, flusilazole, flutriafol, hexaconazole, imibenconazole, ipconazole, metconazole, myclobutanil, penconazole, propiconazole, prothioconazole, quinconazole, simeconazole, tebuconazole, tetraconazole, triadimefon, triadimenol, triticonazole and uniconazole. The imidazoles include clotrimazole, econazole, imazalil, isoconazole, miconazole, oxpoconazole, prochloraz and triflumizole. The pyrimidines include fenarimol, nuarimol and triarimol. The piperazines include triforine. The pyridines include buthiobate and pyrifenox. Biochemical investigations have shown that all of the above mentioned fungicides are DMI fungicides as described by K. H. Kuck et al. in *Modern Selective Fungicides—Properties, Applications and Mechanisms of Action,* H. Lyr (Ed.), Gustav Fischer Verlag: New York, 1995, 205-258.

$bc_1$ Complex Fungicides (group 28) have a fungicidal mode of action which inhibits the $bc_1$ complex in the mitochondrial respiration chain. The $bc_1$ complex is sometimes referred to by other names in the biochemical literature, including complex III of the electron transfer chain, and ubihydroquinone:cytochrome c oxidoreductase. This complex is uniquely identified by Enzyme Commission number EC1.10.2.2. The $bc_1$ complex is described in, for example, *J. Biol. Chem.* 1989, 264, 14543-48; *Methods Enzymol.* 1986, 126, 253-71; and references cited therein. Strobilurin fungicides such as azoxystrobin, dimoxystrobin, enestroburin (SYP-Z071), fluoxastrobin, kresoxim-methyl, metominostrobin, orysastrobin, picoxystrobin, pyraclostrobin, pyrametostrobin, pyraoxystrobin and trifloxystrobin are known to have this mode of action (H. Sauter et al., *Angew. Chem. Int. Ed.* 1999, 38, 1328-1349). Other fungicidal compounds that inhibit the bc₁ complex in the mitochondrial respiration chain include famoxadone and fenamidone.

Alkylenebis(dithiocarbamate)s (group (1)) include compounds such as mancozeb, maneb, propineb and zineb. Phenylamides (group (3)) include compounds such as metalaxyl, benalaxyl, furalaxyl and oxadixyl. Carboxamides (group (6)) include compounds such as boscalid, carboxin, fenfuram, flutolanil, furametpyr, mepronil, oxycarboxin, thifluzamide, penthiopyrad and N-[2-(1,3-dimethylbutyl)phenyl]-5-fluoro-1,3-dimethyl-1H-pyrazole-4-carboxamide (PCT Patent Publication WO 2003/010149), and are known to inhibit mitochondrial function by disrupting complex II (succinate dehydrogenase) in the respiratory electron transport chain. Copper compounds (group (11)) include compounds such as copper oxychloride, copper sulfate and copper hydroxide, including compositions such as Bordeaux mixture (tribasic copper sulfate). Phthalimides (group (12)) include compounds such as folpet and captan. Benzimidazole fungicides (group (14)) include benomyl and carbendazim. Dichlorophenyl dicarboximide fungicides (group (20)) include chlozolinate, dichlozoline, iprodione, isovaledione, myclozolin, procymidone and vinclozolin.

Non-DMI sterol biosynthesis inhibitors (group (26)) include morpholine and piperidine fungicides. The morpholines and piperidines are sterol biosynthesis inhibitors that have been shown to inhibit steps in the sterol biosynthesis pathway at a point later than the inhibitions achieved by the DMI sterol biosynthesis (group (27)). The morpholines include aldimorph, dodemorph, fenpropimorph, tridemorph and trimorphamide. The piperidines include fenpropidin.

Of further note are combinations of compounds of Formula 1 with azoxystrobin, kresoxim-methyl, trifloxystrobin, pyraclostrobin, picoxystrobin, dimoxystrobin, metominostrobin/fenominostrobin, carbendazim, chlorothalonil, quinoxyfen, metrafenone, cyflufenamid, fenpropidine, fenpropimorph, bromuconazole, cyproconazole, difenoconazole, epoxiconazole, fenbuconazole, flusilazole, hexaconazole, ipconazole, metconazole, penconazole, propiconazole, proquinazid, prothioconazole, tebuconazole, triticonazole, famoxadone, prochloraz, penthiopyrad and boscalid (nicobifen).

Preferred for better control of plant diseases caused by fungal plant pathogens (e.g., lower use rate or broader spectrum of plant pathogens controlled) or resistance management are mixtures of a compound of this invention with a fungicide selected from the group: azoxystrobin, kresoxim-methyl, trifloxystrobin, pyraclostrobin, picoxystrobin, dimoxystrobin, metominostrobin/fenominostrobin, quinoxyfen, metrafenone, cyflufenamid, fenpropidine, fenpropimorph, cyproconazole, epoxiconazole, flusilazole, metconazole, propiconazole, proquinazid, prothioconazole, tebuconazole, triticonazole, famoxadone and penthiopyrad.

Specifically preferred mixtures (compound numbers refer to compounds in Index Tables A-C) are selected from the group: combinations of Compound 23, Compound 11, Compound 13, Compound 18, Compound 19 or Compound 22 with ametoctradin, combinations of Compound 23, Compound 11, Compound 13, Compound 18, Compound 19 or Compound 22 with azoxystrobin, combinations of Compound 23, Compound 11, Compound 13, Compound 18, Compound 19 or Compound 22 with bixafen, combinations of Compound 23, Compound 11, Compound 13, Compound 18, Compound 19 or Compound 22 with boscalid, combinations of Compound 23, Compound 11, Compound 13, Compound 18, Compound 19 or Compound 22 with cyflufenamid, combinations of Compound 23, Compound 11, Compound 13, Compound 18, Compound 19 or Compound 22 with cyproconazole, combinations of Compound 23, Compound 11, Compound 13, Compound 18, Compound 19 or Compound 22 with dimoxystrobin, combinations of Compound 23, Compound 11, Compound 13, Compound 18, Compound 19 or Compound 22 with epoxiconazole, combinations of Compound 23, Compound 11, Compound 13, Compound 18, Compound 19 or Compound 22 with famoxadone, combinations of Compound 23, Compound 11, Compound 13, Compound 18, Compound 19 or Compound 22 with fenpropidine, combinations of Compound 23, Compound 11, Compound 13, Compound 18, Compound 19 or Compound 22 with fenpropimorph, combinations of Compound 23, Compound 11, Compound 13, Compound 18, Compound 19 or Compound 22 with fluopyram, combinations of Compound 23, Compound 11, Compound 13, Compound 18, Compound 19 or Compound 22 with flusilazole, combinations of Compound 23, Compound 11, Compound 13, Compound 18, Compound 19 or Compound 22 with flutianil, combinations of Compound 23, Compound 11, Compound 13, Compound 18, Compound 19 or Compound 22 with isopyrazam, combinations of Compound 23, Compound 11, Compound 13, Compound 18, Compound 19 or Compound 22 with isotianil, combinations of Compound 23, Compound 11, Compound 13, Compound 18, Compound 19 or Compound 22 with kresoxim-methyl, combinations of Compound 23, Compound 11, Compound 13, Compound 18, Compound 19 or Compound 22 with mandipropamid, combinations of Compound 23, Compound 11, Compound 13, Compound 18, Compound 19 or Compound 22 with meptyldinocap, combinations of Compound 23, Compound 11, Compound 13, Compound 18, Compound 19 or Compound 22 with metconazole, combinations of Compound 23, Compound 11, Compound 13, Compound 18, Compound 19 or Compound 22 with metominostrobinifenominostrobin, combinations of Compound 23, Compound 11, Compound 13, Compound 18, Compound 19 or Compound 22 with metrafenone, combinations of Compound 23, Compound 11, Compound 13, Compound 18, Compound 19 or Compound 22 with penflufen, combinations of Compound 23, Compound 11, Compound 13, Compound 18, Compound 19 or Compound 22 with penthiopyrad, combinations of Compound 23, Compound 11, Compound 13, Compound 18, Compound 19 or Compound 22 with picoxystrobin, combinations of Compound 23, Compound 11, Compound 13, Compound 18, Compound 19 or Compound 22 with propiconazole, combinations of Compound 23, Compound 11, Compound 13, Compound 18, Compound 19 or Compound 22 with proquinazid, combinations of Compound 23, Compound 11, Compound 13, Compound 18, Compound 19 or Compound 22 with prothioconazole, combinations of Compound 23, Compound 11, Compound 13, Compound 18, Compound 19 or Compound 22 with pyraclostrobin, combinations of Compound 23, Compound 11, Compound 13, Compound 18, Compound 19 or Compound 22 with pyrametostrobin, combinations of Compound 23, Compound 11, Compound 13, Compound 18, Compound 19 or Compound 22 with pyraoxystrobin, combinations of Compound 23, Compound 11, Compound 13, Compound 18, Compound 19 or Compound 22 with pyribencarb, combinations of Compound 23, Compound 11, Compound 13, Compound 18, Compound 19 or Compound 22 with quinoxyfen, combinations of Compound 23, Compound 11, Compound 13, Compound 18, Compound 19 or Compound 22 with tebuconazole, combinations of Compound 23, Compound 11, Compound 13, Compound 18, Compound 19 or Compound 22 with tebufloquin, combinations of Compound 23, Compound 11, Compound 13, Compound 18, Compound 19 or Compound 22 with trifloxystrobin, combinations of Compound 23, Compound 11, Compound 13, Compound 18, Compound 19 or Compound 22 with triticonazole and combinations of Compound 23, Compound 11, Compound 13, Compound 18, Compound 19 or Compound 22 with valifenalate.

The following Tests demonstrate the control efficacy of compounds of this invention on specific pathogens. The pathogen control protection afforded by the compounds is not limited, however, to these species. See Index Tables A-C for compound descriptions. The following abbreviations are used in the Index Tables which follow: t is tertiary, Me is methyl, Et is ethyl and t-Bu is tert-butyl. The abbreviation "Ex." stands for "Example" and is followed by a number indicating in which example the compound is prepared.

The compounds of this invention prepared by the methods described herein are shown in Index Tables A-C. For mass spectral data (Al$^3$±(M+1)), the numerical value reported is the molecular weight of the parent molecular ion (M) formed by addition of H$^+$ (molecular weight of 1) to the molecule to give a M+1 peak observed by mass spectrometry using atmospheric pressure chemical ionization (AP$^+$). The alternate molecular ion peaks (e.g., M+2 or M+4) that occur with compounds containing multiple halogens are not reported.

INDEX TABLE A

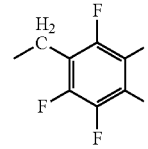

| Cmpd. | R$^{12}$ | Z | AP+ (M + 1) |
|---|---|---|---|
| 1 | 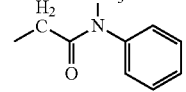 | H | 582 |
| 2 | 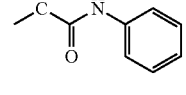 | H | * |
| 3 | 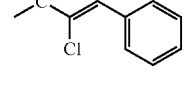 | H | * |
| 4 | 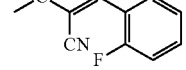 | H | * |
| 5 | 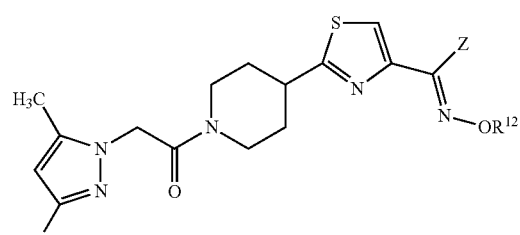 | H | * |

INDEX TABLE A-continued

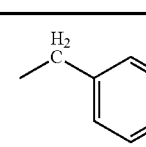

| Cmpd. | R$^{12}$ | Z | AP+ (M + 1) |
|---|---|---|---|
| 6 | 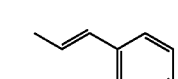 | H | * |
| 7 | H | Cl | * |
| 8 (Ex. 8) | H | H | ** |
| 9 | CH$_3$ | 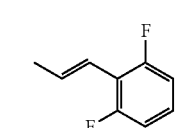 | 518 |
| 10 (Ex. 1) | H | CH$_3$ | ** |
| 11 (Ex. 2) | H | 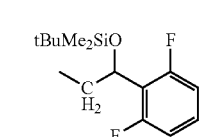 | ** |
| 12 (Ex. 6) | H | 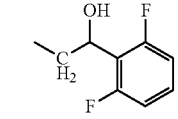 | ** |
| 13 (Ex. 6) | H | 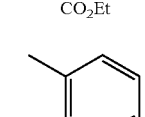 | ** |
| 14 | H | CO$_2$Et | 474 |
| 15 (isomer A) (Ex. 7) | H | 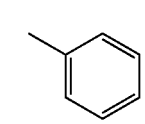 | ** |
| 16 (isomer B) (Ex. 7) | H | 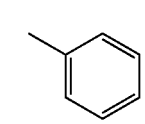 | ** |

INDEX TABLE A-continued

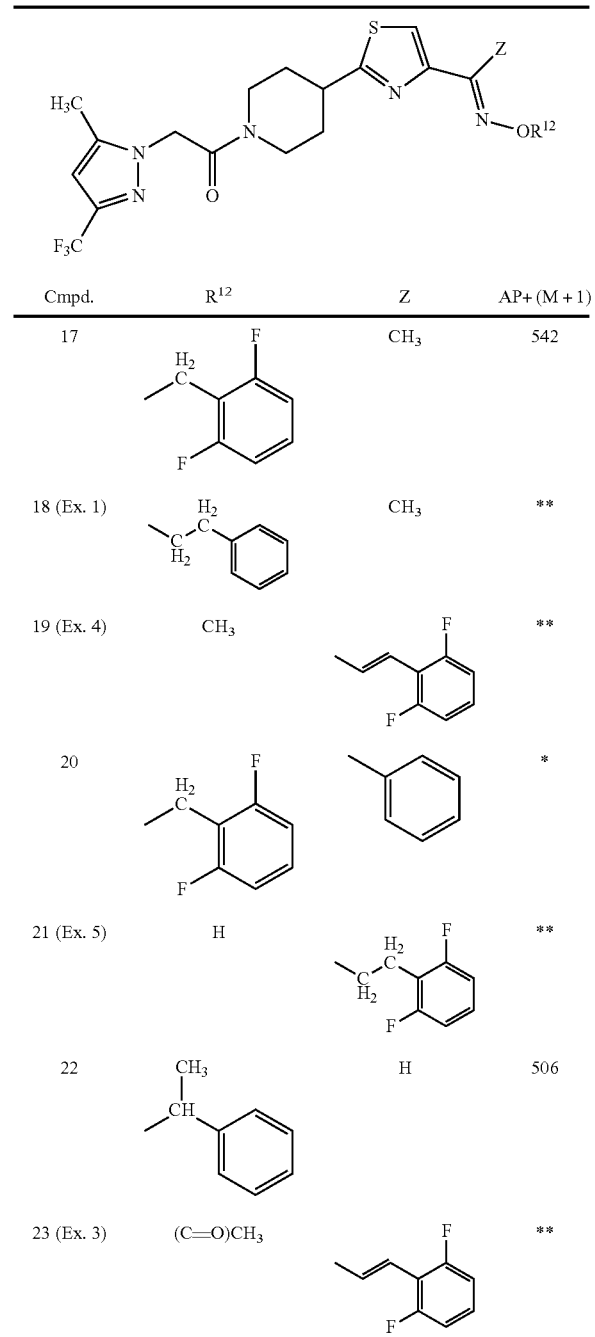

| Cmpd. | R[12] | Z | AP+ (M + 1) |
|---|---|---|---|
| 17 | 2,6-difluorobenzyl | CH₃ | 542 |
| 18 (Ex. 1) | phenethyl (–CH₂CH₂Ph) | CH₃ | ** |
| 19 (Ex. 4) | CH₃ | (E)-2-(2,6-difluorophenyl)ethenyl | ** |
| 20 | 2,6-difluorobenzyl | phenyl | * |
| 21 (Ex. 5) | H | 2-(2,6-difluorophenyl)ethyl | ** |
| 22 | 1-phenylethyl (CH(CH₃)Ph) | H | 506 |
| 23 (Ex. 3) | (C=O)CH₃ | (E)-2-(2,6-difluorophenyl)ethenyl | ** |

INDEX TABLE A-continued

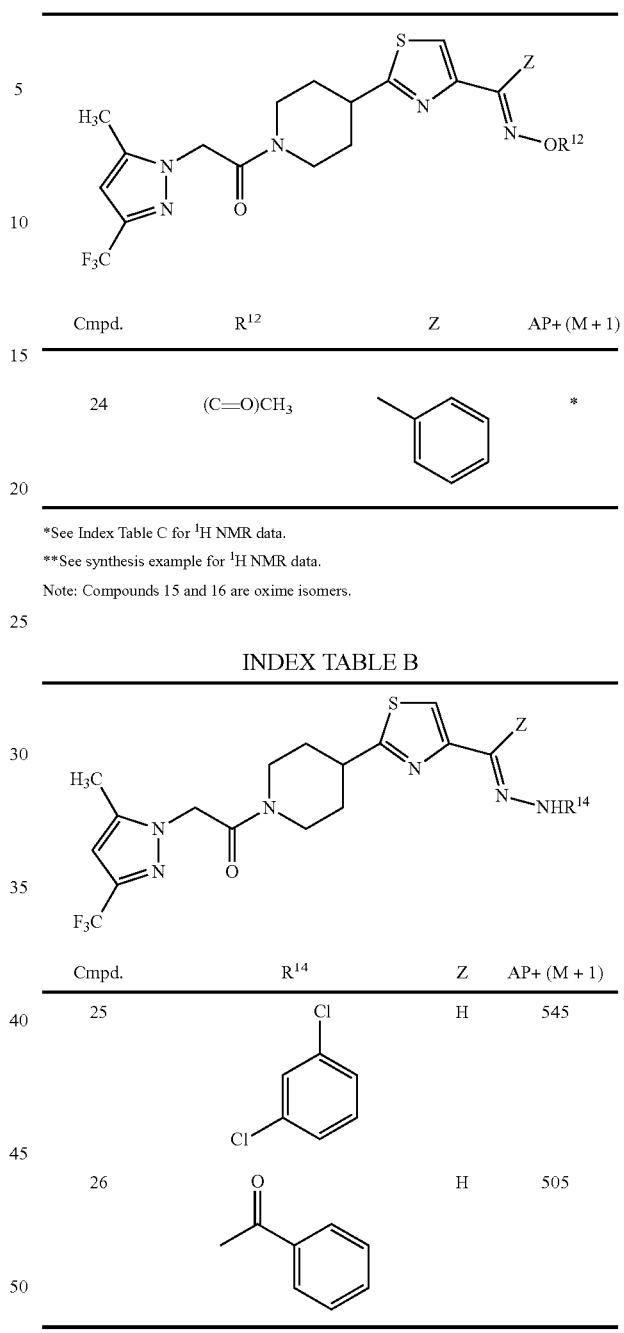

| Cmpd. | R[12] | Z | AP+ (M + 1) |
|---|---|---|---|
| 24 | (C=O)CH₃ | phenyl | * |

*See Index Table C for ¹H NMR data.
**See synthesis example for ¹H NMR data.
Note: Compounds 15 and 16 are oxime isomers.

INDEX TABLE B

| Cmpd. | R[14] | Z | AP+ (M + 1) |
|---|---|---|---|
| 25 | 3,5-dichlorophenyl | H | 545 |
| 26 | 3-acetylphenyl | H | 505 |

INDEX TABLE C

| Compd. No. | ¹H NMR Data (CDCl₃ solution unless indicated otherwise)[a] |
|---|---|
| 2 | δ 1.83-1.62 (m, 2H), 2.25-2.08 (m 2H), 2.29 (s, 3H), 2.93-2.73 (m, 1H), 3.37-3.17 (m, 5H), 4.07-3.93 (m, 1H), 4.67-4.48 (m, 3H), 5.03-4.90 (m, 2H), 6.31 (s, 1H), 7.47-7.16 (m, 6H), 8.41 (s, 1H). |
| 3 | δ 1.85-1.64 (m, 2H), 2.27-2.09 (m 2H), 2.29 (s, 3H), 2.90-2.75 (m, 1H), 3.38-3.19 (m, 2H), 4.07-3.95 (m, 1H), 4.64-4.53 (m, 1H), 4.79 (s, 2H), 5.02-4.88 (m, 2H), 6.31 (s, 1H), 7.16-7.06 (m, 1H), 7.37-7.26 (m, 2H), 7.60-7.48 (m, 3H), 7.98 (s, 1H), 8.37 (s, 1H). |
| 4 | δ 1.83-1.65 (m, 2H), 2.64-2.10 (m 2H), 2.29 (s, 3H), 2.90-2.74 (m, 1H), 3.41-3.17 (m, 2H), 4.08-3.93 (m, 1H), 4.67-4.51 (m, 1H), 4.89 (s, 2H), 5.06-4.90 (m, 2H), 6.32 (s, 1H), 6.79 (s, 1H), 7.39-7.23 (m, 3H), 7.48 (s, 1H), 7.69-7.61 (m, 2H), 8.29 (s, 1H). |

INDEX TABLE C-continued

| Compd. No. | ¹H NMR Data (CDCl₃ solution unless indicated otherwise)[a] |
|---|---|
| 5 | δ 1.84-1.65 (m, 2H), 2.27-2.10 (m 2H), 2.30 (s, 3H), 2.90-2.78 (m, 1H), 3.39-3.20 (m, 2H), 4.07-3.96 (m, 1H), 4.64-4.53 (m, 1H), 4.96 (s, 2H), 5.07-4.91 (m, 2H), 6.32 (s, 1H), 7.01-6.91 (m, 2H), 7.16 (s, 1H), 7.41-7.30 (m, 1H), 7.52 (s, 1H), 8.29 (s, 1H). |
| 6 | δ 2.19-2.26 (m, 2 H), 2.32 (two s, 3 H), 2.80-2.85 (m, 1 H), 3.23-3.32 (m, 2 H), 4.01-4.08 (m, 2 H), 4.57-4.65 (m, 2 H), 4.99 (m, 2 H), 5.24-5.31 (m, 2 H), 6.32-6.36 (m, 1 H), 7.31-7.43 (m, 5 H), 7.45 (s, 1 H), 8.22-8.26 (two s, 1 H) mix of syn and anti isomers. |
| 7 | δ 1.65-1.85 (m, 2H), 2.15-2.30 (m, 2H), 2.30 (s, 3H), 2.85 (t, 1H), 3.20-3.40 (m, 2H), 4.00 (d, 1H), 4.60 (d, 1H), 4.95-5.05 (m, 2H), 6.33 (s, 1H), 7.68 (s, 1H), 10.48 (br s, 1H). |
| 20 | δ 1.65-1.80 (m, 2H), 2.16 (br t, 2H), 2.30 (s, 3H), 2.87 (t, 1H), 3.21-3.33 (m, 2H), 3.96 (d, 1H), 4.45 (d, 1H), 4.90-5.00 (m, 2H), 5.40 (s, 2H), 6.33 (s, 1H), 6.92 (t, 2H), 7.27-7.40 (m, 4H), 7.55 (d, 2H), 8.02 (s, 1H). |
| 24 | δ 1.70-1.85 (m, 2H), 2.22 (br t, 2H), 2.26 (s, 3H), 2.32 (s, 3H), 2.85 (t, 1H), 3.20-3.35 (m, 2H), 4.03 (d, 1H), 4.53 (d, 1H), 4.92-5.02 (m, 2H), 6.35 (s, 1H), 7.18-7.65 (m, 5H), 7.82 (s, 1H). |

[a]¹H NMR data are in ppm downfield from tetramethylsilane. Couplings are designated by (s)—singlet, (d)—doublet, (t)—triplet, (m)—multiplet, (dd)—doublet of doublets, (dt)—doublet of triplets, (br s)—broad singlet, (br t)—broad triplet.

BIOLOGICAL EXAMPLES OF THE INVENTION

General protocol for preparing test suspensions for Test A-C: The test compounds were first dissolved in acetone in an amount equal to 3% of the final volume and then suspended at the desired concentration (in ppm) in acetone and purified water (50/50 mix by volume) containing 250 ppm of the surfactant Trem® 014 (polyhydric alcohol esters). The resulting test suspensions were then used in Tests A-C. Spraying a 40 ppm test suspension to the point of run-off on the test plants was equivalent to a rate of 160 g/ha.

Test A

Grape seedlings were inoculated with a spore suspension of *Plasmopara viticola* (the causal agent of grape downy mildew) and incubated in a saturated atmosphere at 20° C. for 24 h. After a short drying period, the test suspension was sprayed to the point of run-off on the grape seedlings, which were then moved to a growth chamber at 20° C. for 5 days, after which time the grape seedling were placed back into a saturated atmosphere at 20° C. for 24 h. Upon removal, visual disease ratings were made.

Test B

The test suspension was sprayed to the point of run-off on tomato seedlings. The following day the seedlings were inoculated with a spore suspension of *Phytophthora infestans* (the causal agent of tomato late blight) and incubated in a saturated atmosphere at 20° C. for 24 h, and then moved to a growth chamber at 20° C. for 5 days, after which time visual disease ratings were made.

Test C

Tomato seedlings were inoculated with a spore suspension of *Phytophthora infestans* (the causal agent of tomato late blight) and incubated in a saturated atmosphere at 20° C. for 17 h. After a short drying period, the test suspension was sprayed to the point of run-off on the tomato seedlings, which were then moved to a growth chamber at 20° C. for 4 days, after which time visual disease ratings were made.

In addition to Tests A-C, the compounds were also sprayed on 2 separate sets of tomato plants, which were inoculated with *Botrytis cinerea* or *Alternaria solani* 24 h after treatment, and wheat plants, which were inoculated with *Blumeria graminis* f. sp. *tritici*. Test compounds did not show noticeable activity against these additional pathogens under the test conditions at the application rates tested.

Results for Tests A-C are given in Table A. In the table, a rating of 100 indicates 100% disease control and a rating of 0 indicates no disease control (relative to the controls), "*" indicates data from applications of 200 ppm, and "- - -" denotes no data for this assay.

TABLE A

| Cmpd No. | Test A | Test B | Test C |
|---|---|---|---|
| 1 | 15 | 53 | 17 |
| 2 | 0 | 95 | 0 |
| 3 | 0 | 65 | 0 |
| 4 | 33 | 91 | 0 |
| 5 | 0 | 73 | 0 |
| 6 | 93 | 71 | 46 |
| 8 | 99 | 100 | 97 |
| 9 | 51 | 70 | 0 |
| 10 | 71 | 100 | — |
| 11 | 100 | 100 | 98 |
| 12 | 0 | 40* | — |
| 13 | 93 | 100 | 97 |
| 14 | 0 | 58 | 9 |
| 15 | 55 | 100 | — |
| 16 | 0 | 89 | 0 |
| 17 | 76 | 91 | — |
| 18 | 93 | 97 | — |
| 19 | 83 | 100 | — |
| 20 | 0 | 47 | 0 |
| 21 | 57 | 100 | — |
| 22 | 97 | 100 | — |
| 23 | 99 | 100 | 99 |
| 24 | 0 | 58 | 9 |
| 25 | 0 | 0 | 17 |
| 26 | 9 | 50 | 0 |

What is claimed is:

1. A compound selected from Formula 1, N-oxides and salts thereof,

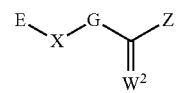

1 wherein
E is

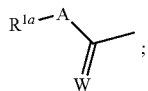 E-1

$R^{1a}$ is

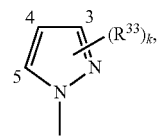 U-1

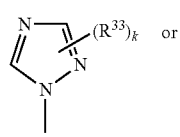 U-20 or

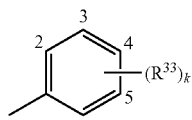 U-50 wherein when $R^{33}$ is attached to a carbon ring member, said $R^{33}$ is selected from $R^{33a}$;
each $R^{33a}$ is independently halogen, $C_1$-$C_3$ alkyl, $C_1$-$C_3$ haloalkyl or $C_2$-$C_3$ alkoxyalkyl;
k is 0, 1, 2 or 3;
A is $CHR^{15}$;
$R^{15}$ is H;
W is O;
X is

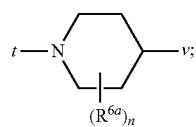 X-1 n is 0;
G is

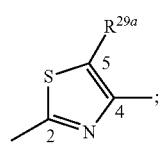 G-1

$R^{29a}$ is H;

$W^2$ is selected from

 J-1

 J-2 and

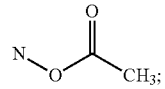 J-4

Z is $C_1$-$C_4$ hydroxyalkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_2$-$C_4$ alkoxyalkyl, $C_2$-$C_4$ alkylthioalkyl, $C_2$-$C_4$ alkylsulfinylalkyl, $C_2$-$C_4$ alkylsulfonylalkyl, $C_2$-$C_4$ alkylcarbonyl, $C_2$-$C_4$ haloalkylcarbonyl, $C_2$-$C_5$ alkoxycarbonyl, $C_2$-$C_5$ alkylaminocarbonyl, $C_3$-$C_5$ dialkylaminocarbonyl or $C_2$-$C_4$ aminocarbonylalkyl, each substituted by one Q;
Q is

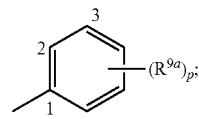 Q-45 each $R^{9a}$ is independently halogen, $C_1$-$C_6$ alkyl, $C_1$-$C_6$ haloalkyl or $C_1$-$C_4$ alkoxy; and
p is 0, 1, 2 or 3.

2. The compound of claim 1 which is selected from the group:
3-(2,6-difluorophenyl)-3-hydroxy-1-[2-[1-[2-[5-methyl-3-(trifluoromethyl)-1H-pyrazol-1-yl]acetyl]-4-piperidinyl]-4-thiazolyl]-1-propanone 1-oxime;
3-(2,6-difluorophenyl)-1-[2-[1-[2-[5-methyl-3-(trifluoromethyl)-1H-pyrazol-1-yl]acetyl]-4-piperidinyl]-4-thiazolyl]-2-propen-1-one 1-oxime;
3-(2,6-difluorophenyl)-1-[2-[1-[2-[5-methyl-3-(trifluoromethyl)-1H-pyrazol-1-yl]acetyl]-4-piperidinyl]-4-thiazolyl]-2-propen-1-one 1-(O-methyloxime); and
3-(2,6-difluorophenyl)-1-[2-[1-[2-[5-methyl-3-(trifluoromethyl)-1H-pyrazol-1-yl]acetyl]-4-piperidinyl]-4-thiazolyl]-2-propen-1-one 1-(O-acetyloxime).

3. A fungicidal composition comprising (a) a compound of claim 1; and (b) at least one other fungicide.

4. A fungicidal composition comprising (a) a compound of claim 1; and (b) at least one additional component selected from the group consisting of surfactants, solid diluents and liquid diluents.

5. A method for controlling plant diseases caused by fungal plant pathogens comprising applying to the plant or portion thereof, or to the plant seed, a fungicidally effective amount of a compound of claim 1.

* * * * *